(12) United States Patent
Lee et al.

(10) Patent No.: US 9,421,245 B2
(45) Date of Patent: *Aug. 23, 2016

(54) TARGETED THERAPEUTICS

(71) Applicant: The Brigham and Women's Hospital, Inc., Boston, MA (US)

(72) Inventors: Richard T. Lee, Weston, MA (US); Parth Patwari, Cambridge, MA (US); Francesco Loffredo, Boston, MA (US); James Pancoast, Cambridge, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/409,270

(22) PCT Filed: Jun. 25, 2013

(86) PCT No.: PCT/US2013/047550
§ 371 (c)(1),
(2) Date: Dec. 18, 2014

(87) PCT Pub. No.: WO2014/004465
PCT Pub. Date: Jan. 3, 2014

(65) Prior Publication Data
US 2015/0182596 A1  Jul. 2, 2015

Related U.S. Application Data

(60) Provisional application No. 61/663,679, filed on Jun. 25, 2012.

(51) Int. Cl.
| C07K 14/475 | (2006.01) |
| C07K 14/65 | (2006.01) |
| A61K 31/727 | (2006.01) |
| A61K 38/18 | (2006.01) |
| A61K 38/30 | (2006.01) |
| A61K 38/16 | (2006.01) |
| C07K 14/47 | (2006.01) |
| C07K 14/635 | (2006.01) |
| A61K 38/29 | (2006.01) |
| A61K 38/00 | (2006.01) |

(52) U.S. Cl.
CPC ............. *A61K 38/30* (2013.01); *A61K 38/16* (2013.01); *A61K 38/29* (2013.01); *C07K 14/47* (2013.01); *C07K 14/635* (2013.01); *C07K 14/65* (2013.01); *A61K 38/00* (2013.01); *C07K 2319/00* (2013.01); *C07K 2319/01* (2013.01); *C07K 2319/33* (2013.01)

(58) Field of Classification Search
None
See application file for complete search history.

(56) References Cited

U.S. PATENT DOCUMENTS

| 5,670,483 | A | 9/1997 | Zhang et al. |
| 5,786,217 | A | 7/1998 | Tubo et al. |
| 6,037,329 | A | 3/2000 | Baird et al. |
| 6,150,163 | A | 11/2000 | McPherson et al. |
| 6,337,072 | B1* | 1/2002 | Ford .................... C07K 14/545 424/1.69 |
| 6,548,630 | B1 | 4/2003 | Zhang et al. |
| 6,855,801 | B1* | 2/2005 | San Antonio ........ C07K 14/001 530/300 |
| 7,399,831 | B2 | 7/2008 | Lee et al. |
| 7,429,567 | B2 | 9/2008 | Lee et al. |
| 2003/0187232 | A1 | 10/2003 | Hubbell et al. |
| 2004/0087505 | A1 | 5/2004 | Pena et al. |
| 2005/0222394 | A1 | 10/2005 | Zamora et al. |
| 2006/0088510 | A1 | 4/2006 | Lee et al. |
| 2006/0148703 | A1 | 7/2006 | Lee et al. |
| 2006/0172931 | A1 | 8/2006 | San Antonio et al. |
| 2007/0081992 | A1 | 4/2007 | Pardridge et al. |
| 2007/0117177 | A1* | 5/2007 | Luo ........................ C12P 21/00 435/68.1 |
| 2008/0138323 | A1* | 6/2008 | Lee ........................ C07H 21/04 424/93.7 |
| 2009/0312265 | A1* | 12/2009 | Schmidtchen et al. ......... 514/15 |

FOREIGN PATENT DOCUMENTS

| JP | 2003522160 A | 7/2003 |
| JP | 2005500052 A | 1/2005 |
| JP | 2005504025 A | 2/2005 |

(Continued)

OTHER PUBLICATIONS

Tokuriki et al. Stability effects of mutations and protein evolvability, Current Opinion in Structural Biology, 19:596-604 (2009).*
Wells, J.A. Additivity of Mutational Effects in Proteins. Biochemistry 29:8509-8517 (1990).*
Ngo et al. Computational Complexity, Protein Structure Prediction and the Levinthal Paradox. The Protein Folding Problem and Tertiary Structure Prediction, pp. 433-440 and 492-495; (1994).*
Florine et al., "Delivering Heparin-Binding Insulin-Like Growth Factor 1 with Self-Assembling Peptide Hydrogels" Tissue Engineering, 21:637-646 (2015).
Miller et al., "Effect of self-assembling peptide, chondrogenic factors, and bone marrow-derived stromal cells on osteochondral repair" Osteoarthritis and Cartilage 18:1608-1619 (2010).

(Continued)

*Primary Examiner* — Elizabeth C Kemmerer
*Assistant Examiner* — Regina M Deberry
(74) *Attorney, Agent, or Firm* — Brown Rudnick LLP; Thomas C. Meyers

(57) ABSTRACT

The present invention relates to compositions, methods and kits for delivery of active agents (X) to cells or tissues that express proteoglycans. More specifically, the present invention relates to conjugates comprising (HB-linker)$_n$-X$_m$-(linker-HB)$_o$, where HB is a heparin binding protein, X is an active agents such as a therapeutic protein (including a functional fragment or variant thereof), or a therapeutic small molecule, linker is a linker entity and m is an integer of at least 1, and n+o is an integer of at least 1. Other aspects relate to use of a HB-X conjugate in methods to deliver active agents to cartilage for the treatment of cartilage related disease and disorders, the use of the HB-X conjugate in methods to deliver active agents to neuronal tissues (e.g., brain and spinal cord) for the treatment of neurological disorders, and the use of the HB-X conjugates in methods for the treatment of eye conditions and disorders and inflammatory conditions and disorders.

25 Claims, 5 Drawing Sheets

(56) References Cited

FOREIGN PATENT DOCUMENTS

| | | | |
|---|---|---|---|
| JP | 2005517658 A | 6/2005 | |
| JP | 2010508845 A | 3/2010 | |
| WO | 93/19770 A1 | 10/1993 | |
| WO | WO-9608274 | * | 9/1995 |
| WO | 99/54359 | 10/1999 | |
| WO | 03/012045 A2 | 2/2003 | |
| WO | 2004/018499 A2 | 3/2004 | |
| WO | 2006/044614 A2 | 4/2006 | |
| WO | 2008/023063 A2 | 2/2008 | |
| WO | 2011/008773 A2 | 1/2011 | |
| WO | 2011146902 A1 | 11/2011 | |
| WO | 2012/082950 A2 | 6/2012 | |

OTHER PUBLICATIONS

Miller et al., "Intraarticular Injection of Heparin-Binding Insulin-like Growth Factor 1 Sustains Delivery of Insulin-like Growth Factor 1 to Cartilage Through Binding to Chondroitin Sulfate" Arthritis & Rheumatism 62(12):3686-3694 (2010).

Abraham et al., Biochemical and Biophysical Research Communications 190(1):125-133 (1993). "Heparin-binding EGF-like growth factor: characterization of rat and mouse cDNA clones, protein domain conservation across species, and transcript expression in tissues."

Ballard et al., Biochem J. Jan. 1, 1986;233(1)223-30. Binding properties and biological potencies of insulin-like growth factors in L6 myoblasts.

Brittberg et al., The new England Journal of Medicine 331(14):879-895 (1994). "Treatment of dep cartilage defects in the knee with autologous chondrocyte transplantation."

Chevalier et al., "Production of Binding Proteins and Role of the Insulin-Like Growth Factor I Binding Protein 3 in Human Articular Cartilage Explants," British J. Rheumatol. 35:515-522 (1996).

Congote et al. "Increased heparin binding by site directed mutagenesis of a recombinant chimera of bombyxin and insulin-like growth factor II," Biochimica et Biophysica Acta 1243:538-542 (1995).

Davis et al., "Local myocardial insulin-like growth factor 1 (IGF-1) delivery with biotinylated peptide nanofibers improves cell therapy for myocardial infarction," PNAS 103(21):8155-8160 (May 2006).

De Ceuninck et al., Arthritis Rheum. Aug. 2003;48(8):2197-206. "High binding capacity of cyclophilin B to chondrocyte heparan sulfate proteoglycans and its release from the cell surface by matrix metalloproteinases: possible role as a proinflammatory mediator in arthritis."

Kofidis et al., "Insulin-Like Growth Factor Promotes Engraftment, Differentiation, and Functional Improvement after Transfer of Embryonic Stem Cells for Myocardial Restoration," Stem Cells 22:1239-1245 (2004).

Li et al., "Overexpression of Insulin-like Growth Factor-1 in Mice Protects from Myocyte Death after Infarction, Attenuating Ventricular Dilation, Wall Stress, and Cardiac Hypertrophy," J. Clin. Invest. 100:1991-1999 (Oct. 1997).

Özdinler et al., "IGF-I Specifically Enhances Axon Outgrowth of Corticospinal Motor Neurons," Nature Neurosci. 9:1371-1381 (Nov. 2006).

Palmen et al., "Cardiac Remodeling after Myocardial Infarction is Impaired in IGF-1 Deficient Mice," Cardiovasc. Res. 50:516-524 (2001).

International Preliminary Report on Patentability for PCT/US2007/023527 filed Nov. 8, 2007. (Mailed May 19, 2009.).

International Search Report for PCT/US07/23527 filed Nov. 8, 2007. (Mailed Jun. 19, 2008.).

Written Opinion of the International Searching Authority for PCT/US07/23527 filed Nov. 8, 2007. (Mailed Jun. 19, 2008.).

Schmidt et al., "A review of the effects of insulin-like growth factor and platelet derived growth factor on in vivo cartilage healing and repair," OsteoArthritis and Cartilage 14:403-412 (2006).

Search Report prepared by the Hungarian Patent Office for Singapore Application No. 2009031444. (Mailed Jun. 10, 2012.).

Segev et al., "The role of perlecan in arterial injury and angiogenesis," Cardiovascular Res. 63:603-610 (2004).

Supplementary European Search Report for Application No. EP 07 86 7389. (Mailed Oct. 29, 2009.).

Thompson et al., "Characterization of Sequences within Heparin-binding EGF-like Growth Factor That Mediate Interaction with Heparin," J. Biol. Chem. 269(4):2541-2549 (Jan. 1994).

Tokunou et al., "Abstract 1269: Engineering a New Insulin-Like Growth Factor-1 Protein for Embryonic Stem Cell Therapy," Circulation 114(18 Suppl. S):239 (2006).

Tokunou et al., FASEB J. 22(6):1886-1893 (2008). "Engineering insulin-like growth factor-1 for local delivery."

Torella et al., "Cardiac Stem Cell and Myocyte Aging, Heart Failure, and Insulin-Like Growth Factor-1 Overexpression," Circ. Res. 94:514-524 (2004).

Vasan et al., "Serum Insulin-like Growth Factor I and Risk for Heart Failure in Elderly Individuals Without a Previous Myocardial Infarction: The Framingham Heart Study," Ann. Intern. Med. 139:642-648 (2003).

Vig, et al., "Intranasal administration of IGF-I improves behavior and Purkinje cell pathology in SCA1 mice," Brain Research Bulletin 69:573-579 (2006).

Vincent et al., "Basic FGF mediates an immediate response of articular cartilage to mechanical injury," PNAS 99 (12):8259-8264 (2002).

Wilczak et al., "Insulin-Like Growth Factor System in Amyotrophic lateral Sclerosis," Endocr. Dev. 9:160-169 (2005).

Written Opinion prepared by the Hungarian Patent Office for Singapore Application No. 2009031444. (Mailed Jun. 10, 2010.).

Zhang et al., "Spontaneous Assembly of a Self-Complementary Oligopeptide to Form a Stable Macroscopic Membrane," Proc. Natl. Acad. Sci. USA 90:3334-3338 (Apr. 1993).

Zhang et al., "Design of Nanostructured Biological Materials Through Self-Assembly of Peptides and Proteins," Curr. Opin. Chem. Biol. 6:865-871 (2002).

* cited by examiner

1. HB(C17K)-IGF-1
2. HB(C17R)-IGF-1
3. HB(C17S)-IGF-1
4. HB-IGF-1

Expression of HB-IGF-1 variants in detergent extracts

Enhanced HB (C17R)

Fractions after start of elution

Wild-type HB

Fractions after start of elution 1) eHB-IGF-1 Not Induced
2) eHB-IGF-1 Induced
3) wHB-IGF-1 Not Induced
4) wHB-IGF-1 Induced Peptide Standards Remaining in cartilage
after two days with no PTH

TARGETED THERAPEUTICS

CROSS REFERENCE TO RELATED APPLICATIONS

This application is a 35 U.S.C. §371 National Phase Entry Application of International Application No. PCT/US2013/047550 filed Jun. 25, 2013, which designates the U.S., and which claims benefit under 35 U.S.C. §119(e) of U.S. Provisional Application No. 61/663,679 filed on Jun. 25, 2012, the contents of which is incorporated herein by reference in its entirety.

FIELD OF THE INVENTION

The present invention relates generally to methods and compositions to deliver active agents, e.g., therapeutic agents, by conjugating, fusing, or non-direct linkage of the active agent to one or more heparin-binding peptides (HB). Other aspects relate to compositions, methods and kits comprising heparin-binding peptides (HB) fused or conjugated to the therapeutic agents.

SEQUENCE LISTING

The instant application contains a Sequence Listing which has been submitted electronically in ASCII format and is hereby incorporated by reference in its entirety. Said ASCII copy, created on Mar. 5, 2015, is named 043214-073182-US_SL.txt and is 65,038 bytes in size.

BACKGROUND OF THE INVENTION

Systemic administration or non-specific activity of therapeutic agents, such as recombinant cytokines and small molecules, can trigger off-target selequae. Thus there remains a need for targeted delivery of the active molecules to the site of interest.

SUMMARY OF THE INVENTION

The present embodiments provide for the selective delivery of recombinant therapeutic proteins or small molecules to cells or tissues that express proteoglycans, for example, but not limited to cartilage, brain and spinal cord tissue, skin and subcutaneous tissue. More specifically, some embodiments herein are directed to novel heparin-binding peptides (HB) fused to a therapeutic protein or a portion thereof, optionally by a linker peptide. Some embodiments provide for the conjugation or indirect linkage of small molecules to novel HB for selective delivery. The HB-agent compositions can be used in tandem for delivery of therapeutic proteins and agents to tissues.

An aspect of the present invention provides for a selective therapeutic composition comprising, for example, (HB-linker)$_n$-X$_m$-(linker-HB)$_o$, where HB is a heparin binding protein, X is an active agents such as a therapeutic protein or a portion thereof, or a therapeutic small molecule, and where n, m, and o are integers, and m is at least one and n+o is at least one. In some embodiments, a HB-X conjugate is HB-X$_n$, or (HB-linker)$_n$-X$_n$, and where n is an integer of at least 1. In some embodiments, the composition is a recombinant fusion protein comprising a recombinant HB and the therapeutic protein (or portion thereof). The components of the composition can be placed in order, relative to the N-terminus of the HB portion of the composition: HB-X, X-HB, HB-linker-X, (HB-linker)$_2$-X, X-linker-HB, X-HB-X, HB$_n$-X-HB$_n$, (HB-linker)$_n$-X-(linker-HB)$_n$, HB-X-HB-X, etc. Additionally, the composition can comprise a mixture of HB-X constructs, wherein X represents different proteins or small molecules (i.e., a composition comprising HB-X$^1$ and HB-X$^2$, etc.). An example linker is a peptide comprising the amino acids GGG. Other linkers commonly known in the art are encompassed for use in the HB-X conjugate, such as known peptide linkers and chemical linkers.

More specifically, the HB portion of the composition is positively charged through many lysine and arginine residues in the HB peptide, which binds to cellular or tissue expressing proteoglycans which are negatively charged by sulfate groups. In particular embodiments, the HB is mutated to enhance the positive charge by replacing the native cysteine residue with an arginine or lysine residue. For example, a HB can be selected from the following peptides having the amino acid residue sequences: KRKKKGKGLGKKRDPCLRKYK (SEQ ID NO:1); KRKKKGKGLGKKRDPRLRKYK (SEQ ID NO:2) (also referred to as HB C16R); or KRKKKGKGLGKKRDPKLRKYK (SEQ ID NO:3) (also referred to as HB C16K), or functional variants, analogs or derivatives thereof.

Additionally, the HB portion of the composition may be repeated, optionally with a linker peptide connecting the HB peptides. Thus, for example, using SEQ ID NO: 2 as an exemplary HB portion, a therapeutic molecule can comprise or be linked to the following amino acids: KRKKKGKGLGKKRDPRL-RKYKGGGKRKKKGKGLGKKRDPRLRKYK (SEQ ID NO:4) or KRKKKGKGLGKKRDPRL-RKYKGGGKRKKKGKGLGKKRDPRL-RKYKGGGKRKKKGKGLGKK RDPRLRKYK (SEQ ID NO:5). Linker peptides commonly known to one of ordinary skill in the art are encompassed for use in the present invention, for example, such as those as disclosed herein. In some embodiments, a linker peptide comprises GGG. In some embodiments, a linker peptide comprises (GGGGS) (SEQ ID NO: 42).

In some embodiments, an active agent of a recombinant HB fusion protein can be selected from Neurotrophic factors, including Neurothrophins such as nerve growth factor (NGF), brain-derived neurotrophic factor (BDNF), neurotrophin-3 (NT-3), neurotrophin-4 (NT-4), Ciliary neurotrophic factor (CNTF), mesencephalic astrocyte-derived neurotrophic factor (MANF), or conserved dopamine neurotrophic factor (CDNF); Glial cell-line derived neurotrophic factor family ligands such as glial cell line-derived neurotrophic factor (GDNF), neurturin (NRTN), artemin (ARTN), or persephin (PSPN); Neuropoietic cytokines such as interleukin-6, interleukin-11, interleukin-27, leukaemia inhibitory factor, ciliary neurotrophic factor, cardiotrophin 1, neuropoietin, cardiotrophin-like cytokine, or Fibroblast Growth Factor 2; Anti-inflammatory cytokines including interleukin-4 and interleukin-10; Neuroprotection agents including Neuregulin-1 and Vascular endothelial growth factor (VEGF); or other therapeutic proteins such as Cerebrolysin® (FPF-1070), Growth differentiation factor 11 (GDF11), Stromal cell-derived factor 1 (SDF-1), Myostatin (growth differentiation factor 8 (GDF8)); Insulin-like Growth Factor 1 (IGF-1); Parathyroid hormone (PTH); Parathyroid hormone related peptide (PTHrP); Interleukin 1 receptor antagonist (IL-1RA); IL-1/IL-1RA chimerias, Fibroblast growth factor 18 (FGF-18); High-mobility group protein 2 (HMG-2, also known as High mobility group box 2 (HMGB2)); a therapeutic antibody or portion thereof, such as REMICADE® (infliximab, anti-TNF-α, Janssen Biotech, Horsham, Pa.), HUMIRA® (adalimumab, anti-TNF, Abbot Labs., N. Chicago, Ill.), ENBREL® (etanercept, recombinant anti-TNF protein, Amgen, Thousand Oaks, Calif.), or an anti-nerve growth factor antibody; Fibroblast growth factor 9 (FGF-9); Hepatocyte growth factor; TGFβ-superfamily proteins such as TGFβ, TGFβ3, BMP2, or BMP7; angiopoietin-like 3 (ANGPTL3), somatostatin (SST) or functional portions, variants, analogs, or derivatives of any of these.

In some embodiments, the therapeutic protein portion of the HB fusion is selected from IGF-1, PTH, PTHrP, IL-1RA, FGF-18, or functional portions, analogs, or derivatives thereof.

Another aspect of the present invention provides for a method of treating cartilage-related clinical conditions (e.g., damage or disease) comprising administering to a subject an effective amount of a recombinant fusion protein comprising HB-X, where X is a therapeutic protein or a portion thereof, wherein the therapeutic protein is selected from IGF-1, PTH, PTHrP, IL-1RA, FGF-18, an anti-nerve growth factor antibody, FGF-9, Hepatocyte growth factor, TGFβ, TGFβ3, BMP2, BMP7, or functional portions, analogs, or derivatives thereof.

In another particular embodiment, HB is fused to Glucocorticoid receptor, which facilitates targeted delivery of corticosteroids to the cartilage; the administration of which can be done concurrently or separately from administration of a corticosteroid.

In some embodiments, the cartilage condition is a articular cartilage defect including rupture or detachment, a meniscal defect including a partial or complete tear, Osteoarthritis, Traumatic cartilage rupture or detachment, Ankylosing spondylitis, Capsulitis, Psoriatic arthritis, Rheumatoid arthritis, Systemic lupus erythematosus, or X-linked hypophosphatemic rickets, or Juvenile idiopathic arthritis. Treatment of cartilage condition can be combined with other therapy as an adjunct to other surgical interventions for articular cartilage repair, meniscal repair, or ligament repair, for the purposes of both improving the repair and preventing development of osteoarthritis.

Another aspect of the present invention provides for treating a neurological condition (e.g., a disorder or disease) comprising administering to a subject an effective amount of a recombinant fusion protein comprising HB-X, where X is a therapeutic protein or a portion thereof, selected from nerve growth factor (NGF), brain-derived neurotrophic factor (BDNF), neurotrophin-3 (NT-3), neurotrophin-4 (NT-4), Ciliary neurotrophic factor (CNTF), mesencephalic astrocyte-derived neurotrophic factor (MANF), conserved dopamine neurotrophic factor (CDNF), glial cell line-derived neurotrophic factor (GDNF), neurturin (NRTN), artemin (ARTN), persephin (PSPN), interleukin-6, interleukin-11, interleukin-27, leukaemia inhibitory factor, ciliary neurotrophic factor, cardiotrophin 1, neuropoietin, cardiotrophin-like cytokine, FPF-1070, Fibroblast Growth Factor 2, Neuregulin-1, Vascular endothelial growth factor (VEGF), IGF or Insulin-like Growth Factor 1 (IGF-1).

The neurological condition can be selected from Alzheimer's disease, Parkinson's disease, Amyotrophic lateral sclerosis, Multiple sclerosis, Brain injury, Spinal cord injury, Peripheral nerve degeneration, Stroke, Huntington's disease, Pick's disease, Diabetic neuropathy, Frontotemporal dementia, Dementia with Lewy bodies, Corticobasal degeneration, Progressive supranuclear palsy, Prion disorders, Progressive supranuclear palsy, Multiple system atrophy, Hereditary spastic paraparesis, Spinocerebellar atrophies, Friedreich's ataxia, Amyloidoses, or Charcot Marie Tooth syndrome.

Another embodiment provides for the administration of a HB-X composition for the treatment of eye diseases such as Corneal ulcer, Corneal abrasion, Thygeson's superficial punctate keratopathy, Corneal neovascularization, Fuchs' dystrophy, Keratoconjunctivitis sicca, Chorioretinal inflammation, Chorioretinal scars, Choroidal degeneration, Hereditary choroidal dystrophy, Retinal detachment, Retinoschisis, Hypertensive retinopathy, Retinopathy of prematurity, Age-related macular degeneration, Retinal degeneration, Macular degeneration, Epiretinal membrane, Peripheral retinal degeneration, Hereditary retinal dystrophy, Retinitis pigmentosa, Xerophthalmia, or Retinal haemorrhage.

Another aspect of the present invention provides for a method of treating inflammation comprising administering to a subject an effective amount of a recombinant fusion protein comprising HB-X, where X is a therapeutic protein or a portion thereof, selected from TNF receptor 2, interleukin-4, or interleukin-10.

In another embodiment of the invention, the HB-X is provided in a sustained release vehicle, such as hyaluronic acid, to extend the release and physiological effect of the HB-X composition.

DESCRIPTION OF THE DRAWINGS

FIG. 5 shows a western blot using anti-IGF-1 antibody to detect the presence of IGF1 after incubation of cartilage explants with different HB-IGF-1 fusion variants, where the HB variants include C17K (SEQ ID NO:22); C17R (SEQ ID NO: 21), C17S (SEQ ID NO: 41), wild-type HB (SEQ ID NO: 20). FIG. 5 shows that IGF-1 fusion proteins comprising C17K (SEQ ID NO:22) or C17R (SEQ ID NO: 21) variants result in greater retention of the IGF-1 in the cartilage as compared to the C17S (SEQ ID NO: 41) and wild-type HB (SEQ ID NO: 1) HB variants.

FIG. 6 shows a western blot using anti-IGF-1 antibody from cartilage extracts purified by size exclusion chromatography to detect the yield of IGF1 after incubation of cartilage explants with HB-IGF1 fusion variants comprising either the C17R (SEQ ID NO: 21) or wild-type HB (SEQ ID NO: 20) HB peptide. FIG. 6 shows a significantly higher yield of IGF-1 from extracts incubated with HB(C17R)-IGF-1 fusion proteins C17R as compared to HB(WT)-IGF-1 fusion proteins.

FIG. 7 shows HB (C17R) allows superior yield of HB-IGF1 from inclusion bodies. FIG. 7 shows a western blot using anti-IGF-1 antibody from cartilage extracts purified from inclusion bodies to detect the yield of IGF1 after incubation of cartilage explants with HB-IGF1 fusion variants comprising either the C17R (SEQ ID NO: 21) (referred to as eHB) or wild-type HB (SEQ ID NO: 20) HB peptide. FIG. 7 shows a significantly higher yield of IGF-1 in induced and non-induced inclusion bodies obtained from with HB(C17R)-IGF-1 (eHB-IGF-1) fusion proteins as compared to extracts incubated HB(WT)-IGF-1 (wHB-IGF-1) fusion proteins.

FIG. 8 shows a western blot of the retention of IGF-1 in the spinal cord incubated with HB-IGF-1. Rat spinal cord tissue was incubated for 24 hours in medium with no additions (No IGF-1), 1 ug/ml IGF-1, or 1 ug/ml HB-IGF-1. After incubation, tissue was washed and either frozen immediately ("Day 0") or incubated for an additional 24 hours in fresh medium before collection to wash out the proteins ("Day 1"). Tissues were then analyzed by Western blotting with an anti-IGF1 antibody to detect the presence of IGF-1 or HB-IGF-1 remaining in the spinal cord tissue.

FIGS. 9A-9B show that retention of PTH in cartilage disks incubated with PTH-HB. Cartilage disks were incubated in medium with no added peptide ("No PTH"), parathyroid hormone 1-34 ("PTH"), or a fusion of parathyroid hormone 1-34 with an HB domain ("PTH-HB"). FIG. 9A shows the peptide control of amount of PTH or PTH-HB added to the cartilage disk explants. After 24 hours, cartilage discs were washed and returned to incubation in fresh medium in the absence of a peptide. FIG. 9B shows a western blot with an anti-PTH antibody in cartilage tissue extracts two days after washout, showing that PTH is only retained in the cartilage discs incubated with PTH-HB but not non-fused PTH.

DETAILED DESCRIPTION OF THE INVENTION

The present invention related to conjugation of a heparin-binding peptides (HB) peptide to an active agent (e.g., X) for selectively delivery of the active agent to a cell or tissue expressing proteoglycans. In some embodiments, the HB-active agent conjugate can be used to deliver the active agent to cells or tissues that express proteoglycans, for example, but not limited to cartilage, brain and spinal cord tissue, skin and subcutaneous tissue.

More specifically, some embodiments herein are directed to heparin-binding peptides (HB) of SEQ ID NO: 1-3 or SEQ ID NO: 20-22 fused to an active agent which is a therapeutic protein or a portion thereof, optionally by a linker peptide. Some embodiments, the active agent is a small molecule, and enable delivery of the small molecule to cells and tissues comprising proteoglycans, where a HB peptide of SEQ ID NO: 1-3 or SEQ ID NO: 20-22 can be conjugated to the small molecule by direct or indirect linkage (e.g., use of chemical linkers). In some embodiments, compositions comprising HB-X conjugates can be used for delivery of one or multiple different therapeutic proteins and agents to tissues an cells expressing proteoglycans.

An aspect of the present invention provides for a selective therapeutic composition comprising HB-$X_n$, or (HB-linker)$_n$-$X_n$, where HB is a heparin binding protein, X is an active agents such as a therapeutic protein or a portion thereof, or a therapeutic small molecule, and n is an integer of at least 1. In some embodiments, the composition is a recombinant fusion protein comprising a recombinant HB and the therapeutic protein (or portion thereof). Any combination of a HB peptide selected from the group of SEQ ID NO: 1-3 or 30-22 can be used in any combination of an active agent, with or without the presence of a linker protein, where the HB peptide can be located at the N- and/or C-terminus of the active agent, and there can be one or multiple HB peptide-linkers attached to the N- and/or C-terminus of the active agent. For example, in some embodiments, the fusion or conjugate can comprise (HB-linker)$_n$-$X_m$-(linker-HB)$_o$, where n, m, and o are integers, and m is at least one and n+o is at least one.

In some embodiments, the components of the composition can be placed in order, relative to the N-terminus of the HB portion of the composition: HB-X, X-HB, HB-linker-X, (HB-linker)$_2$-X, X-linker-HB, X-HB-X, HB$_n$-X-HB$_n$, (HB-linker)$_n$-X-(linker-HB)$_n$, HB-X-HB-X, etc. Additionally, the composition can comprise a mixture of HB-X constructs, wherein X represents different proteins or small molecules (i.e., a composition comprising HB-$X^1$ and HB-$X^2$, etc.). An example linker is a peptide having the amino acids GGG.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims. Unless defined otherwise, all technical and scientific terms used herein have the same meaning as those commonly understood to one of ordinary skill in the art to which this invention pertains. All Gene IDs refer to human genes, unless otherwise noted, available in the National Center for Biotechnology Information (NCBI) database.

As used herein and in the claims, the singular forms include the plural reference and vice versa unless the context clearly indicates otherwise. The term "or" is inclusive unless modified, for example, by "either." Other than in the operating examples, or where otherwise indicated, all numbers expressing quantities of ingredients or reaction conditions used herein should be understood as modified in all instances by the term "about." It is further to be understood that all base sizes or amino acid sizes, and all molecular weight or molecular mass values, given for nucleic acids or polypeptides are approximate, and are provided for description.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The present invention provides for selective delivery of active agents and therapeutic moieties, e.g. proteins or small molecules, to particular tissues to which heparin binding proteins associate. More specifically, the present embodiments provide for novel proteinaceous heparin-binding motifs (HB) that are linked to or fused to a therapeutic moiety, such as a small molecule, or a cytokine or growth factor or functional portion thereof.

DEFINITIONS

Figure 1:
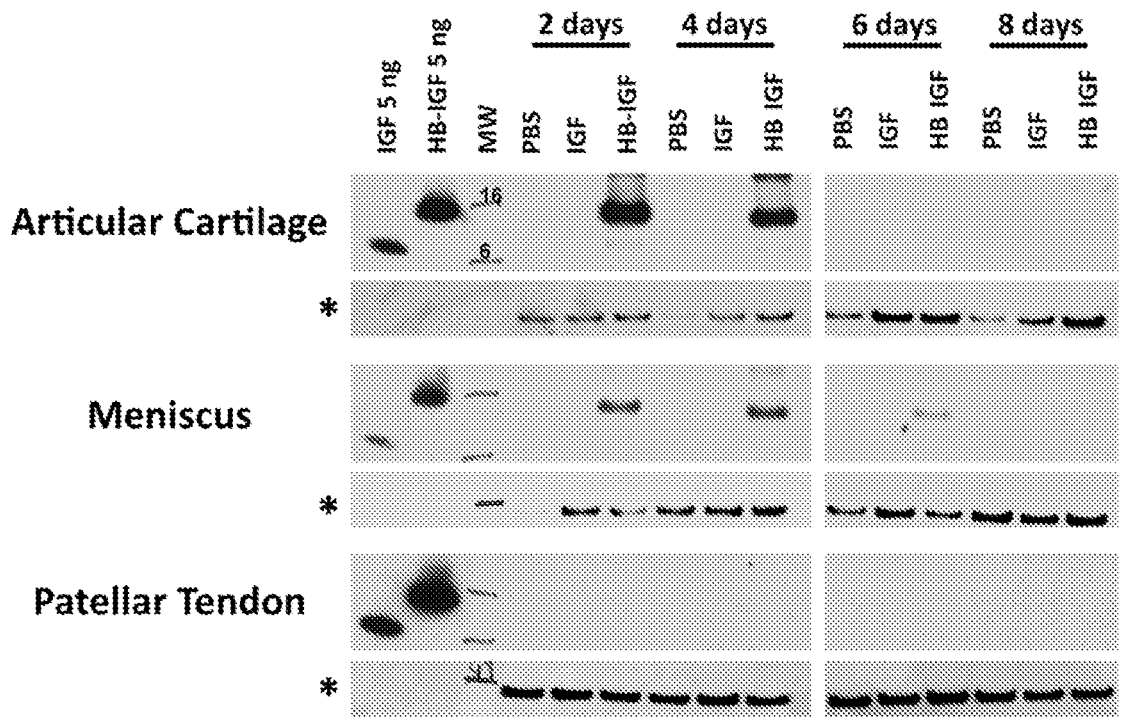
FIG. 1 provides data showing long term retention of an embodiment of HB-IGF-1 after intra-articular injection. Western blot analysis was performed for retained IGF-1 or HB-IGF-1 in rat articular cartilage, meniscus, or patellar tendon at 2, 4, 6, and 8 days after intra-articular injection of either IGF-1, HB-IGF-1, or PBS.

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

The term "protein" may be used interchangeably with "polypeptide" to refer to a polymer of amino acid residues linked by peptide bonds. Typically, a protein or polypeptide has a minimum length of at least 25 amino acids. The term "polypeptide" and "protein" can encompass a multimeric protein, e.g., a protein containing more than one domain or subunit. The term "peptide" as used herein typically refers to a peptide bond-linked amino acid polymer containing less than 25 amino acids, e.g., between about 4 amino acids and about 25 amino acids in length. Proteins and peptides can be composed of linearly arranged amino acids linked by peptide bonds, whether produced biologically, recombinantly, or synthetically and whether composed of naturally occurring or non-naturally occurring amino acids, are included within this definition. Both full-length proteins and fragments thereof greater than 25 amino acids are encompassed by the definition of protein. The terms also include polypeptides that have co-translational (e.g., signal peptide cleavage) and post-translational modifications of the polypeptide, such as, for example, disulfide-bond formation, glycosylation, acetylation, phosphorylation, lipidation, proteolytic cleavage (e.g., cleavage by metalloproteases), and the like. Furthermore, as used herein, a "polypeptide" refers to a protein that includes modifications, such as deletions, additions, and substitutions (generally conservative in nature as would be known to a person in the art) to the native sequence, as long as the protein maintains the desired activity. These modifications can be deliberate, as through site-directed mutagenesis, or can be accidental, such as through mutations of hosts that produce the proteins, or errors due to PCR amplification or other recombinant DNA methods. Polypeptides or proteins are composed of linearly arranged amino acids linked by peptide bonds, but in contrast to peptides, has a well-defined conformation. Proteins, as opposed to peptides, generally consist of chains of 25 or more amino acids. For the purposes of the present invention, the term "peptide" as used herein typically refers to a sequence of amino acids of made up of a single chain of D- or L-amino acids or a mixture of D- and L-amino acids joined by peptide bonds. Generally, peptides contain at least two amino acid residues and are less than about 25 amino acids in length.

It will be appreciated that proteins, polypeptides, or peptides often contain amino acids other than the 20 amino acids commonly referred to as the 20 naturally occurring amino acids (e.g., synthetic non-native amino acids), and that many amino acids, including the terminal amino acids, can be modified in a given polypeptide, either by natural processes such as glycosylation and other post-translational modifications, or by chemical modification techniques which are well known in the art. Known modifications which can be present in polypeptides of the present invention include, but are not limited to, acetylation, acylation, ADP-ribosylation, amidation, covalent attachment of flavin, covalent attachment of a heme moiety, covalent attachment of a polynucleotide or polynucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formulation, gamma-carboxylation, glycation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

The incorporation of non-natural amino acids, including synthetic non-native amino acids, substituted amino acids, or one or more D-amino acids into the HB peptides and/or active agent peptides or proteins (or other components of the composition) is desirable in certain situations. D-amino acid-containing peptides exhibit increased stability in vitro or in vivo compared to L-amino acid-containing forms. Thus, the construction of peptides incorporating D-amino acids can be particularly useful when greater in vivo or intracellular stability is desired or required. More specifically, D-peptides are resistant to endogenous peptidases and proteases, thereby providing better oral trans-epithelial and transdermal delivery of linked drugs and conjugates, improved bioavailability of membrane-permanent complexes (see below for further discussion), and prolonged intravascular and interstitial lifetimes when such properties are desirable. The use of D-isomer peptides can also enhance transdermal and oral trans-epithelial delivery of linked drugs and other cargo molecules. Additionally, D-peptides cannot be processed efficiently for major histocompatibility complex class II-restricted presentation to T helper cells, and are therefore less likely to induce humoral immune responses in the whole organism. Peptide conjugates can therefore be constructed using, for example, D-isomer forms of cell penetrating peptide sequences, L-isomer forms of cleavage sites, and D-isomer forms of therapeutic peptides. In some embodiments, a HB-fusion protein comprises D- and/or L-amino acid residues, as use of naturally occurring L-amino acid residues has the advantage that any break-down products should be relatively non-toxic to the cell or organism.

In yet a further embodiment, HB-X can be a retro-inverso peptides. A "retro-inverso peptide" refers to a peptide with a reversal of the direction of the peptide bond on at least one position, i.e., a reversal of the amino- and carboxy-termini with respect to the side chain of the amino acid. Thus, a retro-inverso analogue has reversed termini and reversed direction of peptide bonds while approximately maintaining the topology of the side chains as in the native peptide sequence. The retro-inverso peptide can contain L-amino acids or D-amino acids, or a mixture of L-amino acids and D-amino acids, up to all of the amino acids being the D-isomer. Partial retro-inverso peptide analogues are polypeptides in which only part of the sequence is reversed and replaced with enantiomeric amino acid residues. Since the retro-inverted portion of such an analogue has reversed amino and carboxyl termini, the amino acid residues flanking the retro-inverted portion are replaced by side-chain-analogous α-substituted geminal-diaminomethanes and malonates, respectively. Retro-inverso forms of cell penetrating peptides have been found to work as efficiently in translocating across a membrane as the natural forms. Synthesis of retro-inverso peptide analogues are described in Bonelli, F. et al., Int J Pept Protein Res. 24(6):553-6 (1984); Verdini, A and Viscomi, G. C., J. Chem. Soc. Perkin Trans. 1:697-701 (1985); and U.S. Pat. No. 6,261,569, which are incorporated herein in their entirety by reference. Processes for the solid-phase synthesis of partial retro-inverso peptide analogues have been described (EP 97994-B) which is also incorporated herein in its entirety by reference.

The term "variant" refers to a polypeptide or nucleic acid that differs from the naturally occurring polypeptide or nucleic acid by one or more amino acid or nucleic acid deletions, additions, substitutions or side-chain modifications, yet retains one or more specific functions or biological activities of the naturally occurring molecule Amino acid substitutions include alterations in which an amino acid is replaced with a different naturally-occurring or a non-conventional amino acid residue. Such substitutions may be classified as "conservative," in which case an amino acid residue contained in a polypeptide is replaced with another naturally occurring amino acid of similar character either in relation to polarity, side chain functionality or size. Substitutions encompassed by variants as described herein may also be "non-conservative," in which an amino acid residue which is present in a peptide is substituted with an amino acid having different properties (e.g., substituting a charged or hydrophobic amino acid with alanine), or alternatively, in which a naturally-occurring amino acid is substituted with a non-conventional amino acid. Also encompassed within the term "variant," when used with reference to a polynucleotide or polypeptide, are variations in primary, secondary, or tertiary structure, as compared to a reference polynucleotide or polypeptide, respectively (e.g., as compared to a wild-type polynucleotide or polypeptide).

Variants can include conservative or non-conservative amino acid changes, as described below. Polynucleotide changes can result in amino acid substitutions, additions, deletions, fusions and truncations in the polypeptide encoded by the reference sequence. Variants can also include insertions, deletions or substitutions of amino acids, including insertions and substitutions of amino acids and other molecules) that do not normally occur in the peptide sequence that is the basis of the variant, for example but not limited to insertion of ornithine which do not normally occur in human proteins. "Conservative amino acid substitutions" result from replacing one amino acid with another that has similar structural and/or chemical properties. Conservative substitution tables providing functionally similar amino acids are well known in the art. For example, the following six groups each contain amino acids that are conservative substitutions for one another: (1) Alanine (A), Serine (S), Threonine (T); (2) Aspartic acid (D), Glutamic acid (E); (3) Asparagine (N), Glutamine (Q); (4) Arginine (R), Lysine (K); (5) Isoleucine (I), Leucine (L), Methionine (M), Valine (V); and (6) Phenylalanine (F), Tyrosine (Y), Tryptophan (W). See, e.g., Creighton, PROTEINS (W.H. Freeman & Co., 1984). The choice of conservative amino acids may be selected based on the location of the amino acid to be substituted in the peptide, for example if the amino acid is on the exterior of the peptide and exposed to solvents, or on the interior and not exposed to solvents. In some embodiments, polypeptides including non-conservative amino acid substitutions are also encompassed within the term "variants." As used herein, the term "non-conservative" substitution refers to substituting an amino acid residue for a different amino acid residue that has different chemical properties. Non-limiting examples of non-conservative substitutions include aspartic acid (D) being replaced with glycine (G); asparagine (N) being replaced with lysine (K); and alanine (A) being replaced with arginine (R). Selection of such conservative and non-conservative amino acid substitutions is within the skill of one of ordinary skill in the art.

The term "derivative" refers to proteins or peptides which have been chemically modified, for example by ubiquitination, labeling, pegylation (derivatization with polyethylene glycol) or addition of other molecules. A molecule is also a "derivative" of another molecule when it contains additional chemical moieties not normally a part of the molecule. Such moieties can improve the molecule's solubility, absorption, biological half-life, etc. The moieties can alternatively decrease the toxicity of the molecule, or eliminate or attenuate an undesirable side effect of the molecule, etc. Moieties capable of mediating such effects are disclosed in REMINGTON'S PHARMACEUTICAL SCIENCES (21st ed., Tory, ed., Lippincott Williams & Wilkins, Baltimore, Md., 2006).

The term "functional" when used in conjunction with "derivative" or "variant" refers to a protein molecule which possesses a biological activity that is substantially similar to a biological activity of the entity or molecule of which it is a derivative or variant. "Substantially similar" in this context means that the biological activity of a polypeptide, is at least 50% as active as a reference, e.g., a corresponding wild-type polypeptide, e.g., at least 60% as active, 70% as active, 80% as active, 90% as active, 95% as active, 100% as active or even higher (i.e., the variant or derivative has greater activity than the wild-type), e.g., 110% as active, 120% as active, or more, inclusive.

The term "functional portion" or "functional fragment" refers to a portion of the native molecule (e.g., the native protein or receptor binding moiety of a chemical entity) that mediates the same effect as the full-length molecule, e.g., stimulates a cell response such as growth or affects a signal or signal cascade related to a desired physiological effect.

The term "fragment" of a peptide, polypeptide or molecule as used herein refers to any contiguous polypeptide subset of the molecule. The term "protein fragment" as used herein includes both synthetic and naturally-occurring amino acid sequences derivable from the naturally occurring amino acid sequence, e.g., a naturally occurring active agent which is a protein, or HB (SEQ ID NO:1) or a variant thereof (e.g., SEQ ID NO: 2 or SEQ ID NO: 3). The protein is said to be "derivable from the naturally-occurring amino acid sequence" if it can be obtained by fragmenting the naturally-occurring protein, or if it can be synthesized based upon a knowledge of the sequence of the naturally occurring amino acid sequence or of the genetic material (DNA or RNA) which encodes this sequence. Accordingly, a "fragment" of a molecule, is meant to refer to any polypeptide subset of the molecule. Fragments of HB which have the activity of HB peptide variants of SEQ ID NO: 2 or SEQ ID NO:3 as disclosed herein and which are soluble are also encompassed for use in the present invention.

For example functional fragments of SEQ ID NO: 2 or SEQ ID NO:3 useful in the methods as disclosed herein have at least 30% the activity as that of a polypeptide of SEQ ID NO: 2 or SEQ NO: 3 in vivo. Stated another way, a fragment of SEQ ID NO: 2 or SEQ ID NO:3 is any fragment which, alone or fused to an active agent can result in at least 30% of the same activity as compared to SEQ ID NO: 2 or SEQ ID NO:3 to retain the HB-fusion protein in the tissue after 24 hours after wash-out as disclosed herein when a HB fusion protein comprising SEQ ID NO: 2 or SEQ ID NO:3 is incubated with a cartilage explant or spinal cord explant (as disclosed in the Examples). A "fragment" can be at least about 6, at least about 9, at least about 15, at least about 20, at least about 30, least about 40, at least about 50, at least about 100, at least about 250, at least about 300 nucleic or amino acids, and all integers in between. Exemplary fragments include C-terminal truncations, N-terminal truncations, or truncations of both C- and N-terminals (e.g., deletions of, for example, at least 1, at least 2, at least 3, at least 4, at least 5, at least 8, at least 10, at least 15, at least 20, at least 25, at least 40, at least 50, at least 75, at least 100 or more amino acids deleted from the N-termini, the C-termini, or both). One of ordinary skill in the art can create such fragments by simple deletion analysis. Such a fragment of SEQ ID NO: 2 or SEQ ID NO:3 can be, for example, 1, 2, 3, 4, 5, 6, 7, 8, 9 or 10 amino acids or more than 10 amino acids, deleted from the N-terminal and/or C-terminal of SEQ ID NO: 2 or SEQ ID NO:3, respectively. In some embodiments, by sequentially deleting N- and/or C-terminal amino acids from SEQ ID NO: 2 or SEQ ID NO:3, and assessing the function of the resulting peptide fragment, alone or fused to an active agent can identify a functional fragment of HB for use in the present invention. One can create functional fragments with multiple smaller fragments. These can be attached by bridging peptide linkers. One can readily select linkers to maintain wild type conformation. One of ordinary skill in the art can easily assess the function of an HB-X conjugate to retain in the tissue and cause a biological effect by the active agent X (as disclosed in the Examples) as compared to a HB-fusion protein comprising SEQ ID NO: 2 or SEQ ID NO: 3. Using an in vivo assay such as the cartilage assay as disclosed in the Examples, if the HB peptide fragment has at least 30% of the biological activity of the HB corresponding to SEQ ID NO: 2 or SEQ ID NO: 3 as disclosed herein, then the HB peptide fragment of an HB(fragment)-X fusion protein is considered a valid HB-fragment and can used in fusion proteins and methods as disclosed herein. In some embodiments, a fragment of SEQ ID NO: 2 or SEQ ID NO:3 can be less than 20, or less than 15 or less than 10, or less than 5 amino acids of SEQ ID NO: 2 or SEQ ID NO:3. However, as stated above, the fragment must be at least 4 amino acids, at least about 9, at least about 15, at least about 20, at least about 30, at least about 40, at least about 50, at least about 100, at least about 250, at least about 500 nucleic acids or amino acids, or any integers in between.

The term "wild type" refers to the naturally-occurring, normal polynucleotide sequence encoding a protein, or a portion thereof, or protein sequence, or portion thereof, respectively, as it normally exists in vivo.

The term "mutant" refers to an organism or cell with any change in its genetic material, in particular a change (i.e., deletion, substitution, addition, or alteration) relative to a wild-type polynucleotide sequence or any change relative to a wild-type protein sequence. The term "variant" may be used interchangeably with "mutant". Although it is often assumed that a change in the genetic material results in a change of the function of the protein, the terms "mutant" and "variant" refer to a change in the sequence of a wild-type protein regardless of whether that change alters the function of the protein (e.g., increases, decreases, imparts a new function), or whether that change has no effect on the function of the protein (e.g., the mutation or variation is silent).

The term "substantially similar," when used in reference to a variant of a protein or peptide or a functional derivative thereof, as compared with the original protein, means that a particular subject sequence varies from the sequence of the polypeptide by one or more substitutions, deletions, or additions, but retains at least 50%, or higher, e.g., at least 60%, 70%, 80%, 90% or more, inclusive, of the function of the protein. In determining polynucleotide sequences, all subject polynucleotide sequences capable of encoding substantially similar amino acid sequences are considered to be substantially similar to a reference polynucleotide sequence, regardless of differences in codon sequence. A nucleotide sequence is "substantially similar" to a given nucleic acid sequence if: (a) the given polynucleotide nucleotide hybridizes to the coding regions of the native polynucleotide, or (b) the given polynucleotide is capable of hybridization to the native polynucleotide under moderately stringent conditions and its encoded protein has biological activity similar to the native protein; or (c) the sequence of polynucleotide are degenerate as a result of the genetic code relative to the nucleotide sequences defined in (a) or (b). Substantially similar proteins will typically be greater than about 80% similar to the corresponding sequence of the native protein.

The terms "homologous" or "homologues" are used interchangeably, and when used to describe a polynucleotide or polypeptide, indicate that two polynucleotides or polypeptides, or designated sequences thereof, when optimally aligned and compared, for example using BLAST, version 2.2.14 with default parameters for an alignment are identical, with appropriate nucleotide insertions or deletions or amino-acid insertions or deletions, typically in at least 70% of the nucleotides of the nucleotides for high homology. For a polypeptide, there should be at least 30% of amino acid identity in the polypeptide, or at least 50% for higher homology. The term "homolog" or "homologous" as used herein also refers to homology with respect to structure. Determination of homologs of genes or polypeptides can be easily ascertained by the skilled artisan. When in the context with a defined percentage, the defined percentage homology means at least that percentage of amino acid similarity. For example, 85% homology refers to at least 85% of amino acid similarity.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Where necessary or desired, optimal alignment of sequences for comparison can be conducted by any variety of approaches, as these are well-known in the art.

The term "heterologous" in reference to nucleic acid sequences, proteins or polypeptides, means that these molecules are not naturally occurring in that cell. For example, the nucleic acid sequence coding for a fusion protein described herein that is inserted into a cell, e.g. in the context of a protein expression vector, is a heterologous nucleic acid sequence.

The term "agent" or "compound" as used herein refers to a chemical entity or biological product, or combination of chemical entities or biological products, administered to a subject to treat or prevent or control a disease or condition. The chemical entity or biological product is preferably, but not necessarily a low molecular weight compound, but may also be a larger compound, or any organic or inorganic molecule, including modified and unmodified nucleic acids such as antisense nucleic acids, RNAi, such as siRNA or shRNA, peptides, peptidomimetics, receptors, ligands, and antibodies, aptamers, polypeptides, nucleic acid analogues or variants thereof. For example, an agent can be an oligomer of nucleic acids, amino acids, or carbohydrates including, but not limited to proteins, peptides, oligonucleotides, ribozymes, DNAzymes, glycoproteins, RNAi agents (e.g., siRNAs), lipoproteins, aptamers, and modifications and combinations thereof. In some embodiments, an active agent is a nucleic acid, e.g., miRNA or a derivative or variant thereof. In some embodiments, an HB-X conjugate that comprises a nucleic acid agent, e.g., a RNAi or miRNA agent can be joined (e.g., conjugated) to HB peptide by means of a linker moiety can allow the miRNA or RNAi agent to interact with the DNA. In some embodiments, the linker moiety is a reversible moiety, e.g., miRNA or RNAi agent can be released from the HB peptide at the location of the target cell or tissue.

As used herein, the term "fused" means that at least one protein or peptide is physically associated with a second protein or peptide. In some embodiments, fusion is typically a covalent linkage, however, other types of linkages are encompassed in the term "fused" include, for example, linkage via an electrostatic interaction, or a hydrophobic interaction and the like. Covalent linkage can encompass linkage as a fusion protein or chemically coupled linkage, for example via a disulfide bound formed between two cysteine residues.

As used herein, the term "fusion polypeptide" or "fusion protein" means a protein created by joining two or more polypeptide sequences together. The fusion polypeptides encompassed in this invention include translation products of a chimeric gene construct that joins the DNA sequences encoding the HB peptide or mutants thereof, with the DNA sequence encoding a second polypeptide to form a single open-reading frame. In other words, a "fusion polypeptide" or "fusion protein" is a recombinant protein of two or more proteins which are joined by a peptide bond or via several peptides. The fusion protein may also comprise a peptide linker between the HB peptide and the active agent, e.g., a therapeutic peptide or polypeptide of the fusion protein.

In some embodiments, fusion proteins can be produced, for example, by a nucleic acid sequence encoding one protein is joined to the nucleic acid encoding another protein such that they constitute a single open-reading frame that can be translated in the cells into a single polypeptide harboring all the intended proteins. The order of arrangement of the proteins can vary. As a non-limiting example, the nucleic acid sequence encoding the HB peptide is fused in frame to an end, either the 5' or the 3' end, of a gene encoding a first fusion partner (e.g., X), such as a therapeutic protein or peptide. In this manner, on expression of the gene, the HB peptide is functionally expressed and fused to the N-terminal or C-terminal end of X (e.g., the therapeutic peptide or protein). In certain embodiments, modification of the polypeptide probe is such that the functionality of the HB peptide remains substantially unaffected in terms of its biological activity by fusion to the first fusion partner X, such as a therapeutic peptide. In some embodiments, a nucleic acid construct encoding a HB-X fusion protein also has a nucleic acid sequence which encodes a linker, which is located between nucleic acid encoding the HB peptide and the nucleic acid sequence encoding X (e.g., the therapeutic peptide or protein). In some embodiments, the HB-X fusion protein is configures such that the functionality of the HB peptide or X (e.g., the therapeutic protein or peptide) is not significantly compromised by the fusion.

As used herein, the term "associated with" means that one entity is in physical association or contact with another. Thus, a HB peptide "associated with" an active agent can be either covalently or non-covalently joining of the HB peptide to the active agent. The association can be mediated by a linker moiety, particularly where the association is covalent. The term "association" or "interaction" or "associated with" are used interchangeably herein and as used in reference to the association or interaction of a HB peptide with the active agent, either by a direct linkage or an indirect linkage.

As used herein, the term "conjugate" or "conjugation" or "linked" as used herein refers to the attachment of two or more entities to form one entity. A conjugate encompasses both peptide-small molecule conjugates as well as peptide-protein/peptide conjugates. For example, the methods of the present invention provide conjugation of a HB peptide joined with another entity, for example an active agent, e.g., a moiety such as a therapeutic protein/peptide or small molecule. As disclosed herein, the attachment can be by means of linkers, chemical modification, peptide linkers, chemical linkers, covalent or non-covalent bonds, or protein fusion or by any means known to one skilled in the art. The joining can be permanent or reversible. In some embodiments, several linker molecules (chemical or peptide linkers) can be included in order to take advantage of desired properties of each linker and each protein or molecule in the conjugate. Flexible linkers and linkers that increase the solubility of the conjugates are contemplated for use alone or with other linkers as disclosed herein. Peptide linkers can be linked by expressing DNA encoding the linker to one or more proteins in the conjugate. Linkers can be acid cleavable, photocleavable and heat sensitive linkers. Methods for conjugation are well known by persons skilled in the art and are encompassed for use in the present invention.

Alternatively, two or more entities that are joined can be linked by indirect linkage. An indirect linkage includes an association between a HB peptide and an active agent, wherein the HB peptide and the active agent are attached via a "linker moiety", e.g., they are not directly linked. A direct linkage includes any linkage wherein a linker moiety is not required. In one embodiment, a direct linkage includes a chemical or a physical interaction wherein the two moieties, i.e. the targeting moiety and binding moiety interact such that they are attracted to each other. Examples of direct interactions include covalent interactions, non-covalent interactions, hydrophobic/hydrophilic, ionic (e.g., electrostatic, coulombic attraction, ion-dipole, charge-transfer), Van der Waals, or hydrogen bonding, and chemical bonding, including the formation of a covalent bond. Accordingly, in one embodiment, a targeting moiety, such as an antibody of fragment thereof and the binding moiety are not linked via a linker, e.g., they are directly linked. In a further embodiment, a targeting moiety and the binding moiety are electrostatically associated with each other.

The term "conjugated" refers to the attachment of at least two entities joined together. The joining of the two entities can be direct (e.g., via covalent or non-covalent bonds) or indirect (e.g., via linkers etc.)

The term "linker" refers to any means, entity or moiety used to join two or more entities. For example a HB peptide as disclosed herein can be joined to an active agent X (e.g., a therapeutic protein or peptide) using a linker moiety. A linker can be a covalent linker or a non-covalent linker. Examples of covalent linkers include covalent bonds or a linker moiety covalently attached to one or more of the proteins to be linked. The linker can also be a non-covalent bond, e.g. an organometallic bond through a metal center such as platinum atom. For covalent linkages, various functionalities can be used, such as amide groups, including carbonic acid derivatives, ethers, esters, including organic and inorganic esters, amino, urethane, urea and the like. To provide for linking, the effector molecule and/or the probe can be modified by oxidation, hydroxylation, substitution, reduction etc. to provide a site for coupling. Linkers can be acid cleavable, photocleavable and heat sensitive linkers. Methods for conjugation are well known by persons skilled in the art and are encompassed for use in the present invention. In some embodiments, a linker moiety to attach a HB peptide to a nucleic acid is a cyclopropapyrroloindole cross-linker. Linker moieties include, but are not limited to, chemical linker moieties, or for example a peptide linker moiety. In some embodiments, a linker between a HB peptide and an active agent or a peptide linker can be formed by reacting the polymer and a linker selected e.g., from the group consisting of p-nitrophenyl chloroformate, carbonyldiimidazole(CDI), N,N'-disuccinimidyl carbonate(DSC), cis-aconitic anhydride, and a mixture of these compounds. It will be appreciated that modification which do not significantly decrease the function of the HB peptide as disclosed herein or the active agent (e.g., therapeutic protein or peptide) are preferred.

The term "recombinant" when used to describe a nucleic acid molecule, means a polynucleotide of genomic, cDNA, viral, semisynthetic, and/or synthetic origin, which, by virtue of its origin or manipulation, is not associated with all or a portion of the polynucleotide sequences with which it is associated in nature. The term recombinant as used with respect to a peptide, polypeptide, protein, or recombinant fusion protein, means a polypeptide produced by expression from a recombinant polynucleotide. The term recombinant as used with respect to a host cell means a host cell into which a recombinant polynucleotide has been introduced. Recombinant is also used herein to refer to, with reference to material (e.g., a cell, a nucleic acid, a protein, or a vector) that the material has been modified by the introduction of a heterologous material (e.g., a cell, a nucleic acid, a protein, or a vector).

The term "vectors" refers to a nucleic acid molecule capable of transporting or mediating expression of a heterologous nucleic acid to which it has been linked to a host cell; a plasmid is a species of the genus encompassed by the term "vector." The term "vector" typically refers to a nucleic acid sequence containing an origin of replication and other entities necessary for replication and/or maintenance in a host cell. Vectors capable of directing the expression of genes and/or nucleic acid sequence to which they are operatively linked are referred to herein as "expression vectors". In general, expression vectors of utility are often in the form of "plasmids" which refer to circular double stranded DNA molecules which, in their vector form are not bound to the chromosome, and typically comprise entities for stable or transient expression or the encoded DNA. Other expression vectors that can be used in the methods as disclosed herein include, but are not limited to plasmids, episomes, bacterial artificial chromosomes, yeast artificial chromosomes, bacteriophages or viral vectors, and such vectors can integrate into the host's genome or replicate autonomously in the particular cell. A vector can be a DNA or RNA vector. Other forms of expression vectors known by those skilled in the art which serve the equivalent functions can also be used, for example self-replicating extra-chromosomal vectors or vectors which integrates into a host genome. Preferred vectors are those capable of autonomous replication and/or expression of nucleic acids to which they are linked.

The terms "subject" and "individual" are used interchangeably herein, and refer to an animal, for example a human, to whom treatment, including prophylactic treatment, with the pharmaceutical composition according to the present invention, is provided. The term "subject" as used herein refers to human and non-human animals. The term "non-human animals" and "non-human mammals" are used interchangeably herein includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment, the subject is human. In another embodiment, the subject is an experimental animal or animal substitute as a disease model. The term does not denote a particular age or sex. Thus, adult and newborn subjects, as well as fetuses, whether male or female, are intended to be covered. Examples of subjects include humans, dogs, cats, cows, goats, and mice. The term subject is further intended to include transgenic species.

The term "tissue" is intended to include intact cells, blood, blood preparations such as plasma and serum, bones, joints, cartilage, neuronal tissue (brain, spinal cord and neurons), muscles, smooth muscles, and organs.

The term "disease" or "disorder" is used interchangeably herein, refers to any alternation in state of the body or of some of the organs, interrupting or disturbing the performance of the functions and/or causing symptoms such as discomfort, dysfunction, distress, or even death to the person afflicted or those in contact with a person. A disease or disorder can also related to a distemper, ailing, ailment, amlady, disorder, sickness, illness, complaint, inderdisposion, affection.

The term "cartilage-related condition" or "cartilage-related clinical condition" refers to any defect in the articular cartilage. The term encompasses, but is not limited to, a rupture or detachment of the cartilage, a meniscal defect including a partial or complete tear, damage or a disease effecting the meniscus and/or patella, osteoarthritis (referred to herein as "OA"), including knee, finger, wrist, hip, ankle, elbow, toe, shoulder, and spinal osteoarthritis, traumatic cartilage rupture or detachment, ankylosing spondylitis, capsulitis, psoriatic arthritis, rheumatoid arthritis (RA), systemic lupus erythematosus, juvenile idiopathic arthritis, Chondropathy, Chondrosarcoma, Chondromalacia, Polychondritis, Relapsing Polychondritis, Slipped epiphysis, Osteochondritis Dissecans, Chondrodysplasia, Costochondritis, X-linked hypophosphatemic rickets, Osteochondroma, Chondrosarcoma (malignant), Osteoarthritis Susceptibility (types 1-6), Spondylosis, Osteochondroses, Primary chondrosarcoma, Chondrodysplasia, Tietze syndrome, Dermochondrocorneal dystrophy of Francois, Epiphyseal dysplasia, multiple, (types 1-5), Ossified Ear cartilages with Mental deficiency, Muscle Wasting and Bony Changes, Carpotarsal osteochondromatosis, Achondroplasia, Chondrocalcinosis (types 1-2), Genochondromatosis, Chondrodysplasia (disorder of sex development), Chondroma, Achondrogenesis (types 1A, 1B, 2, 3, 4, Langer-Saldino Type), Type II Achondrogenesis-Hypochondrogenesis, Atelosteogenesis, (type 1, 2 and III), Pyknoachondrogenesis, Pseudoachondroplasia, Osteoarthropathy of fingers, familial, Diastrophic dysplasia, Dyschondrosteosis—nephritis, Coloboma of Alar-nasal cartilages with telecanthus, Alar cartilages hypoplasia—coloboma—telecanthus, Pierre Robin syndrome—fetal chondrodysplasia, Dysspondyloenchondromatosis, Achondroplasia regional—dysplasia abdominal muscle, Osteochondritis Dissecans, Familial Articular Chondrocalcinosis, Tracheobronchomalacia, Chondritis, Dyschondrosteosis, Maffucci Syndrome, Jequier-Kozlowski-skeletal dysplasia, Chondrodystrophy, Cranio osteoarthropathy, Tietze's syndrome, Hip dysplasia—enchondromata—enchondromata, Bessel-Hagen disease, Chondromatosis (benign), Enchondromatosis (benign), chondrocalcinosis due to apatite crystal deposition, Meyenburg-Altherr-Uehlinger syndrome, Enchondromatosis-dwarfism-deafness, Astley-Kendall syndrome, Synovial osteochondromatosis, Chondrocalcinosis familial articular, Severe achondroplasia with developmental delay and acanthosis nigricans, Chondrocalcinosis, Keutel syndrome, Stanescu syndrome, Fibrochondrogenesis, Hypochondroplasia, A "composition" or "pharmaceutical composition" are used interchangeably herein refers to a composition that usually contains an excipient, such as a pharmaceutically acceptable carrier that is conventional in the art and that is suitable for administration to a HB-X conjugate to a tissue or subject. In addition, compositions for topical (e.g., oral mucosa, respiratory mucosa) and/or oral administration can form solutions, suspensions, tablets, pills, capsules, sustained-release formulations, oral rinses, or powders, as known in the art and described herein. The compositions also can include stabilizers and preservatives. For examples of carriers, stabilizers and adjuvants, University of the Sciences in Philadelphia (2005) Remington: The Science and Practice of Pharmacy with Facts and Comparisons, 21st Ed.

As used herein, the terms "treat," "treating," and "treatment" refer to the alleviation or measurable lessening of one or more symptoms or measurable markers of a disease or disorder; while not intending to be limited to such, disease or disorders of particular interest include autoimmune diseases and myositis. Measurable lessening includes any statistically significant decline in a measurable marker or symptom. In some embodiments, treatment is prophylactic treatment.

The term "therapeutically effective amount" refers to an amount effective, at dosages and for periods of time necessary, to achieve the desired therapeutic result, e.g., a diminishment or prevention of effects associated with various disease states or conditions, such as reduce a symptom of an autoimmune disease in the subject. The term "therapeutically effective amount" refers to an amount of an HB-X conjugate as disclosed herein effective to treat or prevent a disease or disorder in a mammal, preferably a human. A therapeutically effective amount of a HB-X conjugate can vary according to factors such as the disease state, age, sex, and weight of the subject, and the ability of the therapeutic compound X to elicit a desired response in the subject. A therapeutically effective amount is also one in which any toxic or detrimental effects of the therapeutic agent are outweighed by the therapeutically beneficial effects. In some embodiments, a therapeutically effective amount is an 'effective amount", which as used herein refers to the amount of therapeutic agent of pharmaceutical composition to alleviate at least one or some of the symptoms of the disease or disorder. An "effective amount" for purposes herein is thus determined by such considerations as are known in the art and is the amount to achieve improvement including, but not limited to, improved survival rate or more rapid recovery, or improvement or elimination of at least one symptom and other indicator of the disease being treated which are appropriate measures by those skilled in the art. It should be noted that HB-X fusion proteins as disclosed herein can be administered as a pharmaceutically acceptable salt and can be administered alone or as an active ingredient in combination with pharmaceutically acceptable carriers, diluents, adjuvants and vehicles.

The term "prophylactically effective amount" refers to an amount of a HB-X conjugate which is effective, at dosages and for periods of time necessary, to achieve the desired prophylactic result. Typically, since a prophylactic dose of HB-X conjugate is administered to a subject prior to, or at an earlier stage of a disease, and in some embodiments, a prophylactically effective amount is less than the therapeutically effective amount. A prophylatically effective amount of a HB-X conjugate is also one in which any toxic or detrimental effects of the compound are outweighed by the beneficial effects.

As used herein, the terms "prevent," "preventing" and "prevention" refer to the avoidance or delay in manifestation of one or more symptoms or measurable markers of a disease or disorder, e.g., of an autoimmune disease. A delay in the manifestation of a symptom or marker is a delay relative to the time at which such symptom or marker manifests in a control or untreated subject with a similar likelihood or susceptibility of developing the disease or disorder. The terms "prevent," "preventing" and "prevention" include not only the avoidance or prevention of a symptom or marker of the disease, but also a reduced severity or degree of any one of the symptoms or markers of the disease, relative to those symptoms or markers in a control or non-treated individual with a similar likelihood or susceptibility of developing the disease or disorder, or relative to symptoms or markers likely to arise based on historical or statistical measures of populations affected by the disease or disorder. By "reduced severity" is meant at least a 10% reduction in the severity or degree of a symptom or measurable disease marker, relative to a control or reference, e.g., at least 15%, 20%, 30%, 40%, 50%, 60%, 70%, 80%, 90%, 95%, 99% or even 100% (i.e., no symptoms or measurable markers).

As used herein, the terms "administering," and "introducing" are used interchangeably herein and refer to the placement of HB-X conjugate of the present invention into a subject by a method or route which results in at least partial localization of the HB-X conjugate at a desired site. The compounds of the present invention can be administered by any appropriate route which results in an effective treatment in the subject.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. The phrases "systemic administration," "administered systemically", "peripheral administration" and "administered peripherally" as used herein mean the administration of HB-X such that it enters the animal's system and, thus, is subject to metabolism and other like processes, for example, subcutaneous administration.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation.

The term "reduced" or "reduce" or "decrease" as used herein generally means a decrease by a statistically significant amount relative to a reference. For avoidance of doubt, "reduced" means statistically significant decrease of at least 10% as compared to a reference level, for example a decrease by at least 20%, at least 30%, at least 40%, at least t 50%, or least 60%, or least 70%, or least 80%, at least 90% or more, up to and including a 100% decrease (i.e., absent level as compared to a reference sample), or any decrease between 10-100% as compared to a reference level, as that term is defined herein.

The terms "increased" or "increase" as used herein generally mean an increase by a statically significant amount; such as a statistically significant increase of at least 10% as compared to a reference level, including an increase of at least 20%, at least 30%, at least 40%, at least 50%, at least 60%, at least 70%, at least 80%, at least 90%, at least 100% or more, inclusive, including, for example at least 2-fold, at least 3-fold, at least 4-fold, at least 5-fold, at least 10-fold increase or greater as compared to a reference level, as that term is defined herein.

The term "high" as used herein generally means a higher by a statically significant amount relative to a reference; such as a statistically significant value at least 10% higher than a reference level, for example at least 20% higher, at least 30% higher, at least 40% higher, at least 50% higher, at least 60% higher, at least 70% higher, at least 80% higher, at least 90% higher, at least 100% higher, inclusive, such as at least 2-fold higher, at least 3-fold higher, at least 4-fold higher, at least 5-fold higher, at least 10-fold higher or more, as compared to a reference level.

The term "subject" as used herein refers to any animal in which it is useful to modulate a response in a tissue targeted by the HB moiety of the composition. The subject can be a wild, domestic, commercial or companion animal such as a bird or mammal. The subject can be a human. Although in one embodiment of the invention it is contemplated that the therapeutic compositions as disclosed herein, can also be suitable for the therapeutic treatment in humans, it is also applicable to warm-blooded vertebrates, e.g., mammals, such as non-human primates, (particularly higher primates), sheep, dog, rodent (e.g., mouse or rat), guinea pig, goat, pig, cat, rabbits, cows, and non-mammals such as chickens, ducks, or turkeys. In some embodiments, the subject is an experimental animal or animal substitute as a disease model.

The term "pharmaceutically acceptable" refers to compounds and compositions which may be administered to mammals without undue toxicity. The term "pharmaceutically acceptable carriers" excludes tissue culture medium. Exemplary pharmaceutically acceptable salts include but are not limited to mineral acid salts such as hydrochlorides, hydrobromides, phosphates, sulfates, and the like, and the salts of organic acids such as acetates, propionates, malonates, benzoates, and the like. Pharmaceutically acceptable carriers are well-known in the art. Some pharmaceutically acceptable carriers may be used to provide for sustained release of the compositions described herein. For example, hyaluronic acid and hyaluronic acid gel forms are used in intra-articular injections, and can be used to provide for sustained release of the HB-X compositions.

As used herein, the terms "treating," "treatment", and "to treat" are used to indicate the production of beneficial or desired results, such as to alleviate symptoms, or eliminate the causation of a disease or disorder either on a temporary or a permanent basis, slow the appearance of symptoms and/or progression of the disorder, or prevent progression of disease. The terms "treat" or "treatment" refer to both therapeutic treatment and prophylactic or preventative measures. Beneficial or desired clinical results include, but are not limited to, alleviation of symptoms, diminishment of extent of autism, stabilized (i.e., not worsening) state of pathology involvement, delay or slowing of disease progression, amelioration or palliation of the disease state. An "effective regimen" is administered over an effective course (a sufficient treatment or amount over a sufficient period of time) to achieve level of desired results. Monitoring efficacy can be done by methods known in the art for the particular disease or its symptoms.

HB-X Conjugates

An aspect of the present invention as disclosed herein comprises a therapeutic composition comprising, for example, (HB-linker)$_n$-X$_m$-(linker-HB)$_o$, where HB is a heparin binding protein, X is an active agents such as a therapeutic protein or a portion thereof, or a therapeutic small molecule, and where n, m, and o are integers, and m is at least one and n+o is at least one.

In some embodiments, a HB-X conjugate is HB-X$_n$, or (HB-linker)$_n$-X$_n$, and where n is an integer of at least 1. The HB can be attached to the N- or C-terminus, or both the N- and C-terminus of the active agent X. In some embodiments, a HB-X conjugate is a recombinant fusion protein comprising a recombinant HB and the therapeutic protein. In some embodiments, a HB-X conjugate is comprises a HB peptide as disclosed herein and a small molecule. In both instances, the HB peptide can be attached (e.g., conjugated) with an active agent with or without a linker entity.

In some embodiments, the components of a HB-X conjugate can be placed in order, relative to the N-terminus of the HB portion of the composition: HB-X, X-HB, HB-linker-X, (HB-linker)n-X, X-(linker-HB)n, X-HBn-X, HBn-X-HBn, (HB-linker)n-Xm-(linker-HB)n, HBn-Xm-HBn-Xm, etc.

In some embodiments, a HB-X conjugate can comprise at least 1, or at least 2, or at least 3, or at least about 4, or at least about 6, or at least about 7, or at least about 8, or at least about 9, or at least about 10, or more than 10 HB peptides of SEQ ID NO: 1-3 or 20-22. A HB-X conjugate with more than one HB peptide can have all the same type of HB peptide (e.g., all HB peptides comprise SEQ ID NO: 2) or can comprise any combination of different HB peptides from SEQ ID N: 1-3, or 20-22. In some embodiments, a HB-X conjugate can comprise at least one linker associated with a HB peptide, e.g., each HB present in a HB-X conjugate can be associated with a linker. Alternatively, in some embodiments, where a HB-X conjugate comprises more than one HB peptide, not all HB peptides in a HB-X conjugate need be associated with a linker. The HB peptides can be randomly or non-randomly interspersed between a sequence of active agents in a HB-X conjugate, e.g., as an exemplary example, HB-X-X-X-HB-X-X-X-HB, or X-X-HB-X-HB-X-HB-X-X-X-HB- etc. Such a random or non-random interdispersion of HB peptides between X active entities can occur with or without linkers, as disclosed herein.

Additionally, the composition can comprise a mixture of HB-X constructs, wherein X represents different proteins or small molecules (i.e., a composition comprising HB-X$^1$ and HB-X$^2$, etc.).

In some embodiments, a HB-X conjugate can comprise at least 1, or at least 2, or at least 3, or at least about 4, or at least about 6, or at least about 7, or at least about 8, or at least about 9, or at least about 10, or more than 10 active agents (X). Active agents can be a therapeutic protein or peptide as disclosed herein, or a small molecule.

Heparin Binding Proteins (HB)

The present invention relates to proteinaceous heparin-binding motifs (HB) that are linked to or fused to a therapeutic moiety or active agent, such as a small molecule, or a cytokine or growth factor or functional portion thereof. In some embodiments, the HB peptide can be selected from peptides having the amino acid residue sequence: KRKKKGKGLGKKRDPCLRKYK (SEQ ID NO:1); KRKKKGKGLGKKRDPRLRKYK (SEQ ID NO:2) (C16R); or KRKKKGKGLGKKRDPKLRKYK (SEQ ID NO:3) (C16K). In some embodiments, the HB peptide can be selected from peptides having the amino acid residue sequence: MKRKKKGKGLGKKRDPCLRKYK (SEQ ID NO:20); MKRKKKGKGLGKKRDPRLRKYK (SEQ ID NO:21) (C17R); or MKRKKKGKGLGKKRDPKLRKYK (SEQ ID NO:22) (C17K).

In some embodiments, a HB portion of the composition is positively charged through many lysine and arginine residues; and binds to cellular or tissue proteoglycans which are negatively charged by sulfate groups. In particular embodiments, a HB is mutated to enhance the positive charge, by replacing the native cysteine residue found at position 16 of the HB having the residues of SEQ ID NO:1 with an arginine (SEQ ID NO:2) (C16R) or lysine (SEQ ID NO:3) (C16K). The HB can be repeated with or without the inclusion of a peptide linker. Example tandem HB peptide constructs with linkers be represented HB-linker-HB-X, wherein HB-linker-HB comprises the HB variant of SEQ ID NO: 2 and has the amino acids: KRKKKGKGLGKKRDPRL-RKYKGGGKRKKKGKGLGKKRDPRLRKYK (SEQ ID NO:4); or HB-linker-HB-linker-HB-X, wherein HB-linker-HB-linker-HB has the residues: KRKKKGKGLGKKRD-PRLRKYKGGGKRKKKGKGLGKKRDPRL-RKYKGGGKRKKKGKG LGKKRDPRLRKYK (SEQ ID NO:5). In some embodiments, the tandem HB peptide constructs with linkers be represented HB-linker-HB-X, wherein a HB-linker-HB construct that comprises the HB variant of SEQ ID NO: 3 has the amino acids: KRKKKGKGLGKKRD-PKLRKYKGGGKRKKKGKGLGKKRDPKLRKYK (SEQ ID NO:23); or HB-linker-HB-linker-HB-X, wherein HB-linker-HB-linker-HB that comprises the HB variant of SEQ ID NO: 3 has the residues: KRKKKGKGLGKKRDP-KLRKYKGGGKRKKKGKGLGKKRDPKL-RKYKGGGKRKKKGKG LGKKRDPKLRKYK (SEQ ID NO:24). In some embodiments, the tandem HB constructs comprise the same HB construct. In alternative embodiments, it is envisioned that the tandem HB peptide constructs can comprise different combinations of HB peptides, e.g., any combination of SEQ ID NO: 1, SEQ ID NO: 2 or SEQ ID NO: 3, in any order. As an exemplary example, a tandem HB peptide construct can comprise SEQ ID NO: 2-linker-SEQ ID NO:3-linker-SEQ ID NO:3-X. In some embodiments a tandem HB peptide construct comprises a combination of HB peptides of SEQ ID NO: 2 and SEQ ID NO: 3 only.

Linkers

The attachment of a HB peptide to X can be by means of linkers, such as, but not limited to chemical modification, peptide linkers, chemical linkers, covalent or non-covalent bonds, or protein fusion or by any means known to one skilled in the art. The joining can be permanent or reversible. In some embodiments, several linkers can be included in order to take advantage of desired properties of each linker and each protein in the conjugate. Flexible linkers and linkers that increase the solubility of the conjugates are contemplated for use alone or with other linkers as disclosed herein. Peptide linkers can be linked by expressing DNA encoding the linker to one or more proteins in the conjugate. Linkers can be acid cleavable, photocleavable and heat sensitive linkers. Methods for conjugation are well known by persons skilled in the art and are encompassed for use in the present invention.

In some embodiments, a HB peptide can be joined to an active agent X, where the active agent is a therapeutic peptide or protein by a peptide linker. Peptide linkers can be linked by expressing DNA encoding the linker to one or more proteins in the conjugate. In some embodiments, a peptide linker is GGG. Optionally the linker peptide will be joined at one or both of the amino terminus and carboxy terminus of the HB peptide with a short flexible linker, e.g. comprising at least about 2, 3, 4 or more glycine, serine and/or alanine residues.

In some embodiments, one such linker comprises the motif (GGGGS) (SEQ ID NO: 42), and may be present in one or more copies. In some embodiments, the linker comprises positively charged amino acid residues.

According to the present invention, the HB peptide can be linked to an active agent via any suitable means, as known in the art, see for example U.S. Pat. Nos. 4,625,014, 5,057,301 and 5,514,363, which are incorporated herein in their entirety by reference.

A large variety of methods for conjugation of a HB peptide as disclosed herein with X, e.g., a first fusion partner (e.g. a therapeutic protein or peptide) are known in the art. Such methods are e.g. described by Hermanson (1996, Bioconjugate Techniques, Academic Press), in U.S. Pat. No. 6,180,084 and U.S. Pat. No. 6,264,914 which are incorporated herein in their entirety by reference and include e.g. methods used to link haptens to carriers proteins as routinely used in applied immunology (see Harlow and Lane, 1988, "Antibodies: A laboratory manual", Cold Spring Harbor Laboratory Press, Cold Spring Harbor, N.Y.). It is recognized that, in some cases, a HB peptide and/or therapeutic protein or peptide can lose efficacy or functionality upon conjugation depending, e.g., on the conjugation procedure or the chemical group utilized therein. However, given the large variety of methods for conjugation the skilled person is able to find a conjugation method that does not or least affects the efficacy or functionality of the entities, such as an HB peptide and the therapeutic peptide which is to be conjugated.

In some embodiments a HB peptide can be conjugated to an active agent (X) by cross-linking. Crosslinking reagents include glutaraldehyde (GAD), bifunctional oxirane (OXR), ethylene glycol diglycidyl ether (EGDE), N-hydroxysuccinimide (NHS), and a water soluble carbodiimide, preferably 1-ethyl-3-(3-dimethylaminopropyl) carbodiimide (EDC). As is known to the skilled artisan, any crosslinking chemistry can be used, including, but not limited to, thioether, thioester, malimide and thiol, amine-carboxyl, amine-amine, and others listed in organic chemistry manuals, such as, Elements of Organic Chemistry, Isaak and Henry Zimmerman Macmillan Publishing Co., Inc. 866 Third Avenue, New York, N.Y. 10022.

Other linkage approaches to conjugate the HB peptide to the active agent, include but are not limited to aminocaproic horse radish peroxidase (HRP) or a heterobiofunctional cross-linker, e.g. carbonyl reactive and sulfhydryl-reactive cross-linker. Heterobiofunctional cross linking reagents usually contain two reactive groups that can be coupled to two different function targets on proteins and other macromolecules in a two or three-step process, which can limit the degree of polymerization often associated with using homobiofunctional cross-linkers. Such multistep protocols can offer a great control of conjugate size and the molar ratio of components.

In some embodiments, a HB peptide is conjugated to a nucleic acid active agent, e.g., RNAi agent or miRNA agent using a protamine linker, as disclosed in the U.S. Patent Application Publication Nos. US2002/0132990 and US2004/0023902, which are incorporated herein in their entirety by reference. In particular, where a linker is a protamine or protamine like agent, the methods, regents and reference that describe the preparation of protamine associated with a HB peptide are disclosed in U.S. Provisional Application 60/957, 023 and US Patent Applications US2007/012152, and US 2010/0209440, which are each incorporated herein in their entirety by reference. In some embodiments, a protamine linker encompassed for use in the present invention comprises SEQ ID NO: 1-6 disclosed in US 2010/0209440.

Suitable methods for conjugation of a HB peptide as disclosed herein with X (e.g., a first fusion partner (e.g. a therapeutic protein or peptide) include e.g. carbodimide conjugation (Bauminger and Wilchek, 1980, Meth. Enzymol. 70: 151-159). Alternatively, a moiety can be coupled to a targeting agent as described by Nagy et al., Proc. Natl. Acad. Sci. USA 93:7269-7273 (1996), and Nagy et al., Proc. Natl. Acad. Sci. USA 95:1794-1799 (1998), each of which are incorporated herein by reference. Another method for conjugating one can use is, for example sodium periodate oxidation followed by reductive alkylation of appropriate reactants and glutaraldehyde crosslinking.

One can use a variety of different linkers to conjugate a HB peptide as disclosed herein with X (e.g., a first fusion partner (e.g. a therapeutic protein or peptide), for example but not limited to aminocaproic horse radish peroxidase (HRP) or a heterobiofunctional cross-linker, e.g. carbonyl reactive and sulfhydryl-reactive cross-linker. Heterobiofunctional cross linking reagents usually contain two reactive groups that can be coupled to two different function targets on proteins and other macromolecules in a two or three-step process, which can limit the degree of polymerization often associated with using homobiofunctional cross-linkers. Such multi-step protocols can offer a great control of conjugate size and the molar ratio of components.

In some embodiments, a linker is a immunoglobulin hinge region linker as disclosed in U.S. Pat. Nos. 6,165,476, 5,856,456, US Application 2010/0063258 and International Application WO2012/142515, each of which are incorporated herein in their entirety by reference.

In some embodiments, a HB-X fusion protein can be produced in a cell-free system as disclosed in U.S. Application 2010/0063258, which is incorporated herein in its entirety by reference.

Exemplary linker sequences include for example: (i) the tail region of the membrane long isoform of IgA 1 (malL): SCSVADWQMPPPYVVLDLPQETLEEETPGAN (SEQ ID NO: 43), (ii) the tail region of the membrane variant long isoform of IgA 1 (ma 1 L with extra cys): SCCVADWQMPPPYVVLDLPQETLEEETPGAN (SEQ ID NO: 44), (iii) the tail region of the membrane short isoform of IgA 1 (mals with 6 amino acid N-terminal deletion):
DWQMPPPYVVLDLPQETLEEETPGAN (SEQ ID NO: 45), (iv) the tail region of the membrane bound form of IgA2: SCCVADWQMPPPYVVLDLPQETLEEETPGAN (SEQ ID NO: 46), (v) the tail region of the membrane bound form of IgD: YLAMTPLIPQSKDENSDDYTTFDDVGS (SEQ ID NO: 47), (vi) the tail region of the membrane-bound form of IgE: ELDVCVEEAEGEAPW (SEQ ID NO: 48), (vii) the tail region of the membrane bound form of IgG: ELQLEESCAEAQDGELDG (SEQ ID NO: 49), and (viii) the tail region of the membrane bound form of IgM EGEVSADEEGFEN (SEQ ID NO: 50).

In other embodiments, a linker sequence is derived from the tail segment of a secretory or soluble form of an immunoglobulin. Exemplary linker sequences include for example: (i) the tail region of the soluble form of IgA1: KPTHVNVSVVMAEVDGTCY (SEQ ID NO: 51), (ii) the tail region of the soluble form of IgA2: KPTHVNVSVVMAEVDGTCY (SEQ ID NO: 52), (iii) the tail region of the soluble form of IgD: YVTDHGPMK (SEQ ID NO: 53), and (iv): the tail region of the soluble form of IgM: PTLYNVSLVMSDTAGTCY (SEQ ID NO: 54).

In certain embodiments, it may be desirable to have a linker sequence containing a free cysteine residue in order to permit the formation of a disulfide bond between linkers thereby forming dimers of the HB fusion proteins. In other embodiments, it may be desirable to alter the linker sequences to remove free cysteine residues, e.g., by mutating one or more cysteine residues in a linker to another residue, such as a serine, alanine or glycine. Examples of linker sequences derived from the tail regions of membrane bound immunoglobulins that have been altered to remove free cysteine residues include:
(i) SXSVADWQMPPPYVVLDLPQETLEEETPGAN, wherein X is serine, alanine or glycine (SEQ ID NO: 55), (ii) SXXVADWQMPPPYVVLDLPQETLEEETPGAN, wherein each X is independently selected from serine, alanine or glycine (SEQ ID NO: 56), (iii) SXXVADWQMPPPYVVLDLPQETLEEETPGAN, wherein each X is independently selected from serine, alanine or glycine (SEQ ID NO: 57), (iv) ELDVXVEEAEGEAPW, wherein X is serine, alanine or glycine (SEQ ID NO: 58), and (v) ELQLEESXAEAQDGELDG, wherein X is serine, alanine or glycine (SEQ ID NO: 59). Examples of linker sequences derived from the tail regions of secretory forms of immunoglobulins that have been altered to remove free cysteine residues include: (i) KPTHVNVSVVMAEVDGTXY, wherein X is serine, alanine or glycine (SEQ ID NO: 60), (ii) KPTHVNVSVVMAEVDGTXY, wherein X is serine, alanine or glycine (SEQ ID NO: 61), and (iii) PTLYNVSLVMSDTAGTXY, wherein X is serine, alanine or glycine (SEQ ID NO: 62).

Active Agents—Therapeutic Proteins to Conjugate to a HB Peptide

The importance and usefulness of the compositions described herein are exemplified in the application of the composition in cartilage repair, wherein the fusion protein is HB-IGF-1. Traumatic injuries to the joint, such as those involving anterior cruciate ligament (ACL) rupture lead to an increased risk for development of osteoarthritis. Furthermore, this risk may not be resolved by surgical restoration of function (Lohmander et al., 35 Am. J. Sports Med. 1756 (2007)), which may be related an the initial inflammatory and catabolic response following joint injury. Lohmander et al., 42 Arthritis Rheum. 534 (1999); Lohmander et al., 48 Arthritis Rheum. 3130 (2003); Irie et al., 10 Knee 93 (2003). Therapeutic interventions in this time period may be particularly important for opposing these catabolic processes and promoting cartilage repair.

IGF-1 is the prototypical circulating factor that stimulates cartilage biosynthesis. Daughaday et al., 19 J. Clin. Endocrinol. Metab. 743 (1959); McQuillan et al., 240 Biochem. J. 423 (1986); Jones & Clemmons, 16 Endocrine Rev. 3 (1995). It also acts to oppose catabolic stimuli. Luyten et al., 267 Arch. Biochem. Biophys. 416 (1988); Tyler, 260 Biochem. J. 543 (1989). As a result, investigators have long sought to use IGF-1 as a therapy for cartilage repair. Trippel, 43 J. Rheumatol. Suppl. 129 (1995). Local delivery of IGF-1 and other growth factors is severely limited, however, by their short half-life in the joint. Investigators have developed options for gene therapy with IGF-1 and for IGF-1 encapsulated in hydrogels to allow for long-term controlled release to the joint cartilage. Although promising, these techniques have been slow to reach clinical trials. Evans et al., 7 Nat. Rev. Rheum. 244 (2011).

An example rat IGF-1 protein has the amino acid residues: GPETLCGAELVDALQFVCGPRGFY-FNKPTGYGSSIRRAPQTGIVDECCFR-SCDLRRLEMYCAPLK PTKSA (SEQ ID NO:6). See, e.g., Tokunou et al., 22 FASEB J. 1886 (2008).

An example human IGF-1 has the amino acid residues: GPETLCGAELVDALQFVCGDRGFYFNKPTGYGSSSRRAPQTGIVDECCFRSCDLRRLEMYCAPL KPAKSARSVRAQRHTDMPKTQKEVHLKNASRGSA (SEQ ID NO:7). See also Gene ID: 3489 (human IGF1). Another example human IGF-1 (variant) has the amino acid residue sequence: GPETLCGAELVDALQFVCGDRGFYFNKPTGYGSSSRRAPQTGIVDECCFRSCDLRRLEM YCAPLKPAKSA. (SEQ ID NO:8). A variant of human IGF-1 that has biological activity (see WO 92/03477; GenBank: CAA01451.1) has the amino acid residues: megpetlcgaelvdalqfvcgdrgfyfnkpt-gygsssrrapqtgivdeccfrscdlrrlemycaplkpaksa (SEQ ID NO:9).

It is known that truncation of the N-terminus of IGF-1 retains biological activity, e.g., the deletion of N-terminal amino acids GPE. Accordingly, in some embodiments, a human IGF-1 (variant) encompassed for use in the present invention has the amino acid residue sequence: TLCGAELVDALQFVCGDRGFYFNKPTGYGSSSRRAPQTGIVDECCFRSCDLRRLEMYC APLKPAKSA. (SEQ ID NO: 63).

Thus, in some embodiments a recombinant HB-linker-HB-X fusion protein, wherein HB is a C16R variant, the linker is GGG, and X is a variant of human IGF-1 of SEQ ID NO: 7, has the amino acid sequence: KRKKKGKGLGKKRDPRLRKYKGGGKRKKKGKGLGKKRDPRLRKYKGPETLCGAELVDA LQFVCGDRGFYFNKPTGYGSSSRRAPQTGIVDECCFRSCDLRRLEMY CAPLKPAKSARSVRAQR HTDMPKTQKEVHLKNASRGSA (SEQ ID NO:10); another recombinant HB-linker-HB-linker-HB-X, wherein HB is a C16R variant, the linker is GGG, and X is a variant of human IGF-1 (SEQ ID NO: 7) can be depicted: KRKKKGKGLGKKRDPRLRKYKGGGKRKKKGKGLGKKRDPRLRKYKGGGKRKKKGKGL GKKRDPRLRKYKGPETLCGAELVDALQFVCGDRGFYFNKPTGYGSSSRRA PQTGIVDECCFRS CDLRRLEMYCAPLKPAKSARSVRAQRHTDMPKTQKEVHLKNASRGSA (SEQ ID NO:11).

In some embodiments, a variant of IGF-1 of SEQ ID NO:7 can be substituted for SEQ ID NO: 8 or SEQ ID NO: 9. In some embodiments, the HB C16R (e.g., SEQ ID NO: 2) can be substituted for a HB C17R (e.g., MKRKKKGKGLGKKRDPRLRKYK; SEQ ID NO: 21) An example fusion of HB C17R with full-length human IGF-1 (of SEQ ID NO: 7) has the amino acids: MKRKKKGKGLGKKRDPRLRKYKGPETLCGAELVDALQFVCGDRGFYFNKPTGYGSSSRRAP QTGIVDECCFRSCDLRRLEMYCAPLKPAKSARSVRAQRHTDMPKTQKEVHLKNASRGSA (SEQ ID NO:12). In some embodiments, an example fusion of HB C16R with full-length human IGF-1 (of SEQ ID NO: 7) (e.g., HB-IGF) has the amino acids: KRKKKGKGLGKKRDP RLRKYKGPETLCGAELVDALQFVCGDRGFYFN KPTGYGSSSRRAPQ TGIVDECCFRSCDLRRLEMYCAPLKPAKSARSVRAQRHTDMPKTQKEVHLKNASRGSA (SEQ ID NO:16).

In some embodiments, HB C16R (e.g., SEQ ID NO: 2) or HB C17R (SEQ ID NO: 21) can be substituted for HB C16K (SEQ ID NO: 3) or HB C17K (MKRKKKGKGLGKKRDPKLRKYK; SEQ ID NO: 22). For example, in another example, a fusion of HB C17K with full-length human IGF-1 (e.g., SEQ ID NO: 7) has the amino acids: MKRKKKGKGLGKKRDP KLRKYKGPETLCGAELVDALQFVCGDRGFYF NKPTGYGSSSRRAP QTGIVDECCFRSCDLRRLEMYCAPLKPAKSARSVRAQRHTDMPKTQKEVHLKNASRGSA (SEQ ID NO:13). Truncations of human IGF-1 corresponding to SEQ ID NO: 8 fused to HB C17R has the amino acid sequence of: MKRKKKGKGLGKKRDP RLRKYKGPETLCGAELVDALQFVCGDRGFYFNK PTGYGSSSRRAP QTGIVDECCFRSCDLRRLEMYCAPLKPAKSA (SEQ ID NO:14) or KRKKKGKGLGKKRDPRLRKYKGPETLCGAELVDALQFVCGDRGFYFNKPTGYGSSSRRAPQ TGIVDECCFRSCDLRRLEMYCAPLKPAKSA (SEQ ID NO:18), and a fusion of HB C17K with mature human IGF-1: MKRKKKGKGLGKKRDPKLRKYKGPETLCGAELVDALQFVCGDRGFYFNKPTGYGSSSRRAP QTGIVDECCFRSCDLRRLEMYCAPLKPAKSA (SEQ ID NO:15)

Variants of the foregoing HB-fusion proteins can be constructed that lack the initial N-terminal methionine on the HB peptide, e.g., comprising SEQ ID NO: 1, SEQ ID NO: 2 or SEQ ID NO: 3, i.e., KRKKKGKGLGKKRDP RLRKYKGPETLCGAELVDALQFVCGDRGFYFN KPTGYGSSSRRAPQ TGIVDECCFRSCDLRRLEMYCAPLKPAKSARSVRAQRHTDMPKTQKEVHLKNASRGSA (SEQ ID NO:16); KRKKKGKGLGKKRDP KLRKYKGPETLCGAELVDALQFVCGDRGFYFN KPTGYGSSSRRAPQ TGIVDECCFRSCDLRRLEMYCAPLKPAKSARSVRAQRHTDMPKTQKEVHLKNASRGSA (SEQ ID NO:17); KRKKKGKGLGKKRDP RLRKYKGPETLCGAELVDALQFVCGDRGFYFNK PTGYGSSSRRAPQ TGIVDECCFRSCDLRRLEMYCAPLKPAKSA (SEQ ID NO:18); and KRKKKGKGLGKKRDP KLRKYKGPETLCGAELVDALQFVCGDRGFYFN KPTGYGSSSRRAPQ TGIVDECCFRSCDLRRLEMYCAPLKPAKSA (SEQ ID NO:19).

Table 1 discloses examples of different embodiments of fusion of HB peptide to an agent. As an exemplary agent (e.g., X), IGF-1 is used:

TABLE 1 discloses examples of different embodiments of fusion of HB peptide to an agent. As an exemplary (e.g., X), IGF-1 is used:

| HB peptide | Linker | IGF-1 variant (e.g., X) | Sequence |
| --- | --- | --- | --- |
| HB-linker-HB-X | C16R (SEQ ID NO: 2) | GG G | SEQ ID NO: 7 | KRKKKGKGLGKKRDPRLRKYKGGGKRKKKGKGLGK KRDPRLRKYKGPETLCGAELVDALQFVCGDRGFYFNKPT GYGSSSRRAPQTGIVDECCFRSCDLRRLEMYCAPLKPAKS ARSVRAQRHTDMPKTQKEVHLKNASRGSA (SEQ ID NO: 10); |

TABLE 1-continued discloses examples of different embodiments of fusion of HB peptide to an agent.
As an exemplary (e.g., X), IGF-1 is used:

| HB peptide | Linker | IGF-1 variant (e.g., X) | Sequence |
| --- | --- | --- | --- |
| HB-linker-HB-linker-HB-X | C16R (SEQ ID NO: 2) | GG G | SEQ ID NO: 7 | KRKKKGKGLGKKRDPRLRKYK*GGG*KRKKKGKGLGK KRDPRLRKYK*GGG*KRKKKGKGLGKKRDPRLRKYKGP ETLCGAELVDALQFVCGDRGFYFNKPTGYGSSSRRAPQTG IVDECCFRSCDLRRLEMYCAPLKPAKSARSVRAQRHTDMP KTQKEVHLKNASRGSA (SEQ ID NO: 11) |
| HB-X | C17R (SEQ ID NO: 21) | — | SEQ ID NO: 7 | MKRKKKGKGLGKKRDPRLRKYKGPETLCGAELVDALQ FVCGDRGFYFNKPTGYGSSSRRAPQTGIVDECCFRSCDLRR LEMYCAPLKPAKSARSVRAQRHTDMPKTQKEVHLKNASR GSA (SEQ ID NO: 12). |
| HB-X | C17K (SEQ ID NO: 22) | — | SEQ ID NO: 7 | MKRKKKGKGLGKKRDPKLRKYKGPETLCGAELVDALQ FVCGDRGFYFNKPTGYGSSSRRAPQTGIVDECCFRSCDLRR LEMYCAPLKPAKSARSVRAQRHTDMPKTQKEVHLKNASR GSA (SEQ ID NO: 13) |
| HB-X | C17R (SEQ ID NO: 21) | — | SEQ ID NO: 8 | MKRKKKGKGLGKKRDPRLRKYKGPETLCGAELVDALQ FVCGDRGFYFNKPTGYGSSSRRAPQTGIVDECCFRSCDLRR LEMYCAPLKPAKSA (SEQ ID NO: 14) |
| HB-X | C17K (SEQ ID NO: 22) | — | SEQ ID NO: 8 | MKRKKKGKGLGKKRDPKLRKYKGPETLCGAELVDALQ FVCGDRGFYFNKPTGYGSSSRRAPQTGIVDECCFRSCDLRR LEMYCAPLKPAKSA (SEQ ID NO: 15) |
| HB-X | C16R (SEQ ID NO: 2) | — | SEQ ID NO: 7 | KRKKKGKGLGKKRDPRLRKYKGPETLCGAELVDALQF VCGDRGFYFNKPTGYGSSSRRAPQTGIVDECCFRSCDLRRL EMYCAPLKPAKSARSVRAQRHTDMPKTQKEVHLKNASRG SA (SEQ ID NO: 16); |
| HB-X | C16K (SEQ ID NO: 3) | — | SEQ ID NO: 7 | KRKKKGKGLGKKRDPKLRKYKGPETLCGAELVDALQF VCGDRGFYFNKPTGYGSSSRRAPQTGIVDECCFRSCDLRRL EMYCAPLKPAKSARSVRAQRHTDMPKTQKEVHLKNASRG SA (SEQ ID NO: 17); |
| HB-X | C16R (SEQ ID NO: 2) | — | SEQ ID NO: 8 | KRKKKGKGLGKKRDPRLRKYKGPETLCGAELVDALQF VCGDRGFYFNKPTGYGSSSRRAPQTGIVDECCFRSCDLRRL EMYCAPLKPAKSA (SEQ ID NO: 18); |
| HB-X | C16K (SEQ ID NO: 3) | — | SEQ ID NO: 8 | KRKKKGKGLGKKRDPKLRKYKGPETLCGAELVDALQF VCGDRGFYFNKPTGYGSSSRRAPQTGIVDECCFRSCDLRRL EMYCAPLKPAKSA (SEQ ID NO: 19). |
| HB-linker-HB-X | C16R (SEQ ID NO: 2) | GG G | SEQ ID NO: 8 | KRKKKGKGLGKKRDPRLRKYK*GGG*KRKKKGKGLGK KRDPRLRKYKGPETLCGAELVDALQFVCGDRGFYFNKPT GYGSSSRRAPQTGIVDECCFRSCDLRRLEMYCAPLKPAKS A (SEQ ID NO: 25); |
| HB-linker-HB-linker-HB-X | C16R (SEQ ID NO: 2) | GG G | SEQ ID NO: 8 | KRKKKGKGLGKKRDPRLRKYK*GGG*KRKKKGKGLGK KRDPRLRKYK*GGG*KRKKKGKGLGKKRDPRLRKYKGP ETLCGAELVDALQFVCGDRGFYFNKPTGYGSSSRRAPQTG IVDECCFRSCDLRRLEMYCAPLKPAKSA (SEQ ID NO: 26) |
| HB-linker-HB-X | C16K (SEQ ID NO: 3) | GG G | SEQ ID NO: 7 | KRKKKGKGLGKKRDPKLRKYK*GGG*KRKKKGKGLGK KRDPKLRKYKGPETLCGAELVDALQFVCGDRGFYFNKPT GYGSSSRRAPQTGIVDECCFRSCDLRRLEMYCAPLKPAKS ARSVRAQRHTDMPKTQKEVHLKNASRGSA (SEQ ID NO: 27); |
| HB-linker-HB-linker-HB-X | C16K (SEQ ID NO: 3) | GG G | SEQ ID NO: 7 | KRKKKGKGLGKKRDPKLRKYK*GGG*KRKKKGKGLGK KRDPKLRKYK*GGG*KRKKKGKGLGKKRDPKLRKYKGP ETLCGAELVDALQFVCGDRGFYFNKPTGYGSSSRRAPQTG IVDECCFRSCDLRRLEMYCAPLKPAKSARSVRAQRHTDMP KTQKEVHLKNASRGSA (SEQ ID NO: 28) |
| HB-linker-HB-X | C16K (SEQ ID NO: 3) | GG G | SEQ ID NO: 8 | KRKKKGKGLGKKRDPKLRKYK*GGG*KRKKKGKGLGK KRDPKLRKYKGPETLCGAELVDALQFVCGDRGFYFNKPT GYGSSSRRAPQTGIVDECCFRSCDLRRLEMYCAPLKPAKS A (SEQ ID NO: 29); |

TABLE 1-continued discloses examples of different embodiments of fusion of HB peptide to an agent. As an exemplary (e.g., X), IGF-1 is used:

| HB peptide | Linker | IGF-1 variant (e.g., X) | Sequence |
|---|---|---|---|
| HB-linker-HB-linker-HB-X | C16K (SEQ ID NO: 3) | GG G | SEQ ID NO: 8 | KRKKKGKGLGKKRDPKLRKYK*GGG*KRKKKGKGLGK KRDPKLRKYK*GGG*KRKKKGKGLGKKRDPKLRKYKGP ETLCGAELVDALQFVCGDRGFYFNKPTGYGSSSRRAPQTG IVDECCFRSCDLRRLEMYCAPLKPAKSA (SEQ ID NO: 30). |
| HB-X | C16R (SEQ ID NO: 2) | — | SEQ ID NO: 63 | KRKKKGKGLGKKRDP<u>R</u>LRKYKTLCGAELVDALQFVCG DRGFYFNKPTGYGSSSRRAPQTGIVDECCFRSCDLRRLEM YCAPLKPAKSARSVRAQRHTDMPKTQKEVHLKNASRGSA (SEQ ID NO: 64); |
| HB-X | C16K (SEQ ID NO: 3) | — | SEQ ID NO: 63 | KRKKKGKGLGKKRDP<u>K</u>LRKYKTLCGAELVDALQFVCG DRGFYFNKPTGYGSSSRRAPQTGIVDECCFRSCDLRRLEM YCAPLKPAKSARSVRAQRHTDMPKTQKEVHLKNASRGSA (SEQ ID NO: 65); |
| HB-X | C16R (SEQ ID NO: 2) | — | SEQ ID NO: 63 | KRKKKGKGLGKKRDP<u>R</u>LRKYKTLCGAELVDALQFVCG DRGFYFNKPTGYGSSSRRAPQTGIVDECCFRSCDLRRLEM YCAPLKPAKSA (SEQ ID NO: 66); |
| HB-X | C16K (SEQ ID NO: 3) | — | SEQ ID NO: 63 | KRKKKGKGLGKKRDP<u>K</u>LRKYKTLCGAELVDALQFVCG DRGFYFNKPTGYGSSSRRAPQTGIVDECCFRSCDLRRLEM YCAPLKPAKSA (SEQ ID NO: 67). |
| HB-X | C16R (SEQ ID NO: 2) | GG G | SEQ ID NO: 63 | KRKKKGKGLGKKRDP<u>R</u>LRKYKGGGTLCGAELVDALQF VCGDRGFYFNKPTGYGSSSRRAPQTGIVDECCFRSCDLRRL EMYCAPLKPAKSARSVRAQRHTDMPKTQKEVHLKNASRG SA (SEQ ID NO: 68); |
| HB-X | C16K (SEQ ID NO: 3) | GG G | SEQ ID NO: 63 | KRKKKGKGLGKKRDP<u>K</u>LRKYKGGGTLCGAELVDALQF VCGDRGFYFNKPTGYGSSSRRAPQTGIVDECCFRSCDLRRL EMYCAPLKPAKSARSVRAQRHTDMPKTQKEVHLKNASRG SA (SEQ ID NO: 69); |
| HB-X | C16R (SEQ ID NO: 2) | GG G | SEQ ID NO: 63 | KRKKKGKGLGKKRDP<u>R</u>LRKYKGGGTLCGAELVDALQF VCGDRGFYFNKPTGYGSSSRRAPQTGIVDECCFRSCDLRRL EMYCAPLKPAKSA (SEQ ID NO: 70); |
| HB-X | C16K (SEQ ID NO: 3) | GG G | SEQ ID NO: 63 | KRKKKGKGLGKKRDP<u>K</u>LRKYKGGGTLCGAELVDALQF VCGDRGFYFNKPTGYGSSSRRAPQTGIVDECCFRSCDLRRL EMYCAPLKPAKSA (SEQ ID NO: 71). |

It is also encompassed that the HB peptide can be located at the N-terminus or C-terminus or at the N- and C-terminus of the active agent, e.g., an active agent for example, such as IGF-1. In some embodiments, the HB peptide can be located at the N-terminus or C-terminus or at the N- and C-terminus of the active agent with or without a linker at each transition between the HB peptide and the active agent. Accordingly, variations of the sequences in Table 1 (e.g., SEQ ID NO: 12-71) are encompassed where the HB is located at the C-terminus instead of the N-terminus, and where there is the presence or absence of a linker between the IGF-1 protein and the sequence of the C-terminus HB. In additional embodiments, variations of the sequences in Table 1 (e.g., SEQ ID NO: 12-71) are encompassed where the HB is located at both the C- and N-terminus, and where there is the presence or absence of a linker between the IGF-1 protein and the sequence of the C- or N-terminus HB. Any combination of a HB peptide selected from the group of SEQ ID NO: 1-3 or 30-22 can be used in any combination of an active agent, with or without the presence of a linker protein, where the HB peptide can be located at the N- and/or C-terminus of the active agent, and there can be one or multiple HB peptide-linkers attached to the N- and/or C-terminus of the active agent. For example, in some embodiments, the fusion or conjugate can comprise (HB-linker)$_n$-X$_m$-(linker-HB)$_o$, where n, m, and o are integers, and m is at least one and n+o is at least one.

The inventors have previously demonstrated an approach to stimulating cartilage biosynthesis uses an engineered rat IGF-1 protein fused with a rat heparin-binding domain, where the heparin-binding IGF-1 (HB-IGF-1) fusion protein is retained in cartilage after intra-articular injection. (Miller et al., 62 Arth. Rheum. 3686 (2010)). Herein, instead of using the wild-type rat HB peptide as used Miller, the inventors have modified the human wild-type HB peptide (e.g., corresponding herein to SEQ ID NO: 1), and surprisingly demonstrate that the HB constructs of SEQ ID NO: 2 or 3 as disclosed herein (where the C16 of SEQ ID NO: 1 or C17 of SEQ ID NO: 20 is changed from a cysteine (C) to an arginine (R) or lysine (K)) results in both (i) a significantly increased expression and yield of the HB-IGF-1 fusion protein and (ii) increased retention of the HB-fusion protein in the tissue of interest. Accordingly, the novel mutations in the wild-type human HB peptide to change C16 (of SEQ ID NO: 1) or C17 (of SEQ ID NO: 20) to enhance the positive charge suprizingly resulted in an unexpected increase in the expression and production of HB-X fusion proteins.

The present specification thus demonstrated the kinetics of a HB-IGF-1 fusion protein comprising SEQ ID NO: 2 or SEQ ID NO: 3 after intra-articular injection, and shows functional stimulation of HB-IGF-1 on joint cartilage in vivo, and demonstrates therapeutic efficacy in vivo of HB-IGF-1 in a rat model of joint injury-induced arthritis.

Accordingly, in some embodiments, a HB peptide of SEQ ID NO: 1-3 or 20-22, particularity a HB-X conjugate comprising at least one or a combination of SEQ ID NO: 2, 3, 21 or 22, conjugated to an active agent, such as but not limited to an IGF-1 protein or functional fragment thereof (e.g., any IGF-1 variant selected from the sequences from the group of: SEQ ID NO: 6-9 or 63) is encompassed for use in the present invention in methods to treat a cartilage-related disease or disorder.

Figure 2:
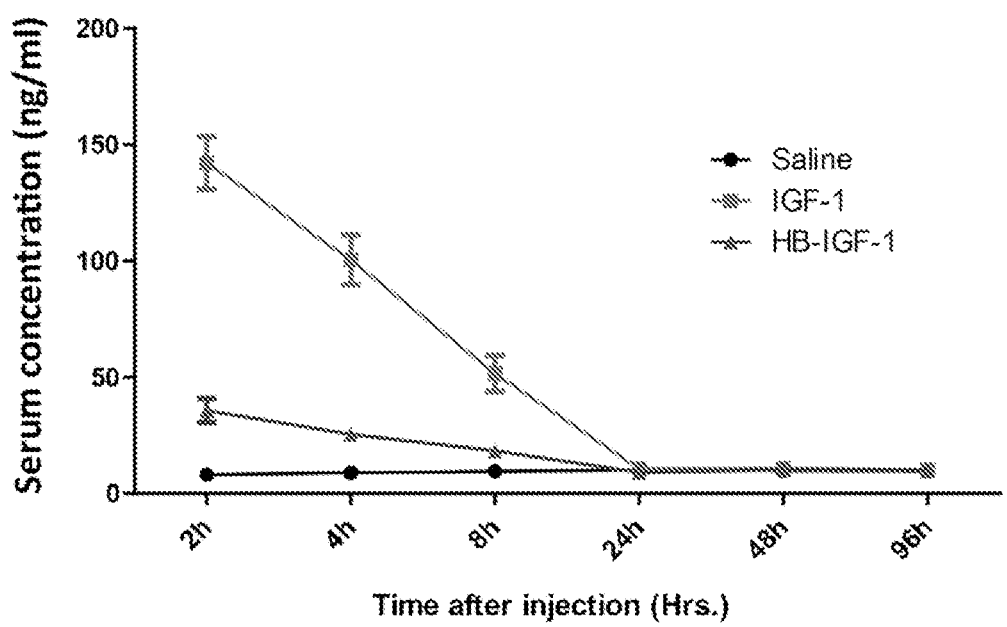
FIG. 2 shows serum levels of IGF-1 vs. HB-IGF-1 after intra-articular injection. Male Lewis rats 251-275 g (Charles River, Wilmington Mass.) were randomly assigned to one of three groups (n=3 for each group) HB-IGF-1, IGF-1 or Saline. Rats received 50 μl intra-articular injections containing either 100 μg of HB-IGF-1, 100 μg IGF-1, or Saline in the right knee joint. Blood was harvested via tail vein at 2, 4, 8, 24, 48, and 96 hours after injection. Serum levels were measured with an ELISA (R&D Systems, Minneapolis, Minn.). HB-IGF-1 levels in serum were significantly lower than IGF-1 levels at the first three time points. HB-IGF-1 levels were not significantly different from Saline after 2 hours. This shows that intra-articular injection of HB-IGF-1 limits the amount of non-specific IGF-1 circulation compared with non-HB associated IGF-1.

The inventors demonstrate herein that surprisingly, unlike IGF-1 alone (e.g., not fused to an agent), not only is a HB-IGF-1 fusion protein as disclosed herein retained in extracellular matrix of the cartilage after intra-articular injection, it is still able to stimulate cells in the cartilage and is therapeutically effective. More specifically, to determine the kinetics of HB-IGF-1 binding to cartilage in vivo, joint tissues were harvested after injection and tissue extracts analyzed by Western analysis (FIG. 1). Two days after injection of IGF-1, there was no detectable IGF-1 remaining in any of the joint tissues harvested. In contrast, HB-IGF-1 was retained in both articular and meniscal cartilages, but not in patellar tendon. A similar result was observed four days after injection. By 6 to 8 days after injection, HB-IGF-1 was still detectable in the cartilage extracts but the immunoreactive bands were faint and more variable. These results demonstrate that, unlike IGF-1, the present HB-IGF-1 fusion protein is retained in articular cartilage for up to 8 days after intra-articular injection. The pharmacokinetics of IGF-1 in serum are shown in FIG. 2, indicating that intra-articularly injected HB-IGF-1 had markedly reduced leakage into the systemic circulation compared with unmodified IGF-1.

Figure 3:
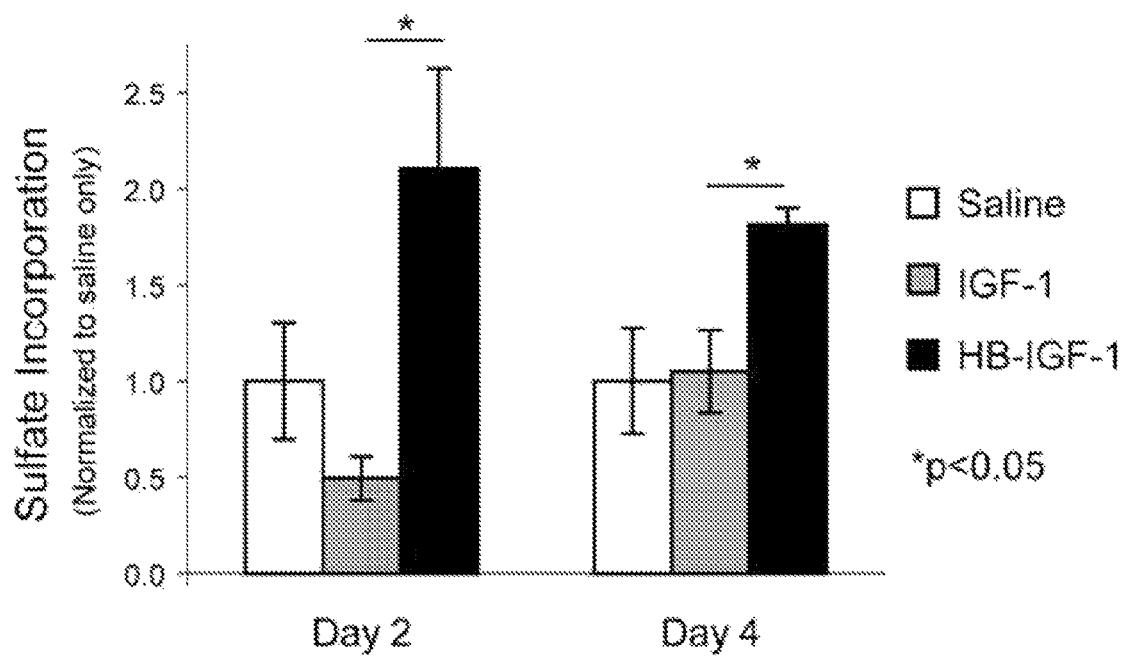
FIG. 3 is a bar graph depicting ex vivo sustained stimulation of cartilage biosynthesis and proliferation by HB-IGF-1 after intra-articular injection in rats. Rats received a single 50 μl intra-articular injection containing either 100 μg of an embodiment of HB-IGF-1, 100 μg IGF-1, or PBS in the right knee joint. Rats were sacrificed 2 and 4 days after the injection and the meniscus was harvested and cultured with radiolabel. Graph represents [$^{35}$S] sulfate incorporation in the meniscus 2 and 4 days after intra-articular injection. Results are shown as mean±SEM.

Additionally, the HB-IGF-1 produced sustained stimulation of cartilage biosynthesis in vivo. HB-IGF-1 remains able to activate cellular IGF-1 receptors in vivo despite its increased binding to chondroitin sulfate in the cartilage extracellular matrix. Sulfate incorporation into meniscal cartilage harvested after injection was measured and normalized to incorporation after injection of saline only (FIG. 3). Two days after injection, HB-IGF-1 stimulated a significantly higher rate of sulfate incorporation than did IGF-1 (HB-IGF: 2.10±0.52; IGF: 0.49±0.11; N=4-5/group; P=0.032). Four days after injection, sulfate incorporation remained significantly higher in the HB-IGF-1 group than in the IGF-1 group (HB-IGF: 1.82±0.09; IGF: 1.05±0.21; N=5/group; P=0.011).

Figure 4:
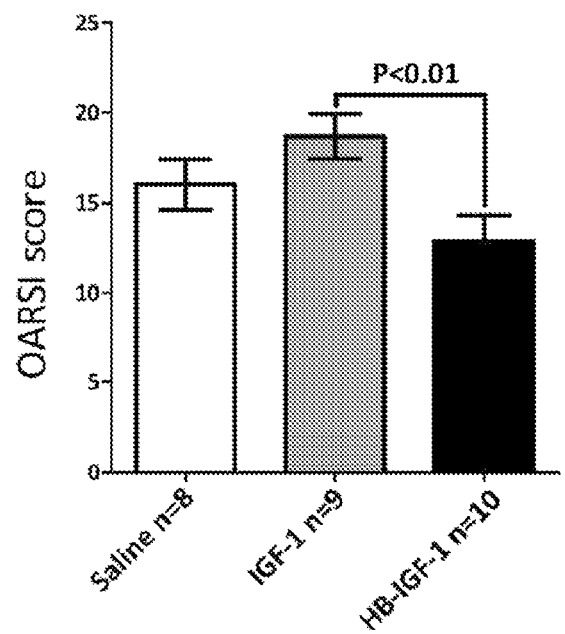
FIG. 4 is a bar graph from an osteoarthritis study comparing OARSI scores of HB-IGF-1, IGF-1, and PBS.

Further, HB-IGF-1 protects cartilage in vivo after transection of the medial meniscus. More specifically, HB-IGF-1 is efficacious in a rat model of surgically induced OA. Rats were subjected to medial meniscal tear (MMT) surgery and injected weekly with HB-IGF, IGF, or saline. Three weeks after MMT surgery, histological assessment of knee osteoarthritis (OA) was performed. For the primary outcome measure (FIG. 4), the overall OARSI score was significantly lower in the joints of the animals treated with HB-IGF-1 compared to control animals treated with IGF-1 (HB-IGF: 12.9±1.5; IGF: 18.7±1.2; N=9-10/group; P=0.008). Significant differences between HB-IGF-1 and IGF-1 treated knees were also observed on secondary analyses of total degeneration width and full-thickness cartilage loss, as shown in Table 2:

TABLE 2

Cartilage analysis in rat MMT model.
(Results are shown as mean ± SEM.)

| | Saline (n = 8) | IGF-1 (n = 9) | HB-IGF-1 (n = 10) |
|---|---|---|---|
| Surface cartilage loss | 174 ± 56 | 207 ± 39 | 120 ± 41 |
| Full-thickness cartilage loss | 36 ± 15 | 95 ± 35 | 0 ± 0 |
| Total degeneration width | 436 ± 28 | 506 ± 57 | 343 ± 36 |
| Significant degeneration width | 202 ± 13 | 236 ± 30 | 178 ± 17 |

In some embodiments, the compositions as disclosed herein provide for a therapeutic fusion protein that allows delivery and selective retention of bioactive proteins at a desired site. HB-IGF-1 was retained in articular cartilage and meniscus 4 to 8 days after injection at levels sufficient to stimulate proteoglycan synthesis. IGF-1 (no fused to HB) was not so retained. Accordingly, local delivery of HB-IGF-1 in vivo can reduce disease progression in a rat meniscal tear model of arthritis. Compared with IGF-1 or vehicle, HB-IGF-1 significantly reduced progression of cartilage damage as measured by a modified OARSI score. Secondary analyses demonstrated a lower cartilage degeneration score and the prevention of full-depth cartilage loss, suggesting a global beneficial effect on cartilage.

Although IGF-1 is one of the major anabolic growth factors for cartilage, attempts to repair cartilage and prevent osteoarthritis (OA) with intra-articular injection of IGF-1 alone have not been successful. Rogachefsky et al., 1993; Schmidt et al., 2006. The present data demonstrate that these negative results were not due to lack of effect of IGF-1 itself, but rather because "free" IGF-1 is not retained in cartilage for a significant amount of time (IGF-1 was retained less than 24 hours) after intra-articular delivery.

Additionally, these data have implications for injectable protein therapies for cartilage in general. Development of future therapies should assess whether a targeting mechanism will be required to produce sustained delivery to chondrocytes. The kinetics of retention in cartilage can be verified in other models or experiments so that a negative experimental results of a particular agent is not interpreted as a failure of the agent itself. Interestingly, FGF-18, another growth factor that has been shown to be therapeutic in this model, is a heparin-binding growth factor ((Moore et al., 2005) Hu et al., 1998; Chuang et al., 2010)).

As demonstrated herein in the Examples, HB-PTH (but not PTH alone) has also been demonstrated to be retained in cartilage explants.

Further, the systemic pharmacokinetic data suggest that IGF levels were not high enough to change glucose levels through binding to insulin receptors. If the increase in systemic levels is limited to ~24 hours, concerns about long-term elevation in IGF levels will be abated.

Moreover, an unexpected result observed herein was the robust response of both articular and meniscal cartilage to HB-IGF. Although the charge density of meniscus is heterogeneous and lower than that of articular cartilage, HB-IGF-1 was retained at levels sufficient to stimulate proteoglycan synthesis in meniscus. This demonstrated that HB-IGF may be directly protective for both articular cartilage and meniscus, and thus may be particularly effective after meniscal injuries.

HB-IGF as a therapy for OA may be less effective on late-stage OA as compared to early OA, because HB-IGF may require the presence of sulfated proteoglycans in the matrix for long-term retention in the cartilage. However, HB- IGF can be used as an effective new chondroprotective therapy in the setting of acute traumatic joint injury to a previously healthy joint.

In other embodiments, the HB-fusion protein comprises fibroblast growth factor 18 (FGF-18) or a functional portion thereof. FGF family members possess broad mitogenic and cell survival activities, and are involved in a variety of biological processes, including embryonic development, cell growth, morphogenesis, tissue repair. Thus, for example, the mature human FGF-18 can be incorporated into a HB-fusion protein, which FGF-18 has the amino acid sequence: EENVDFRIHVENQTRARDDVSRKQLRLYQLYSRTSGKHIQVLGRRISARGEDGDKYAQLLVETDTFGSQVRIKGKETEFYLCMNRKGKLVGKPDGTSKECVFIEKVLENNYTALMSAKYSGWYVGFTKKGRPRKGPKTRENQQDVHFMKRYPKGQPELQKPFKYTTVTKRSRRIRPTHPA (SEQ ID NO: 31). See also Gene ID: 8817. HB can be fused to the N- or C-terminus of FGF-18 (e.g., HB-FGF, FGF-HB, HB-linker-FGF, or FGF-linker-HB) or a portion of FGF-18, for example, residues 1-169 of the mature FGF-18.

In some embodiments, the HB-fusion protein comprises parathyroid hormone (PTH) or a portion thereof. PTH is implicated in maintaining calcium levels and osteostasis, and may prevent cartilage loss following joint injury. See, e.g., Harrington et al., 290 Anatom. Rec. 155 (2007). Thus, for example, the PTH may be mature PTH, having the amino acid sequence: SVSEIQLMHNLGKHLNSMERVEWLRKKLQDVHNFVALGAPLAPRDAGSQRPRKKEDNVLVES HEKSLGEADKADVNVLTKAKSQ (SEQ ID NO:32).

In some embodiments, HB can be fused to the amino- or carboxy-terminus of PTH or a portion of PTH, such as amino acid residues 1-31, 1-34, 1-37, 1-38, 1-44, or 1-84 of mature PTH. In some embodiments, a portion of PTH can be a fragment of the N-terminal 1-34 amino acids (referred to as PTH (1-34) corresponding to: SVSEIQLMHNLGKHLNSMERVEWLRKKLQDVHNF (SEQ ID NO:33). In some embodiments, a portion of PTH fused to a HB peptide can be selected from the following amino acids sequences: PTH(1-31): SVSEIQLMHNLGKHLNSMERVEWLRKKLQDV (SEQ ID NO:34); PTH(1-37): SVSEIQLMHNLGKHLNSMERVEWLRKKLQDVHNFVAL (SEQ ID NO: 35); PTH (1-44): SVSEIQLMHNLGKHLNSMERVEWLRKKLQDVHNFVALGAPLAPR (SEQ ID NO: 36).

As demonstrated herein in the Examples, HB-PTH(1-34) (but not PTH(1-34) alone) has also been demonstrated to be retained in cartilage explants. In some embodiments, a HB-PTH(1-34) fusion protein is a PTH(1-34)-linker HB fusion protein and comprises amino acids: SVSEIQLMHNLGKHLNSMERVEWLRKKLQDVHNFGGGKRKKKGKGLGKKRDPRLRKYK (SEQ ID NO: 37).

Additionally, the PTH may be an analog of PTH, such as cyclic PTH-(1-31). Recombinant human PTH(1-34) is currently marketed as FORTEO® (teriparatide [rDNA origin] injection) by Eli Lily & Co (Indianapolis, Ind.). OSTABOLIN-C™, (ZT-031; cyclic PTH-(1-31)) has been investigated in clinical trials by Zelos Therapeutics, Inc. (West Conshohocken, Pa.).

In still other embodiments, the HB-fusion protein comprises PTHrP or a portion thereof. PTHrP has been implicated in chondroprotection of newly regenerated cartilage following injury. Wang et al., 19 Osteoarth. Cartil. 213 (2011); Sampson et al., Ann. Meeting Am. Soc. Bone Mineral Res. (2009). Mature PTHrP has the amino acids: AVSEHQLLHDKGKSIQDLRRRFFLHHLIAEIHTAEIRATSEVSPNSKPSPNTKNHPVRFGSDDEGR YLTQETNKVETYKEQPLKTP (SEQ ID NO: 38). See also PLHLH, Gene ID:5744. The PTHrP HB fusion protein may be arranged, for example: PTHrP-linker-HB; PTHrP(1-34)-linker-HB; PTHrP(1-36)-linker-HB; PTHrP(1-37)-linker-HB; PTHrP(1-40)-linker-HB, etc.

Another example of a PTHrP-HB fusion protein includes a synthetic portion of PTHrP (AVSEHQLLHDKGKSIQDLRRRELLEKLLNKLHTA, where N is Aib (2-Aminoisobutyric acid) (SEQ ID NO: 39) can be fused to HB, for example, AVSEHQLLHDKGKSIQDLRRRELLEKLLNKLHTA (SEQ ID NO: 39)-linker-HB, where N is Aib (2-Aminoisobutyric acid). Aib in this PTHrP analog or derivative designates α-aminoisobutyric acid (also called 2-Aminoisobutyric acid, α-methylalanine, or 2-methylalanine). This PTHrP-related polypeptide can be made synthetically or by recombinant means, or by a combination thereof. See Wang et al., 292 Science 498 (2001); Ryu & Schultz, 3 Nat. Methods 263 (2006).

As noted, the compositions of the present invention can comprise HB-X2 or 2 or more different HB-X fusion proteins, etc., where X represents two different active agents. Thus for example, a composition can comprise any combination of HB-PTHrP and/or HB-PTH, and/or HB-IGF-1, e.g., for use in methods to regenerate cartilage, or stabilize regenerated cartilage following injury etc.

Still another example HB fusion protein fuses HB with IL1RA (Interleukin-1 receptor antagonist) as, for example, HB-linker-IL1RA or IL1RA-linker-HB. IL1RA is a member of the interleukin 1 cytokine family. IL1RA is secreted by various types of cells including immune cells, epithelial cells, and adipocytes, and is a natural inhibitor of the pro-inflammatory effect of IL1β. This protein inhibits the activities of interleukin 1, alpha (IL1A) and interleukin 1, beta (IL1B), and modulates a variety of interleukin 1 related immune and inflammatory responses. See Arend, 13 Cytokine Growth Factor Rev. 323 (2002). In some embodiments, the HB is fused with IL-1/IL-1 RA chimeras (e.g., as disclosed in Hou et al., PNAS, 2013, 110(10):3913-8), e.g., for use in the treatment of damage or disease to cartilage and/or meniscus, or for the treatment of eye or inflammatory conditions. Mature IL1RA has the amino acid sequence: RPSGRKSSKMQAFRIWDVNQKTFYLRNNQLVAGYLQGPNVNLEEKIDVVPIEPHALFLGIHGGK MCLSCVKSGDETRLQLEAVNITDLSENRKQDKRFAFIRSDSGPTTSFESAACPGWFLCTAMEAD QPVSLTNMPDEGVMVTKFYFQEDE (SEQ ID NO: 40). See also, Gene ID: 3557.

Another embodiment of the present invention, the HB fusion comprises HB fused to HGMB2 (also called HMG2). Articular cartilage is a tissue that provides biomechanical properties that allow near frictionless joint movement and dispersion of mechanical loads. Cartilage is composed of a single cell lineage but differences in the organization, phenotype and function of cells in the various layers of cartilage have been recognized. The superficial zone (SZ) is the most unique. SZ cells produce lubricin, also termed proteoglycan-4 (PRG4) or superficial zone protein (SZP), an important joint lubricant; are more responsive to stimulation by catabolic cytokines such as IL-1; and express mesenchymal stem cell markers. Expression of HMGB2 is restricted to the SZ of articular cartilage, and an interaction between HMGB2 and the Wnt/β-catenin pathway regulates the maintenance of the SZ and promotes chondrocyte survival. Importantly, joint ageing in humans and mice leads to a loss of HMGB2 expression that correlated with the onset of OA-like changes. Taniguchi et al., 106 PNAS 16817 (2009). Human HMG2 has the amino acid sequence (UniProtKB/Swiss-Prot: P26583.2; see also Gene ID: 3148): MGKGDPNKPR GKMSSYAFFV QTCREEHKKK HPDSSVNFAE FSKKCSERWK TMSAKEKSKF EDMAKSDKAR YDREMKNYVP PKGDKKGKKK DPNAPKRPPS AFFLFCSEHR PKIKSE-HPGL SIGDTAKKLG EMWSEQSAKD KQPYEQKAAK LKEKYEKDIA AYRAKGKSEA GKKGPGRPTG SKKKNEPEDE EEEEEEEDED EEEEDEDEE (SEQ ID NO: 824-1).

In some embodiments, a HB-fusion protein comprises somatostatin (SST) or a functional fragment or analogue thereof (e.g., a HB peptide can be conjugated to small molecules octreotide (brand name SANDOSTATIN®), pasireotide (SOM230, trade name SIGNIFOR®), lanreotide (trade name: SOMATULINE®)). Such a HB-fusion protein comprising SST or a functional fragment or variant or analogue thereof can be used for the treatment of defects and disorders in cartilage and/or meniscus and anti-inflammatory conditions. Human SST has the amino acid sequence (UniProtKB/Swiss-Prot: Hs.12409; see also Gene ID: 6750): MLSCRLQCAL AALSIVLALG CVTGAPSDPR LRQ-FLQKSLA AAAGKQELAK YFLAELLSEPNQTEN-DALEP EDLSQAAEQD EMRLELQRSA NSNPAMAPRE RKAGCKNFFW KTFTSC (SEQ ID NO: 72).

In some embodiments, a HB-fusion protein comprises angiopoietin-like 3 (ANGPTL3) or a functional fragment or analogue thereof. Such a HB-fusion protein comprising SST or a functional fragment or variant or analogue thereof can be used for the treatment of defects and disorders in cartilage and/or meniscus and anti-inflammatory conditions. Human preproproteinANGPTL3 has the amino acid sequence (UniProtKB/Swiss-Prot: Q9Y5C1; see also Gene ID: 27329 or NP_055310.1"): MFTIKLLLFIVPLVISSRIDQDNSSFD-SLSPEPKSRFAMLDDVKILANGLLQLGHGLKDFV H KTKGQINDIFQKLNIFDQSFYDLSLQT-SEIKEEEKELRRTTYKLQVKNEEVKNMSLELNS KL ESLLEEKILLQQKVKYLEEQLTNLIQNQ-PETPEHPEVTSLKTFVEKQDNSIKDLLQTVED QY KQLNQQHSQIKEIENQLRRT-SIQEPTEISLSSKPRAPRTTPFLQL-NEIRNVKHDGIPAECTT IYNRGEHTSGMYAIRPSN-SQVFHVYCDVISGSPWTLIQHRIDGSQNFNETWE NYKYGFG RLDGEFWLGLEKIYSIVKQSNYVLRI-ELEDWKDNKHYIEYSFYLGNHETNYTLHLVAIT GNVPNAIPENKDLVFSTWDHKAKGH-FNCPEGYSGGWWWHDECGENNLNGKYNKPRA KSKPERRRGLSW KSQNGRLYSIKSTKMLIHPTD-SESFE (SEQ ID NO: 73).

In some embodiments, a HB-fusion protein comprises a functional fragment of angiopoietin-like 3 (ANGPTL3). Functional fragments of ANGPTL3 include, but are not limited to: Human ANGPTL3 (241-455) corresponding to: GIPAECTTIYNRGEHTSGMYAIRPSN-SQVFHVYCDVISGSPWTLIQHRIDGSQNFNETWE NY KYGFGRLDGEFWLGLEKIYSIVKQ SNYVLRIELED-WKDNKHYIEYSFYLGNHETNYTLH LVAITGNVP-NAIPENKDLVFSTWDHKAKGHFNCP-EGYSGGWWWHDECGENNLNGKY NKPRAKSP ERRRGLSWKSQNGRLYSIKSTKMLIHPTD (SEQ ID NO: 74);

Human ANGPTL3 (225-455) TTPFLQLNEIRNVKHD-GIPAECTTIYNRGEHTSGMYAIRPSN-SQVFHVYCDVISGSPWTLI QHRIDGSQNFNET-WENYKYGFGRLDGEFWLGLEKIYSIVKQSNY VLRIELEDWKDNKH YIEYSFYLGNHETNY-TLHLVAITGNVPNAIPENKDLVFSTWDH-KAKGHFNCPEGYSGG WWWHDECGENNLNGKYNK-PRAKSPERRRGLSWKSQNGRLYSIKSTKMLIHPTD (SEQ ID NO: 75); Human ANGPTL3 (207-455) IQEPTEISLSSKPRAPRTTPFLQL-NEIRNVKHDGIPAECTTIYNRGEHTSG-MYAIRPSNSQV FHVYCDVISGSPWTLIQHRIDGSQN-FNETWENYKYGFGRL DGEFWLGLEKIYSIVKQSN YVLRIELEDWKDNKHYIEYSFYLGNHET-NYTLHLVAITGNVPNAIPENKDLVFSTWDHK AKGH-FNCPEGYSGGWWWHDECGENNLNGKYNK PRAK-SKPERRRGLSWKSQNGRLYS IKSTKMLIHPTD (SEQ ID NO: 76)

Brain proteoglycans, to which the HB associates, provide an avenue for selective delivery of therapeutic agents to the central nervous system. See, e.g., Brandtlow & Zimmerman, 80 Physiol. Rev. 1267 (2000). As demonstrated herein in the Examples, a HB-IGF-1 fusion protein is retained in the spinal cord. Accordingly, in some embodiments, a HB-fusion protein can comprise an active agent for delivery to the brain and spinal cord.

In some embodiments, a HB-fusion protein comprises IL-10. IL-10, an anti-inflammatory cytokine, is reportedly beneficial in subject having multiple sclerosis (MS); inducing anti-inflammatory cytokine IL-10 provided clinical advantage in MS patients. Ersoy et al., 12 Eur. J. Neurol. 208 (2005). Hence, another embodiment provides for a HB-X fusion in which X is IL-10 or a portion thereof.

Alternatively, where X is a therapeutic protein portion of a recombinant HB-X fusion protein, X can be selected from Neurotrophic factors, including Neurothrophins such as nerve growth factor (NGF; Gene ID: 4803), brain-derived neurotrophic factor (BDNF, Gene ID: 627), neurotrophin-3 (NT3, Gene ID:4908), neurotrophin-4 (NTF4, Gene ID: 4909), Ciliary neurotrophic factor (CNTF, Gene ID: 1270), mesencephalic astrocyte-derived neurotrophic factor (MANF, Gene ID: 7873), or cerebral dopamine neurotrophic factor (CDNF, Gene ID: 441549); Glial cell-line derived neurotrophic factor family ligands such as glial cell line-derived neurotrophic factor (GDNF, Gene ID: 2668), neurturin (NRTN, Gene ID: 4902), artemin (ARTN, Gene ID: 9048), or persephin (PSPN, Gene ID: 5623).

In some embodiments, the active agent X can be selected from Neuropoietic cytokines such as interleukin-6 (IL6, Gene ID: 3569), interleukin-11 (IL11, Gene ID: 3589), interleukin-27 (IL27, Gene ID: 246778), leukemia inhibitory factor (LIF, Gene ID: 3976), ciliary neurotrophic factor (CNTF, Gene ID:1270), cardiotrophin 1 (CTF1, Gene ID: 1489), neuropoietin (NP ortholog of mouse, human pseudogene Gene ID: 647088), cardiotrophin-like cytokine (CLGF1, Gene ID: 23529), or Fibroblast Growth Factor 2 (FGF2, Gene ID: 2247);

In some embodiments, the active agent X can be selected from Anti-inflammatory cytokines including interleukin-4 (ILR4, Gene ID: 3565), and interleukin-10 (ILR10, Gene ID:3586);

In some embodiments, the active agent X can be selected from Neuroprotection agents including Neuregulin-1 (NRG1, Gen ID: 3084), and Vascular endothelial growth factor (VEGFA, Gene ID: 7422, VEGFB, Gene ID: 7423, VEGFC, Gene ID: 7424).

Alternatively, in some embodiments the active agent X can be selected from other therapeutic proteins such as CEREBROLYSIN® (FPF-1070 pig brain peptide preparation, Ever Neuro Pharma, Austria), Growth differentiation factor 11 (GDF11, Gene ID: 10220), Stromal cell-derived factor-1 (SDF1, also CXCL12, Gene ID: 6387), Myostatin (MSTN, Gene ID:2660), Parathyroid hormone (PTH, Gene ID: 5741); Parathyroid hormone related peptide (PTHrP or PLHLH, Gene ID:5744); Interleukin 1 receptor antagonist (IL1RN, Gene ID: 3557); Fibroblast growth factor 18 (FGF18, Gene ID: 8817); High-mobility group box 2 (HMGB2, Gene ID: 3148); a therapeutic antibody or portion thereof, such as Remicade® (infliximab, anti-TNF-α, Janssen Biotech, Horsham, Pa.), Humira® (adalimumab, anti-TNF, Abbot Labs., N. Chicago, Ill.), or Enbrel® (etanercept, soluble recombinant TNF receptor 2 fused to the Fc component of human immunoglobulin G1, Amgen, Thousand Oaks, Calif.).

In some embodiments, the active agent X can be a Glucocorticoid receptor, such as nuclear receptor subfamily 3, group C, member 1 (NR3C1, Gene ID: 2908;

In some embodiments, the active agent X can be a portion, variant, analog, or derivative of any of preceding therapeutic proteins.

Active Agents—Therapeutic Small Molecules

In yet other embodiments, HB can be harnessed to effect selective delivery of therapeutic small molecules. For example, the small molecule TR2-01829, an optimized analog of PRO1, has chondrogenic properties. More specifically, PRO1 or an optimized analogue, a small molecule development candidate that has been shown to direct MSC differentiation down the chondrogenic pathway, may prove useful in regenerative therapy for OA. Additionally, 2-hydroxy-N-[3-(trifluoromethyl)phenyl]benzamide (HS-Cf) was a potent inhibitor of NO production and iNOS expression in TNF-α-stimulated porcine chondrocytes. By down-regulating TNF-α-induced IRF-1 activity, which suppressed chondrocyte activation and prevented cartilage destruction, HS-Cf might be a potential disease-modifying drug for OA therapeutics. Liu et al., 31 J. Clin. Immunol. 1131 (2011). In vitro and mouse studies suggest the small molecule kartogenin could help treat osteoarthritis. 5(18) SciBX (May 3, 2012).

The small molecule can be linked to the HB portion of the composition be any number of known approaches. Many bivalent or polyvalent linking agents are useful in coupling protein molecules to other molecules. For example, representative coupling agents can include organic compounds such as thioesters, carbodiimides, succinimide esters, disocyanates, glutaraldehydes, diazobenzenes and hexamethylene diamines. This listing is not intended to be exhaustive of the various classes of coupling agents known in the art but, rather, is exemplary of the more common coupling agents. See Killen & Lindstrom, 133 J. Immunol 1335 (1984); Jansen et al., 62 Imm Rev. 185 (1982). In some embodiments, cross-linking reagents agents described in the literature are encompassed for use in the HB compositions as disclosed herein. See, e.g., Ramakrishnan, et al., 44 Cancer Res. 201 (1984) (describing the use of MBS (M-maleimidobenzoyl-N-hydroxysuccinimide ester)); Umemoto et al., U.S. Pat. No. 5,030,719 (describing the use of a halogenated acetyl hydrazide derivative coupled to an antibody by way of an oligopeptide linker). Particular linkers include: (a) EDC (1-ethyl-3-(3-dimethylamino-propyl) carbodiimide hydrochloride; (b) SMPT (4-succinimidyloxycarbonyl-alpha-methyl-alpha-(2-pyridyldithio)-toluene (Pierce Chem. Co., Cat. (21558G); (c) SPDP (succinimidyl-6 [3-(2-pyridyldithio) propionamido]hexanoate (Pierce Chem. Co., Cat #21651G); (d) Sulfo-LC-SPDP (sulfosuccinimidyl 6 [3-(2-pyridyldithio)-propianamide]hexanoate (Pierce Chem. Co. Cat. #2165-G); and (f) sulfo-NHS (N-hydroxysulfo-succinimide: Pierce Chem. Co., Cat. #24510) conjugated to EDC.

The linkages or linking agents described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage can be cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

Exemplary cross-linking molecules for use in the methods and compositions as disclosed herein include, but are not limited to those listed in Tables 3 and 4:

TABLE 3

Exemplary homobifunctional crosslinkers (homobifunctional crosslinking reagents that have the same type of reactive group at either end. Reagents are classified by what chemical groups they cross link (left column) and their chemical composition (middle column). Products are listed in order of increasing length within each cell).

| Crosslinking Target | Crosslinker Reactive Groups, Features | Example Products |
|---|---|---|
| Amine-to-Amine | NHS esters | DSG; DSS; BS3; TSAT (trifunctional); Bioconjugate Toolkit Reagent Pairs |
| | NHS esters, PEG spacer | BS(PEG)5; BS(PEG)9 |
| | NHS esters, thiol-cleavable | DSP; DTSSP |
| | NHS esters, misc-cleavable | DST; BSOCOES; EGS; Sulfo-EGS |
| | Imidoesters | DMA; DMP; DMS |
| | Imidoesters, thiol-cleavable | DTBP |
| | Other | DFDNB; THPP (trifunctional); Aldehyde-Activated Dextran Kit |
| Sulfhydryl-to-Sulfhydryl | Maleimides | BMOE; BMB; BMH; TMEA (trifunctional) |
| | Maleimides, PEG spacer | BM(PEG)2; BM(PEG)3 |
| | Maleimides, cleavable | BMDB; DTME |
| | Pyridyldithiols (cleavable) | DPDPB |
| | Other | HBVS (vinylsulfone) |
| Nonselective | Aryl azides | BASED (thiol-cleavable) |

TABLE 4

Exemplary heterobifunctional crosslinkers (heterobifunctional crosslinking reagents that have the different reactive groups at either end. Reagents are classified by what chemical groups they cross link (left column) and their chemical composition (middle column). Products are listed in order of increasing length within each cell.)

| Crosslinking Targets | Crosslinker Reactive Groups, Features | Example Products |
|---|---|---|
| Amine-to-Sulfhydryl | NHS ester/Maleimide | AMAS; BMPS; GMBS and Sulfo-GMBS; MBS and Sulfo-MBS; SMCC and Sulfo-SMCC; EMCS and Sulfo-EMCS; SMPB and Sulfo-SMPB; SMPH; LC-SMCC; Sulfo-KMUS |
| | NHS ester/Maleimide, PEG spacer | SM(PEG)2; SM(PEG)4; SM(PEG)6; SM(PEG)8; SM(PEG)12; SM(PEG)24 |
| | NHS ester/Pyridyldithiol, cleavable | SPDP; LC-SPDP and Sulfo-LC-SPDP; SMPT; Sulfo-LC-SMPT |
| | NHS esters/Haloacetyl | SIA; SBAP; SIAB; Sulfo-SIAB |
| Amine-to-Nonselective | NHS ester/Aryl Azide | NHS-ASA ANB-NOS Sulfo-HSAB Sulfo-NHS-LC-ASA SANPAH and Sulfo-SANPAH |
| | NHS ester/Aryl Azide, cleavable | Sulfo-SFAD; Sulfo-SAND; Sulfo-SAED |
| | NHS ester/Diazirine | SDA and Sulfo-SDA; LC-SDA and Sulfo-LC-SDA |
| | NHS ester/Diazirine, cleavable | SDAD and Sulfo-SDAD |
| Amine-to-Carboxyl | Carbodiimide | DCC; EDC |
| Sulfhydryl-to-Nonselective | Pyridyldithiol/Aryl Azide | APDP |
| Sulfhydryl-to-Carbohydrate | Maleimide/Hydrazide | BMPH; EMCH; MPBH; KMUH |
| | Pyridyldithiol/Hydrazide | BMPH; EMCH; MPBH; KMUH |
| Carbohydrate-to-Nonselective | Hydrazide/Aryl Azide | ABH |
| Hydroxyl-to-Sulfhydryl | Isocyanate/Maleimide | PMPI |
| Amine-to-DNA | NHS ester/Psoralen | SPB |

The small molecules, and where relevant the fusion proteins, of the HB-X compositions can include pro-drugs. The term "pro-drug" refers to any compound which releases an active parent drug in vivo when such pro-drug is administered to a mammalian subject. Pro-drugs of a compound are typically prepared by modifying one or more functional group(s) present in the compound in such a way that the modification(s) may be cleaved in vivo to release the parent compound. Examples of pro-drugs include, but are not limited to, esters (e.g., acetate, formate, and benzoate derivatives) and carbamates (e.g., N,N-dimethylaminocarbonyl) of hydroxy functional groups, and amides, carbamates and urea derivatives of amino functional groups, and the like. Pro-drug forms often offer advantages of solubility, tissue compatibility, or delayed release in the mammalian organism. See Bundgard, DESIGN PRODRUGS, 7, 21 (Elsevier, Amsterdam, 1985); Silverman, ORGANIC CHEMISTRY DRUG DESIGN & DRUG ACTION, 352 (Academic Press, San Diego, Calif.). Moreover, the pro-drug derivatives of the invention may be combined with other features known to one skilled in the art to enhance bioavailability.

HB-X Conjugates in Method of Treatment

Another aspect of the present invention relates to a method of treating a cartilage-related condition (e.g., damage or disease) comprising administering to a subject an effective amount of a HB-X conjugate, such as, for example, a recombinant fusion protein comprising HB-X$_n$ or (HB-linker)$_n$-X$_n$, wherein X is an active agent. In some embodiments, an active agent for the treatment of a cartilage-related condition is a therapeutic protein. In some embodiments, therapeutic protein a selected from Parathyroid hormone (PTH); Parathyroid hormone related peptide (PTHrP); Interleukin 1 receptor antagonist (IL-1RA); Fibroblast growth factor 18 (FGF-18), an anti-nerve growth factor antibody; Fibroblast growth factor 9 (FGF-9); Hepatocyte growth factor; TGFβ-superfamily proteins such as TGFβ, TGFβ3, BMP2, or BMP7; or portions, analogs, derivatives or functional fragments thereof.

In some embodiments, a HB-X conjugate for the treatment of a cartilage-related condition can comprise at least one parathyroid hormone (PTH) therapeutic protein, e.g., one selected from any protein or functional fragment thereof selected from the group of: SEQ ID NO: 32-37.

In some embodiments, a HB-X conjugate for the treatment of a cartilage-related condition can comprise at least one therapeutic protein, e.g., one selected from any protein or functional fragment thereof selected from the group of: IGF-1 or variants or functional fragments thereof (SEQ ID NO: 6-9, SEQ ID NO: 63); FGF-18 (SEQ ID NO: 31); PTH or variants or functional fragments thereof (SEQ ID NO: 32-37); PTHrP (SEQ ID NO: 38, 39); IL-1 RA or IL-1/IL-1 RA chimeras (SEQ ID NO: 40); HMG (SEQ ID NO: 824-0; SST (SEQ ID NO: 72): ANGPTL3 or variants or functional fragments thereof (SEQ ID NO: 73-76); –41, SEQ ID NO: 63 and SEQ ID NO: 73-76, or functional fragments thereof.

In some embodiments, a HB-X conjugate for the treatment of a cartilage-related condition can comprise at least one small molecule, e.g., but not limited to a SST agonist, e.g., octreotide, pasireotide, or lamreotide. In some embodiments, a HB-X conjugate as disclosed herein comprising a IGF-1 protein or functional fragment or variant thereof (e.g., SEQ ID NO: 6-9 or SEQ ID NO: 63) can be used for the treatment of a subject with dwarfism and/or a related condition with delayed growth.

Another aspect of the present invention relates to a method of treating a cartilage-related condition (e.g., damage or disease) comprising administering to a subject an amount of a HB-X conjugate, such as, for example, a recombinant fusion protein comprising HB-Xn or (HB-linker)n-Xn, where X is a Glucocorticoid receptor; and further administering concurrently or separately a Corticosteroid.

In some embodiments, a cartilage-related condition is a articular cartilage defect including rupture or detachment, a meniscal defect including a partial or complete tear, Osteoarthritis, Traumatic cartilage rupture or detachment, disease or damage to the meniscus and/or patella, Ankylosing spondylitis, Capsulitis, Psoriatic arthritis, Rheumatoid arthritis, Systemic lupus erythematosus, Juvenile idiopathic arthritis, or X-linked hypophosphatemic rickets.

In some embodiments, a cartilage-related condition is a rupture or detachment of the cartilage, a meniscal defect including a partial or complete tear or damage or a disease effecting the meniscus and/or patella. In some embodiments, a cartilage-related condition is selected from any or a combination of diseases from the following group: osteoarthritis (referred to herein as "OA" which results from breakdown of cartilage), including knee, finger, wrist, hip, ankle, elbow, toe, shoulder, and spinal osteoarthritis, traumatic cartilage rupture or detachment, ankylosing spondylitis, capsulitis, psoriatic arthritis, rheumatoid arthritis (RA), systemic lupus erythematosus, juvenile idiopathic arthritis, Chondropathy, Chondrosarcoma, Chondromalacia, Polychondritis, Relapsing Polychondritis, Slipped epiphysis, Osteochondritis Dissecans, Chondrodysplasia, Costochondritis, X-linked hypophosphatemic rickets, Osteochondroma, Chondrosarcoma (malignant), Osteoarthritis Susceptibility (types 1-6), Spondylosis, Osteochondroses, Primary chondrosarcoma, Chondrodysplasia, Tietze syndrome, Dermochondrocorneal dystrophy of Francois, Epiphyseal dysplasia, multiple, (types 1-5), Ossified Ear cartilages with Mental deficiency, Muscle Wasting and Bony Changes, Carpotarsal osteochondromatosis, Achondroplasia, Chondrocalcinosis (types 1-2), Genochondromatosis, Chondrodysplasia (disorder of sex development), Chondroma, Achondrogenesis (types 1A, 1B, 2, 3, 4, Langer-Saldino Type), Type II Achondrogenesis-Hypochondrogenesis, Atelosteogenesis, (type 1, 2 and III), Pyknoachondrogenesis, Pseudoachondroplasia, Osteoarthropathy of fingers, familial, Diastrophic dysplasia, Dyschondrosteosis—nephritis, Coloboma of Alar-nasal cartilages with telecanthus, Alar cartilages hypoplasia—coloboma—telecanthus, Pierre Robin syndrome—fetal chondrodysplasia, Dysspondyloenchondromatosis, Achondroplasia regional—dysplasia abdominal muscle, Osteochondritis Dissecans, Familial Articular Chondrocalcinosis, Tracheobronchomalacia, Chondritis, Dyschondrosteosis, Maffucci Syndrome, Jequier-Kozlowski-skeletal dysplasia, Chondrodystrophy, Cranio osteoarthropathy, Tietze's syndrome, Hip dysplasia—enchondromata—enchondromata, Bessel-Hagen disease, Chondromatosis (benign), Enchondromatosis (benign), chondrocalcinosis due to apatite crystal deposition, Meyenburg-Altherr-Uehlinger syndrome, Enchondromatosis-dwarfism-deafness, Astley-Kendall syndrome, Synovial osteochondromatosis, Chondrocalcinosis familial articular, Severe achondroplasia with developmental delay and acanthosis nigricans, Chondrocalcinosis, Keutel syndrome, Stanescu syndrome, Fibrochondrogenesis, Hypochondroplasia.

A subject amenable for the treatment with a HB-X conjugate for the treatment of a cartilage-related condition is selected from a subject who has one or more symptoms of a joint disorder or cartilage loss or damage, including one or more symptoms from the group of: joint swelling, joint pain, joint redness, joint laxity, mild arthritis symptoms, haemorrhagic joint effusion, inflammatory joint effusion, joint hypermobility, non inflammatory joint effusion or other types.

In some embodiments, a subject is selected for administration of a composition comprising a HB-X conjugate for the treatment of a cartilage-related condition is a subject who has familial osteochondritis dissecans, where the subject has a mutation of the ACAN gene. The ACAN gene provides instructions for making the aggrecan protein, which is a component of cartilage. Aggrecan attaches to the other components of cartilage, organizing the network of molecules that gives cartilage its strength. In addition, aggrecan attracts water molecules and gives cartilage its gel-like structure. This feature enables the cartilage to resist compression, protecting bones and joints. The ACAN gene mutation associated with familial osteochondritis dissecans results in an abnormal protein that is unable to attach to the other components of cartilage. As a result, the cartilage is abnormal and disorganized and weak and leads to the lesions and osteoarthritis characteristic of familial osteochondritis dissecans.

In some embodiments, a subject is selected for administration of a composition comprising a HB-X conjugate for the treatment of a cartilage-related condition has an osteopenic related disease or osteoporosis, e.g., associated with the peri and post menopausal conditions. Also encompassed are the treatment and prophylaxis of Paget's disease, hypercalcemia associated with bone neoplasms and all the types of osteoporotic diseases as classified below according to their etiology: Primary osteoporosis, hypercalcemia, involutional osteoporosis, Type I or postmenopausal osteoporosis, Type II or senile osteoporosis, Juvenile osteoporosis, Idiopathic in young adults osteoporosis, Secondary osteoporosis, Endocrine abnormality, Hyperthyroidism, Hypogonadism, Ovarian agenesis, or Turner's syndrome, Hyperadrenocorticism or Cushing's syndrome, Hyperparathyroidism, Bone marrow abnormalities, Multiple myeloma and related disorders, and Systemic mastocytosis, disseminated carcinoma osteoporosis, Gaucher's disease, Connective tissue abnormalities, Osteogenesis imperfecta, Homocystinuria, Ehlers-Danlos syndrome, Marfan's syndrome, Menke's syndrome, Miscellaneous causes Immobilisation or weightlessness, Sudeck's atrophy, chronic obstructive pulmonary disease, chronic alcoholism, chronic heparin administration and chronic ingestion of anticonvulsant drugs Patients amenable to treatment with a composition comprising a HB-X conjugate for the treatment of a cartilage-related condition as disclosed herein include patients at risk of disease but not showing symptoms (for example asymptomatic patients), as well as patients presently showing symptoms. In the case of OA or osteoporosis, virtually anyone, particularly women are at risk of suffering from OA and osteoporosis if he or she lives long enough.

In some embodiments, a subject is selected for administration of a composition comprising a HB-X conjugate for the treatment of a cartilage-related condition is a subject known to have a genetic risk of a cartilage-related disease or disorder, e.g., OA. In some embodiments, patients are women, for example post menopausal, or women at least 65 years of age, or patients who have had previous fractures or have relatives who have had a metabolic bone disease, for example osteoporosis. Patients can be identified as having increased risk of developing metabolic bone disease using methods commonly known by person of ordinary skill in the art.

In some embodiments, a subject is selected for administration of a composition comprising a HB-X conjugate for the treatment of a cartilage-related condition has at least one of the following conditions; rheumatoid arthritis (RA), Juvenile Rheumatoid Arthritis (JRA), psoriatic arthritis, Reiter's syndrome (reactive arthritis), Crohn's disease, ulcerative colitis and sarcoidosis (Orcel, et al., Bone demineralization and cytokines; Rev Rhum Mal Osteoartic. 1992; 59:16S-22S; Brown, et al., The radiology of rheumatoid arthritis. Am Fam Physician. 1995. 52:1372-80; De Vos, et al., Bone and joint diseases in inflammatory bowel disease. Aliment Pharmacol Ther. 1998; 12(5):397-404; Falcini, et al., The primary role of steroids on the osteoporosis in juvenile rheumatoid patients evaluated by dual energy X-ray absorptiometry. J Endocrinol Invest. 1996; 19(3):165-9; Scutellari, et al., Rheumatoid arthritis: sequences. Eur J Radiol. 1998: Suppl 1:S31-8).

Rheumatoid arthritis is associated with a decrease in bone mass (Cortet, et al., Evaluation of bone mineral density in patients with rheumatoid arthritis. Influence of disease activity and glucocorticoid therapy. Rev Rhum Engl Ed. 1997 Jul.-Sep. 30, 1997; 64(7-9):451-8). Typical changes of an inflammatory arthritis include juxta-articular osteoporosis, cartilage loss, and cortical or marginal bone erosions (Lawson, et al., Lyme arthritis: radiologic findings. Radiology. 1985; 154(1):37-43; Grassi, et al., The clinical features of rheumatoid arthritis. Eur J Radiol. 1998; 1:S18-24).

In some embodiments, a subject is selected for administration of a composition comprising a HB-X conjugate for the treatment of a cartilage-related condition who has a chronic inflammatory joint disease, such as rheumatoid arthritis, synovial cells produce large amounts of cytokines leading to increased local bone resorption and juxta-articular bone destructions (Orcel, P et al., Bone demineralization and cytokines. Rev Rhum Mal Osteoartic. 1992; 59(6 Pt 2):16S-22S).

Another aspect of the present invention relates to a method of treating a neurological condition (e.g., a disorder or disease) comprising administering to a subject an amount of a HB-X conjugate, such as, for example, a recombinant fusion protein comprising $HB-X_n$ or $(HB-linker)_n-X_n$, where X is a therapeutic protein selected from nerve growth factor (NGF), brain-derived neurotrophic factor (BDNF), neurotrophin-3 (NT-3), neurotrophin-4 (NT-4), Ciliary neurotrophic factor (CNTF), mesencephalic astrocyte-derived neurotrophic factor (MANF), conserved dopamine neurotrophic factor (CDNF), glial cell line-derived neurotrophic factor (GDNF), neurturin (NRTN), artemin (ARTN), persephin (PSPN), interleukin-6, interleukin-11, interleukin-27, leukaemia inhibitory factor, ciliary neurotrophic factor, cardiotrophin 1, neuropoietin, cardiotrophin-like cytokine, FPF-1070, Fibroblast Growth Factor 2, Neuregulin-1, Vascular endothelial growth factor (VEGF), or a functional portion, analog, or derivative thereof.

In some embodiments, a neurological condition to be treated is selected from the group of neurological diseases selected from Alzheimer's disease, Parkinson's disease, Amyotrophic lateral sclerosis, Multiple sclerosis, Brain injury, Spinal cord injury, Peripheral nerve degeneration, Stroke, Huntington's disease, Pick's disease, Diabetic neuropathy, Frontotemporal dementia, Dementia with Lewy bodies, Corticobasal degeneration, Progressive supranuclear palsy, Prion disorders, Progressive supranuclear palsy, Multiple system atrophy, Hereditary spastic paraparesis, Spinocerebellar atrophies, Friedreich's ataxia, Amyloidoses, or Charcot Marie Tooth syndrome.

Accordingly, in some embodiments, a subject is selected for administration of a composition comprising a HB-X conjugate for the treatment of a neurological disease or disorder who has at least one of the following diseases and disorders, including, but not limited to Alzheimer's disease (AD), Parkinson's disease (PD), Huntington's disease (HD), vascular dementia, aging and mild-cognitive impairment. In some embodiments, a subject selected for treatment has a neurodegenerative disorder is selected from the group consisting of: Alzheimer's disease and Parkinson disease.

In some embodiments, a subject is selected for treatment who has a neurological disorder such as: hyperosmolarity; acidic pH; burn encephalopathy; lead encephalopathy; autoimmune encephalitis; multiple sclerosis; post-ischemia reperfusion; acute hypertension; microwave irradiation; hepatic encephalopathy; seizures; tumors; development; hypervolemia; hypothermia; post-radiation; hyperbaric conditions; meningitis; lymphostatic encephalopathy; Wernickes-Korsakoff syndrome; familial mental retardation and amyotrophic lateral sclerosis (ALS).

Subjects amenable to treatment with a composition comprising a HB-X conjugate for the treatment of a neurological disease or disorder as disclosed herein include subjects at risk of disease but not showing symptoms (for example asymptomatic subjects), as well as subjects presently showing symptoms. In the case of Alzheimer's disease, virtually anyone is at risk of suffering from Alzheimer's disease if he or she lives long enough. Therefore, the present methods can be administered prophylactically to the general population without any assessment of the risk of the subject patient. The methods as disclosed herein are especially useful for individuals who do have a known genetic risk of Alzheimer's disease. Such individuals include those having relatives who have experienced this disease, and those whose risk is determined by analysis of genetic or biochemical markers, as disclosed herein.

Alzheimer's disease (AD) is a progressive disease resulting in senile dementia. See generally Selkoe, TINS 16, 403-409 (1993); Hardy et al., WO 92/13069; Selkoe, J. Neuropathol. Exp. Neurol. 53, 438-447 (1994); Duff et al., Nature 373, 476-477 (1995); Games et al., Nature 373, 523 (1995). Broadly speaking the disease falls into two categories: late onset, which occurs in old age (65+ years) and early onset, which develops well before the senile period, i.e., between 35 and 60 years. In both types of disease, the pathology is the same but the β abnormalities tend to be more severe and widespread in cases beginning at an earlier age. The disease is characterized at the macroscopic level by significant brain shrinkage away from the cranial vault as seen in MRI images as a direct result of neuronal loss and by two types of macroscopic lesions in the brain, senile plaques and neurofibrillary tangles. Senile plaques are areas comprising disorganized neuronal processes up to 150 μm across and extracellular amyloid deposits, which are typically concentrated at the center and visible by microscopic analysis of sections of brain tissue. Neurofibrillary tangles are intracellular deposits of tau protein consisting of two filaments twisted about each other in pairs.

Genetic markers of risk toward Alzheimer's disease include mutations in the APP gene, particularly mutations at position 717 and positions 670 and 671 referred to as the Hardy and Swedish mutations respectively (see Hardy, TINS, supra). Other markers of risk are mutations in the presenilin genes, PS1 and PS2, and ApoE4, family history of Alzheimer's disease, hypercholesterolemia or atherosclerosis. Subjects presently suffering from Alzheimer's disease can be recognized from characteristic dementia, as well as the presence of risk factors described above. In addition, a number of diagnostic tests are available for identifying subjects who have Alzheimer's disease. These include measurement of CSF tau and Aβ42 levels. Elevated tau and increased Aβ42 levels signify the presence of Alzheimer's disease. Individuals suffering from Alzheimer's disease can also be diagnosed by MMSE or ADRDA criteria. The tissue sample for analysis is typically blood, plasma, serum, mucus or cerebral spinal fluid from the patient. The sample is analyzed for indicia of an immune response to any forms of Aβ peptide, typically Aβ 42. The immune response can be determined from the presence of, e.g., antibodies or T-cells that specifically bind to Aβ peptide. ELISA methods of detecting antibodies specific to Aβ are commonly known to one of ordinary ski; in the art.

In asymptomatic patients, treatment can begin at any age (e.g., 10, 20, 30). Usually, however, it is not necessary to begin treatment until a patient reaches 40, 50, 60 or 70. Treatment typically entails multiple dosages over a period of time. Treatment can be monitored by assaying presence of Aβ peptide in the CSF. If the Aβ peptide is still present in the CSF, additional treatment with a HB-X conjugate for a neurodegenerative disease as disclosed herein are recommended, and/or treatment of additional therapies for Alzheimer's disease. In the case of potential Down's syndrome patients, treatment can begin antenatally by administering therapeutic agent to the mother or shortly after birth.

In some embodiments, a composition comprising a HB-X conjugate for the treatment of a neurological disease or disorder as disclosed herein are also useful in the treatment of other neurodegenerative disorders or cognitive impairment disorders in general: for example, dementia, depression, confusion, Creutzfeldt-Jakob or mad cow disease, Huntington's disease, loss of motor coordination, multiple sclerosis, Parkinson's disease, Pick disease and other brain storage disorders (e.g., amyloidosis, gangliosidosis, lipid storage disorders, mucopolysaccharidosis), syncope, and vascular dementia. Thus, treatment can be directed to a subject who is affected with unsymptomatic by the neurodegenerative disease; it can improve cognitive function.

Another aspect of the present invention relates to a method of treating an eye disorder or disease comprising administering to a subject an amount of a HB-X conjugate, such as, for example, a recombinant fusion protein comprising HB-$X_n$ or (HB-linker)$_n$-$X_n$, where X is a therapeutic protein selected from nerve growth factor (NGF), brain-derived neurotrophic factor (BDNF), neurotrophin-3 (NT-3), neurotrophin-4 (NT-4), Ciliary neurotrophic factor (CNTF), mesencephalic astrocyte-derived neurotrophic factor (MANF), conserved dopamine neurotrophic factor (CDNF), glial cell line-derived neurotrophic factor (GDNF), neurturin (NRTN), artemin (ARTN), persephin (PSPN), interleukin-6, interleukin-11, interleukin-27, leukaemia inhibitory factor, ciliary neurotrophic factor, cardiotrophin 1, neuropoietin, cardiotrophin-like cytokine, FPF-1070, Fibroblast Growth Factor 2, Neuregulin-1, Vascular endothelial growth factor (VEGF), or a functional portion, analog, or derivative thereof.

In some embodiments, a subject is selected for treatment with a composition comprising HB-X for the treatment of an eye disease or disorder has one or more eye disease from the following: Corneal ulcer/Corneal abrasion, Thygeson's superficial punctate keratopathy, Corneal neovascularization, Fuchs' dystrophy, Keratoconjunctivitis sicca, Chorioretinal inflammation, Chorioretinal scars, Choroidal degeneration, Hereditary choroidal dystrophy, Retinal detachment, Retinoschisis, Hypertensive retinopathy, Retinopathy of prematurity, Age-related macular degeneration (AMD), Retinal degeneration, Macular degeneration, Epiretinal membrane, Peripheral retinal degeneration, Hereditary retinal dystrophy, Retinitis pigmentosa, Xerophthalmia, or Retinal haemorrhage.

In some embodiments, a subject is selected for treatment with a composition comprising HB-X for the treatment of an eye disease or disorder has one or more eye disease from the following: but not limited to diabetic retinopathy, retinopathy of prematurity (ROP), age-related macular degeneration (AMD), retinal vein occlusion, radiation retinopathy. In some embodiments, a subject is selected for treatment with a composition comprising HB-X for the treatment of an eye disease or disorder who has an "inflammation-mediated condition of the eye", which refers to herein as any condition of the eye which may benefit from treatment with an anti-inflammatory agent, and is meant to include, but is not limited to, uveitis, macular edema, acute macular degeneration, retinal detachment, ocular tumors, fungal or viral infections, multifocal choroiditis, diabetic uveitis, proliferative vitreoretinopathy (PVR), sympathetic opthalmia, Vogt Koyanagi-Harada (VKH) syndrome, histoplasmosis, and uveal diffusion.

Another aspect of the present invention relates to a method of treating inflammation in a subject comprising administering to a subject an amount of a HB-X conjugate, such as, for example, a recombinant fusion protein comprising HB-Xn or (HB-linker)n-Xn, where X is a therapeutic protein or a portion thereof, selected from TNF receptor 2, interleukin-4, or interleukin-10.

In some embodiments, a composition comprising HB-X for the treatment of inflammation comprises a cytokine (e.g., a anti-inflammatory cytokine) or chemokine as an active agent.

As used herein, a "cytokine" is a generic term for proteins released by any of the lymph cells that act on other cells as intercellular mediators and affect cellular activity and control inflammation. Cytokines are typically soluble proteins or peptides which are naturally produced by mammalian cells and which act in vivo as humoral regulators at micro- to picomolar concentrations. Cytokines can, either under normal or pathological conditions, modulate the functional activities of individual cells and tissues. An anti-inflammatory cytokines, such as IL-4, IL-10, IL-11, W-13, IL-13 and TGFβ, are not mediators of inflammation. Additionally examples of cytokines include, lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance (MIS); mouse gonadotropin-associated peptide; inhibin; activin; vascular endothelial growth factor (VEGF); integrin; thrombopoietin (TPO); nerve growth factors such as NGF-13; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as, for example and not for limitation, IL-1, IL-1α, IL-1β, IL-2, IL-3, IL-4, IL-5, IL-6, IL-7, IL-8, IL-9, IL-10, IL-11, IL-12; a tumor necrosis factor such as TNF-α or TNF-β; and other polypeptide factors including leukemia inhibitory factor (LIF) and kit ligand (KL).

The term "chemokine" is a generic term for any of the proteins that act on white blood cells and induce them to move and/or become activated to carry out their immune system functions. Chemokines are well-known in the art. Exemplary chemokines include, for example and not for limitation, TECK, ELC, BLC-1, CTACK, RANTES, fractalkine, exotaxin, eotaxin-2, Monocyte chemoattractant protein-1 (MCP-1), MCP-2, MCP-3, MCP-4, MDC, leukotactin, SDF-1β, lymphotactin, TARC, ITAC, ENA-70, ENA-78, IP-10, NAP-2, interleukin-8 (IL-8), HCC-1, MIP-1α, MIP-1β, MIP-1δ, I-309, GRO-α, GRO-β, GRO-γ, MPIF-1, I-LINK, and GCP-2.

In some embodiments, a composition for the treatment of a subject with dwarfism and/or a related condition with delayed growth comprises an active agent which is a IGF-1 protein or functional fragment or variant thereof (e.g., SEQ ID NO: 6-9 or SEQ ID NO: 63).

In some embodiments, a composition comprising HB-X for the treatment of inflammation in a subject comprises an active agent which is a steroidal anti-inflammatory agent. Preferably, the steroidal anti-inflammatory agent is selected from the group consisting of 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, fluclorinide, flumethasone, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, and triamcinolone hexacetonide. In a preferred embodiment, the steroidal anti-inflammatory agent is selected from the group consisting of cortisone, dexamethasone, hydrocortisone, methylprednisolone, prednisolone, prednisone, and triamcinolone. In a more preferred embodiment, the steroidal anti-inflammatory agent is dexamethasone. In another embodiment, the bioerodible implant comprises more than one steroidal anti-inflammatory agent.

In some embodiments, a composition comprising HB-X for the treatment of inflammation comprises an anti-inflammatory agent. Preferably the anti-inflammatory agent is selected from the group consisting of: an analgesic; an anti-rheumatic agent; an gastrointestinal agent; a gout preparation; glucocorticoids; opthalmic preparation; respiratory agent; a nasal preparation; and a mucous membrane agent.

In some embodiments, a subject is selected for treatment with a composition comprising HB-X for the treatment of an inflammation or an inflammatory-related disease or disorder has one or more of the inflammatory-related diseases from the following: arthritis, rheumatoid arthritis, an inflammatory bowel disease; psoriasis; multiple sclerosis; a neurodegenerative disorder; congestive heart failure; stroke; aortic valve stenosis; kidney failure; lupus; pancreatitis; allergy; fibrosis; anemia; atherosclerosis; a metabolic disease; a bone disease; a cardiovascular disease, a chemotherapy/radiation related complication; diabetes type I; diabetes type II; a liver disease; a gastrointestinal disorder; an ophthamological disease; allergic conjunctivitis; diabetic retinopathy; Sjogren's syndrome; uvetitis; a pulmonary disorder, arenal disease; dermatitis; HIV-related cachexia; cerebral malaria; ankylosing spondolytis; leprosy; anemia; and fibromyalgia.

In some embodiments, a subject is selected for treatment with a composition comprising HB-X for the treatment of an inflammation or an inflammatory-related disease has inflammatory bowel disease (IBD), specifically including Crohn's disease and uncerative colitis. In another embodiment the disease being treated is arthritis, rheumatoid arthritis, psoriasis, Alzheimer's disease, or Parkinson disease. In yet another preferred embodiment the disease is post-radiotherapy related disease or atherosclerosis.

In some embodiments, a subject is selected for treatment with a composition comprising HB-X for the treatment of an inflammation or an inflammatory-related disease has inflammatory bowel disease selected from the group consisting of: Crohn's disease or uncerative colitis; a gastrointestinal complication such as diarrhea; a liver disease is selected from the group consisting of: an autoimmune hepatitis, hepatitis C, primary biliary cirrhosis, primary sclerosing cholangitis, or fulminant liver failure; a gastrointestinal disorder selected from the group consisting of: celiac disease and non-specific colitis; a bone disease is osteoporosis; the pulmonary disorder is selected from the group consisting of: allergic rihinitis, asthma, chronic obstructive pulmonary disease, chronic granulomatous inflammation, cystic fibrosis, and sarcoidosis; a cardiovascular disease selected from the group consisting of: atheroscleotic cardiac disease, congestive heart failure and restenosis; and a renal disease selected from the group consisting of: glomerulpnephritis and vasculitis.

In some embodiments, a subject selected for treatment with a composition comprising HB-X for the treatment of inflammation has an auto-immune disease. In some embodiments, a subject to be treated with a composition comprising HB-X for the treatment of inflammation or auto-immune disease has one or more of the following conditions from the following: rheumatoid arthritis, multiple sclerosis (MS), systemic lupus erythematosus (SLE), autoimmune myocarditis, sepsis, Graves' disease (overactive thyroid), Hashimoto's thyroiditis (underactive thyroid), Type 1 diabetes mellitus, celiac disease, Crohn's disease and ulcerative colitis, Guillain-Barre syndrome, primary biliary sclerosis/cirrhosis, sclerosing cholangitis, autoimmune hepatitis, Raynaud's phenomenon, scleroderma, Sjogren's syndrome, Goodpasture's syndrome, Wegener's granulomatosis, polymyalgia rheumatica, temporal arteritis/giant cell arteritis, chronic fatigue syndrome CFS), psoriasis, autoimmune Addison's Disease, ankylosing spondylitis, Acute disseminated encephalomyelitis, antiphospholipid antibody syndrome, aplastic anemia, idiopathic thrombocytopenic purpura, Myasthenia gravis, opsoclonus myoclonus syndrome, optic neuritis, Ord's thyroiditis, pemphigus, pernicious anaemia, polyarthritis in dogs, Reiter's syndrome, Takayasu's arteritis, warm autoimmune hemolytic anemia, Wegener's granulomatosis and fibromyalgia (FM). Chronic inflammation recently has received interest as a suspected cause and/or as a contributory factor in a variety of disease conditions. Perhaps most prominent among such conditions are cardiovascular diseases, although cancers, similarly, are often viewed as being developmentally related to chronic inflammation.

Administration of Pharmaceutical Compositions

An effective amount, e.g., a therapeutically effective dose of an HB-X conjugate comprising a therapeutic protein or peptide may be administered to the patient in a single dose or in multiple doses. When multiple doses are administered, the doses may be separated from one another by, for example, one hour, three hours, six hours, eight hours, one day, two days, one week, two weeks, or one month. For example, a composition comprising HB-X can be administered for, e.g., 2, 3, 4, 5, 6, 7, 8, 10, 15, 20, or more weeks. It is to be understood that, for any particular subject, specific dosage regimes should be adjusted over time according to the individual need and the professional judgment of the person administering or supervising the administration of the compositions. For example, the dosage of the therapeutic can be increased if the lower dose does not provide sufficient therapeutic activity.

While the attending physician ultimately will decide the appropriate amount and dosage regimen, an effective amounts of a HB-X can provided at a dose of 0.0001, 0.01, 0.01 0.1, 1, 5, 10, 25, 50, 100, 500, or 1,000 mg/kg. Effective doses may be extrapolated from dose-response curves derived from in vitro or animal model test bioassays or systems.

Dosages for a particular patient or subject can be determined by one of ordinary skill in the art using conventional considerations, (e.g. by means of an appropriate, conventional pharmacological protocol). A physician may, for example, prescribe a relatively low dose at first, subsequently increasing the dose until an appropriate response is obtained. The dose administered to a patient is sufficient to effect a beneficial therapeutic response in the patient over time, or, e.g., to reduce symptoms, or other appropriate activity, depending on the application. The dose is determined by the efficacy of the particular formulation, and the activity, stability or serum half-life of the active agent X e.g., the therapeutic peptide or protein as disclosed herein, and the condition of the patient, the disease to be treated, as well as the body weight or surface area of the patient to be treated. The size of the dose is also determined by the existence, nature, and extent of any adverse side-effects that accompany the administration of a particular vector, formulation, or the like in a particular subject. Therapeutic compositions comprising HB-X thereof are optionally tested in one or more appropriate in vitro and/or in vivo animal models of disease, such a cartilage assay as disclosed herein, or other models commonly known to persons of ordinary skill in the art, to confirm efficacy, tissue metabolism, and retention in the tissue over time, and to estimate dosages, according to methods well known in the art. In particular, dosages can be initially determined by activity, stability or other suitable measures of treatment vs. non-treatment (e.g., comparison of treated vs. untreated cells or animal models), in a relevant assay. Formulations are administered at a rate determined by the LD50 of the relevant formulation, and/or observation of any side-effects of HB-X at various concentrations, e.g., as applied to the mass and overall health of the patient. Administration can be accomplished via single or divided doses.

In determining the effective amount of HB-X to be administered in the treatment or prophylaxis of a disease, the physician evaluates circulating plasma levels, formulation toxicities, and progression of the disease. The selected dosage level will also depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

In some embodiments, HB-X as disclosed herein can be administered at a dose in accordance with good medical practice, taking into account the clinical condition of the individual patient, the site and method of administration, scheduling of administration, patient age, sex, body weight and other factors known to medical practitioners.

Dosage regimens of a composition comprising HB-X as disclosed herein can be adjusted to provide the optimum desired response (e.g. a therapeutic or prophylactic response). For example, a single bolus can be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage.

Furthermore, actual dosage levels of HB-X in a pharmaceutical composition can be varied so as to obtain an amount of the active ingredient which is effective to achieve the desired therapeutic response for a particular subject, composition, and mode of administration, without being toxic to the subject. A pharmaceutical composition comprising HB-X as disclosed herein can be a "therapeutically effective amount" and/or a "prophylactically effective amount". In general, a suitable daily dose of a composition comprising HB-X as disclosed herein will be that amount of the active agent X which is the lowest dose effective to produce a therapeutic effect, such as a reduction of a symptom of a disease for which the HB-X is being administered for. Such an effective dose will generally depend upon the factors described above.

If desired, the effective daily dose of a composition comprising HB-X can be administered as two, three, four, five, six or more sub-doses administered separately at appropriate intervals throughout the day, optionally, in unit dosage forms.

It is to be noted that dosage values may vary with the type and severity of the disease to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The efficacy and toxicity of the compound can be determined by standard pharmaceutical procedures in cell cultures or experimental animals, e.g., ED50 (the dose is effective in 50% of the population) and LD50 (the dose is lethal to 50% of the population). The dose ratio of toxic to therapeutic effects is the therapeutic index, and it can be expressed as the ratio, LD50/ED50. Pharmaceutical compositions which exhibit large therapeutic indices are preferred.

For example, a therapeutically effective amount can be estimated initially either in cell culture assays or in animal models, usually mice, rabbits, dogs, or pigs. The animal model is also used to achieve a desirable concentration range and route of administration. Such information can then be used to determine useful doses and routes for administration in other subjects. Generally, the therapeutically effective amount is dependent of the desired therapeutic effect. For example, the therapeutically effective amount of HB-X for the treatment of a cartilage-related disease or disorder one can be assess the effect of the HB-X, e.g., HB-IGF-1 in an in vivo in a rat model after transection of the medial meniscus (e.g., medial meniscal tear (MMT) surgery) as disclosed herein in the Examples, which is a rat model of surgically induced OA. After injection of the HB-X conjugate (e.g. HB-IGF-1) histological assessment of knee osteoarthritis (OA) is performed and overall OARSI score is determined for the joints of the animals treated with the HB-X conjugate (e.g., HB-IGF-1) is compared to control treated animals, as described herein in the Examples.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. It is also noted that humans are treated generally longer than the mice or other experimental animals exemplified herein, which treatment has a length proportional to the length of the disease process and drug effectiveness. The doses may be single doses or multiple doses over a period of several days, but single doses are preferred.

In some embodiments, HB-X conjugate can be administered to humans and other animals for therapy by any suitable route of administration, including orally, nasally, as by, for example, a spray, rectally, intravaginally, by intra-articular injection, parenterally, intracisternally and topically, as by powders, ointments or drops, including buccally and sublingually.

An HB-X conjugate can be administered by any route known in the art or described herein, for example, oral, parenteral (e.g., intravenously or intramuscularly), intraperitoneal, rectal, cutaneous, nasal, vaginal, inhalant, skin (patch), or ocular. The HB-X conjugate may be administered in any dose or dosing regimen.

In some embodiments, a HB-X conjugate can be administered to a subject as part of a biological implant or transplant. In some embodiments, a biological implant or transplant is incubated with a HB-X conjugate as disclosed herein for a period of time prior to implanting the implant or transplant into the subject. Any biological implant known to one of ordinary skill in the art are encompassed for use herein, for example, but not limited to, osteochondrial or meniscal allografts. In some embodiments, a biological scaffold is incubated with a HB-X conjugate as disclosed herein for a period of time prior to implanting the scaffold into the subject. In some embodiments, the scaffold is a biocompatible and/or biodegradable scaffold.

In some embodiments, a HB-X conjugate is administered to the subject in a hydrogel composition. Any biologically compatible hydrogel composition can be used, e.g., for example, but not limited to, a hydrogel comprising self-assembling peptides. In some embodiments, a hydrogel comprising self-assembling peptides is RADA-16 (also known as PURAMATRIX®) and KLD-12. Self assembly peptide hydrogels are known to one of ordinary skill in the art, such as those described in US Patent Publication Nos: 2013/0129712, 2013/0079421 and EP patent application: EP 1802743 and Kisiday et al., PNAS, 2002; 99(5); 9996-10001, which are each incorporated herein in their entirety by reference.

In some embodiments, a hydrogel may comprise peptides with the sequence RADARADARADARADA (SEQ ID NO: 77) and/or the sequence KLDLKLDLKLDL (SEQ ID NO: 78). In some embodiments, the hydrogel comprises AcN-KLDLKLDLKLDL-CNH2 (SEQ ID NO: 79). Accordingly, in some aspects of the present invention relate to a method for administering a HB-X conjugate to a subject in need thereof, wherein the HB-X conjugate is present in a hydrogel comprising peptides selected from the group of: RADARADARADARADA (SEQ ID NO: 77), KLDLKLDLKLDL (SEQ ID NO: 78) or AcN-KLDLKLDLKLDL-CNH2 (SEQ ID NO: 79). In some embodiments, the present invention relates to a method of treating cartilage-related or meniscus-related clinical condition comprising administering a composition comprising a HB-X and a hydrogel, e.g., a hydrogel comprising peptides selected from the group of: RADARADARADARADA (SEQ ID NO: 77), KLDLKLDLKLDL (SEQ ID NO: 78) or AcN-KLDLKLDLKLDL-CNH2 (SEQ ID NO: 79). In some embodiments, the present invention relates to a method of treating a neuronal disease or disorder comprising administering a composition comprising a HB-X and a hydrogel, e.g., a hydrogel comprising peptides selected from the group of: RADARADARADARADA (SEQ ID NO: 77), KLDLKLDLKLDL (SEQ ID NO: 78) or AcN-KLDLKLDLKLDL-CNH2 (SEQ ID NO: 79).

When the agents or compounds are delivered to a subject, they can be administered by any suitable route, including, for example, orally (e.g., in capsules, suspensions or tablets) or by parenteral administration. Parenteral administration can include, for example, intra-muscular, intravenous, intra-articular, intra-arterial, intrathecal, subcutaneous, or intra-peritoneal administration. The agent can also be administered orally, transdermally, topically, by inhalation (e.g., intra-bronchial, intranasal, oral inhalation or intranasal drops) or rectally. Administration can be local or systemic as indicated. Agents can also be delivered using viral vectors, which are well-known to those skilled in the art. The pharmaceutically acceptable formulations can be suspended in aqueous vehicles and introduced through conventional hypodermic needles or using infusion pumps.

Both local and systemic administration are contemplated by the invention. Desirable features of local administration include achieving effective local concentrations of the active compound as well as avoiding adverse side effects from systemic administration of the active compound. Localized delivery techniques are described in, for example, 51 J. Biomed. Mat. Res. 96 (2000); 100 J. Control Release 211 (2004); 103 J. Control Release 541 (2005); 15 Vet. Clin. North Am. Equine Pract. 603 (1999); 1 Semin. Interv. Cardiol. 17 (1996).

The amount of agent administered to the individual will depend on the characteristics of the individual, such as general health, age, sex, body weight and tolerance to drugs as well as the degree, severity and type of disease as indicated. The skilled artisan will be able to determine appropriate dosages depending on these and other factors.

Accordingly, with respect to the therapeutic methods of the invention, it is not intended that the administration of a HB-X conjugate, e.g., HB-X fusion protein comprising a therapeutic protein or peptide be limited to a particular mode of administration, dosage, or frequency of dosing; the present invention contemplates all modes of administration, including intramuscular, intravenous, intraperitoneal, intravesicular, intraarticular, intralesional, subcutaneous, or any other route sufficient to provide a dose adequate to treat an disease or disorder as disclosed herein.

After formulation with an appropriate pharmaceutically acceptable carrier in a desired dosage, a pharmaceutical composition comprising HB-X as disclosed herein can be administered to a subject. A pharmaceutical a composition comprising HB-X can be administered to a subject using any suitable means. In general, suitable means of administration include, but are not limited to, topical, oral, parenteral (e.g., intravenous, subcutaneous or intramuscular), rectal, intracisternal, intravaginal, intraperitoneal, ocular, or nasal routes.

In a specific embodiment, it may be desirable to administer the pharmaceutical composition comprising HB-X locally to the area in need of treatment; this may be achieved, for example, and not by way of limitation, by local infusion during surgery, topical application, e.g., by injection, by means of a catheter, or by means of an implant, the implant being of a porous, non-porous, or gelatinous material, including membranes, such as sialastic membranes, fibers, or commercial skin substitutes. In some embodiments, HB-X as disclosed herein are applied to the muscle using topical creams, patches, intramuscular injections and the like.

In some embodiments, HB-X can be administered to a subject orally (e.g., in capsules, suspensions or tablets) or by parenteral administration. Conventional methods for oral administration include administering HB-X as a tablets, suspensions, solutions, emulsions, capsules, powders, syrups and the like are usable. Known techniques that deliver HB-X orally or intravenously and retain the biological activity are preferred. Parenteral administration can include, for example, intramuscular, intravenous, intraarticular, intraarterial, intrathecal, subcutaneous, or intraperitoneal administration. HB-X can also be administered orally, transdermally, topically, by inhalation (e.g., intrabronchial, intranasal, oral inhalation or intranasal drops) or rectally. Administration can be local or systemic as indicated. Agents, e.g., nucleic acid agents which encode HB-X can also be delivered using a vector, e.g., a viral vector by methods which are well known to those skilled in the art.

When administering a composition comprising HB-X as disclosed herein parenterally, it will generally be formulated in a unit dosage injectable form (e.g., solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (e.g., glycerol, propylene glycol, liquid polyethylene glycol), suitable mixtures thereof, and vegetable oils.

The term "Dosage unit" form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the HB-X as disclosed herein and the particular therapeutic or prophylactic effect to be achieved, and (b) the limitations inherent in the art of compounding a HB-X as an active for the treatment of sensitivity in individuals.

The pharmaceutically acceptable compositions comprising HB-X as disclosed herein can be suspended in aqueous vehicles and introduced through conventional hypodermic needles or using infusion pumps.

The methods described herein may be used to deliver HB-X to cells, e.g., human cells, in vitro or ex vivo. Alternatively, the method of administering HB-X can be performed on cells present in a subject as part of an in vivo (e.g., therapeutic or prophylactic) protocol. For example, the method can be used to treat or prevent a IGF-1-mediated indication in a subject, such as therapy for cartilage regeneration following injury. Accordingly, the invention provides a method of treating (e.g., curing, suppressing, ameliorating, delaying or preventing the onset of, or preventing recurrence or relapse of) or preventing permanent cartilage loss. The method includes administering to a subject a HB-X composition in an amount sufficient to inhibit or reduce cartilage loss or increase cartilage regeneration, thereby treating or preventing joint degeneration in a subject.

Pharmaceutical Compositions

The compositions of the present invention can be contained in pharmaceutically acceptable formulations. Such a pharmaceutically acceptable formulation may include a pharmaceutically acceptable carrier(s) or excipient(s), solvents, dispersion media, coatings, antibacterial and antifungal agents, isotonic and absorption delaying agents, and the like, that are physiologically compatible. For example, the carrier can be suitable for intra-articular injection. Excipients include pharmaceutically acceptable stabilizers. The present invention pertains to any pharmaceutically acceptable formulations, including synthetic or natural polymers in the form of macromolecular complexes, nanocapsules, microspheres, or beads, and lipid-based formulations including oil-in-water emulsions, micelles, mixed micelles, synthetic membrane vesicles, and gels such as hyaluronic gels.

In some embodiments, a composition comprising HB-X as disclosed herein can be formulated in any suitable means, e.g., as a sterile injectable solution, e.g., which can be prepared by incorporating the HB-X in the required amount of the appropriate solvent with various of the other ingredients, as desired. In some embodiments, a composition comprising HB-X as disclosed herein can be formulated in a hydrogel, for example, but not limited to a hydrogel comprising self-assembling peptides is RADA-16 (also known as PURAMATRIX®) and KLD-12.

A pharmacological formulation of a composition comprising HB-X as disclosed herein can be administered to the patient in an injectable formulation containing any compatible carrier, such as various vehicles, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include those presented in U.S. Pat. Nos. 5,225,182; 5,169,383; 5,167,616; 4,959,217; 4,925,678; 4,487,603; 4,486,194; 4,447,233; 4,447,224; 4,439,196 and 4,475,196. Other such implants, delivery systems, and modules are well known to those skilled in the art.

Proper fluidity can be maintained, for example, by the use of a coating such as lecithin, by the maintenance of the required particle size in the case of dispersion and by the use of surfactants. Non-aqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, e.g., parabens, chlorobutanol, phenol and sorbic acid. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

In another embodiment, a composition comprising HB-X as disclosed herein can comprise lipid-based formulations. Any of the known lipid-based drug delivery systems can be used in the practice of the invention. For instance, multivesicular liposomes, multilamellar liposomes and unilamellar liposomes can all be used so long as a sustained release rate of the encapsulated active compound can be established. Methods of making controlled release multivesicular liposome drug delivery systems are described in PCT Application Publication Nos: WO 9703652, WO 9513796, and WO 9423697, the contents of which are incorporated herein by reference.

The composition of the synthetic membrane vesicle is usually a combination of phospholipids, usually in combination with steroids, especially cholesterol. Other phospholipids or other lipids may also be used. Examples of lipids useful in synthetic membrane vesicle production include phosphatidylglycerols, phosphatidylcholines, phosphatidylserines, phosphatidylethanolamines, sphingolipids, cerebrosides, and gangliosides, with preferable embodiments including egg phosphatidylcholine, dipalmitoylphosphatidylcholine, distearoylphosphatidyleholine, dioleoylphosphatidylcholine, dipalmitoylphosphatidylglycerol, and dioleoylphosphatidylglycerol.

In preparing lipid-based vesicles containing HB-X, such variables as the efficiency of active compound encapsulation, labiality of the active compound, homogeneity and size of the resulting population of vesicles, active compound-to-lipid ratio, permeability, instability of the preparation, and pharmaceutical acceptability of the formulation should be considered.

In another embodiment, the HB-X can be delivered in a vesicle, in particular a liposome (see Langer (1990) Science 249:1527-1533). In yet another embodiment, HB-X can be delivered in a controlled release system. In one embodiment, a pump may be used (see Langer (1990) supra). In another embodiment, polymeric materials can be used (see Howard et al. (1989) J. Neurosurg. 71:105). In another embodiment where the active agent of the invention is a nucleic acid encoding HB-X, the nucleic acid can be administered in vivo to promote expression of its encoded protein, by constructing it as part of an appropriate nucleic acid expression vector and administering it so that it becomes intracellular, e.g., by use of a retroviral vector (see, for example, U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864-1868), etc. Alternatively, a nucleic acid can be introduced intracellularly and incorporated within host cell DNA for expression, by homologous recombination.

Prior to introduction, a composition comprising HB-X as disclosed herein can be sterilized, by any of the numerous available techniques of the art, such as with gamma radiation or electron beam sterilization.

In another embodiment of the invention, a composition comprising HB-X or variant thereof as disclosed herein, can be administered and/or formulated in conjunction (e.g., in combination) with any other therapeutic agent. For purpose of administration, HB-X as disclosed herein is preferably formulated as a pharmaceutical composition. Pharmaceutical compositions of the present invention comprise a compound of this invention and a pharmaceutically acceptable carrier, wherein the compound is present in the composition in an amount which is effective to treat the condition of interest. Appropriate concentrations and dosages can be readily determined by one skilled in the art.

Pharmaceutically acceptable carriers are familiar to those skilled in the art. For compositions formulated as liquid solutions, acceptable carriers include saline and sterile water, and may optionally include antioxidants, buffers, bacteriostats and other common additives. The compositions can also be formulated as pills, capsules, granules, or tablets which contain, in addition to a compound of this invention, diluents, dispersing and surface active agents, binders, and lubricants. One skilled in this art may further formulate the compounds of this invention in an appropriate manner, and in accordance with accepted practices, such as those disclosed in Remington's Pharmaceutical Sciences, Gennaro, Ed., Mack Publishing Co., Easton, Pa. 1990.

The compositions of the present invention can be in any form. These forms include, but are not limited to, solutions, suspensions, dispersions, ointments (including oral ointments), creams, pastes, gels, powders (including tooth powders), toothpastes, lozenges, salve, chewing gum, mouth sprays, pastilles, sachets, mouthwashes, aerosols, tablets, capsules, transdermal patches, that comprise one or more resolvins and/or protectins or their analogues of the invention.

Formulations of a composition comprising HB-X as disclosed herein can be prepared by a number or means known to persons skilled in the art. In some embodiments the formulations can be prepared for administration as an aerosol formulation, e.g., by combining (i) HB-X as disclosed herein in an amount sufficient to provide a plurality of therapeutically effective doses; (ii) the water addition in an amount effective to stabilize each of the formulations; (iii) the propellant in an amount sufficient to propel a plurality of doses from an aerosol canister; and (iv) any further optional components e.g. ethanol as a cosolvent; and dispersing the components. The components can be dispersed using a conventional mixer or homogenizer, by shaking, or by ultrasonic energy. Bulk formulation can be transferred to smaller individual aerosol vials by using valve to valve transfer methods, pressure filling or by using conventional cold-fill methods. It is not required that a stabilizer used in a suspension aerosol formulation be soluble in the propellant. Those that are not sufficiently soluble can be coated onto the drug particles in an appropriate amount and the coated particles can then be incorporated in a formulation as described above.

In certain embodiments, a composition comprising HB-X, which is a nucleic acid agent or polypeptide agent can be administered to a subject as a pharmaceutical composition with a pharmaceutically acceptable carrier. In certain embodiments, these pharmaceutical compositions optionally further comprise one or more additional therapeutic agents. In certain embodiments, the additional therapeutic agent or agents are autoimmune disease or drugs, such as immune suppressants and the like. Of course, such therapeutic agents are which are known to those of ordinary skill in the art can readily be substituted as this list should not be considered exhaustive or limiting.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions. Examples of pharmaceutically acceptable antioxidants include: water soluble antioxidants, such as ascorbic acid, cysteine hydrochloride, sodium bisulfate, sodium metabisulfate, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for intravenous, oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes.

The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs.

In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

In some instances, a composition comprising HB-X as disclosed herein can be in a formulation suitable for rectal or vaginal administration, for example as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore release the active compound. Suitable carriers and formulations for such administration are known in the art.

Dosage forms for the topical or transdermal administration of HB-X, e.g., for muscular administration include powders, sprays, ointments, pastes, creams, lotions, gels, solutions, patches and inhalants. HB-X as disclosed herein may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of HB-X to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

In certain embodiments, HB-X can be isolated and/or purified or substantially purified by one or more purification methods described herein or known by those skilled in the art. Generally, the purities are at least 90%, in particular 95% and often greater than 99%. In certain embodiments, the naturally occurring compound is excluded from the general description of the broader genus.

In some embodiments, the composition comprises at least one HB-X in combination with a pharmaceutically acceptable carrier. Some examples of materials which can serve as pharmaceutically acceptable carriers include, without limitation: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

In certain embodiments, a composition comprising HB-X as disclosed herein can contain one or more acidic functional groups and, thus, are capable of forming pharmaceutically acceptable salts with pharmaceutically acceptable bases. The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use of the compounds of the invention. The term "salts" refers to the relatively non-toxic, inorganic and organic acid addition salts of compounds of the present invention.

These salts can be prepared in situ during the final isolation and purification of the compounds or by separately reacting the purified compound in its free base form with a suitable organic or inorganic acid and isolating the salt thus formed. These may include cations based on the alkali and alkaline earth metals, such as sodium, lithium, potassium, calcium, magnesium and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M., et al., "Pharmaceutical Salts," J. Pharm. Sci., 1977; 66:1-19 which is incorporated herein by reference).

The term "pharmaceutically acceptable esters" refers to the relatively non-toxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. The term is further intended to include lower hydrocarbon groups capable of being solvated under physiological conditions, e.g., alkyl esters, methyl, ethyl and propyl esters.

As used herein, "pharmaceutically acceptable salts or prodrugs" are salts or prodrugs that are, within the scope of sound medical judgment, suitable for use in contact with the tissues of patients without undue toxicity, irritation, allergic response, and the like, commensurate with a reasonable benefit/risk ratio, and effective for their intended use. These compounds include the zwitterionic forms, where possible, of r compounds of the invention.

The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. These may include cations based on the alkali and alkaline earth metals, such as sodium, lithium, potassium, calcium, magnesium and the like, as well as non-toxic ammonium, quaternary ammonium, and amine cations including, but not limited to ammonium, tetramethylanunonium, tetraethyl ammonium, methyl amine, dimethyl amine, trimethylamine, triethylamine, ethylamine, and the like (see, e.g., Berge S. M., et al. (1977) J. Pharm. Sci. 66, 1, which is incorporated herein by reference).

The term "prodrug" refers to compounds or agents that are rapidly transformed in vivo to yield the active HB-X, e.g., a biologically active or functional active HB-X which encodes a functionally active therapeutic peptide or protein. In some embodiments, HB-X prodrugs can be activated by hydrolysis in blood, e.g., via cleavage of a precursor therapeutic protein into an active therapeutic protein, similar to how insulin is activated from its proprotein into an active insulin protein. A thorough discussion is provided in T. Higachi and V. Stella, "Pro-drugs as Novel Delivery Systems," Vol. 14 of the A.C.S. Symposium Series, and in Bioreversible Carriers in: Drug Design, ed. Edward B. Roche, American Pharmaceutical Association and Pergamon Press, 1987, both of which are hereby incorporated by reference. As used herein, a prodrug is a compound that, upon in vivo administration, is metabolized or otherwise converted to the biologically, pharmaceutically or therapeutically active form of the compound. The prodrug may be designed to alter the metabolic stability or the transport characteristics of HB-X, to mask side effects or toxicity, or to alter other characteristics or properties of HB-X. By virtue of knowledge of pharmacodynamic processes and drug metabolism or post-translational protein processing of HB-X in vivo, once a pharmaceutically active compound is identified, those of skill in the pharmaceutical art generally can design HB-X prodrugs which can be activated in vivo to increase levels of the therapeutic protein present in HB-X in the subject (see, e.g., Nogrady (1985) Medicinal Chemistry A Biochemical Approach, Oxford University Press, N.Y., pages 388-392). Conventional procedures for the selection and preparation of suitable prodrugs are described, for example, in "Design of Prodrugs," ed. H. Bundgaard, Elsevier, 1985. Suitable examples of prodrugs include methyl, ethyl and glycerol esters of the corresponding acid.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of ordinary skill in the art.

Vectors:

In another embodiment, this invention provides vector encoding HB-X fusion proteins for use in the methods, compositions and kits as disclosed herein. In some embodiments, the vector is an expression vector and enables the insertion of the nucleic acid sequence encoding an active agent of an investigators choice. In some embodiments, the present invention relates to a vector comprising a nucleic acid encoding at least one heparin binding peptide (HB) selected from KRKKKGKGLGKKRDPCLRKYK (SEQ ID NO:1), KRKKKGKGLGKKRDPRLRKYK (SEQ ID NO:2), or KRKKKGKGLGKKRDPKLRKYK (SEQ ID NO:3). In some embodiments, the vector comprises a multiple cloning site for insertion a nucleic acid sequence encoding an active agent of an investigators choice at the 3' or 5' or both of the HB sequence. In some embodiments, the vector comprises multiple HB peptides. In some embodiments, the vector also comprises at least one nucleic acid encoding a linker peptide (e.g., comprising at least GGG) at the 3' or 5' of the HB peptide sequence, before the multiple cloning site, depending on whether the nucleic acid sequence encoding X is inserted at the 3' or 5' or both of the HB peptide nucleic acid sequence. In some embodiments, the vector also comprises at least one nucleic acid sequence encoding at least one active agent (X).

In some embodiments, the vector comprises a nucleic acid sequence which encodes at least one HB-$X_n$ or $X_n$-HB$_n$ fusion protein, wherein HB is a heparin binding peptide selected from KRKKKGKGLGKKRDPCLRKYK (SEQ ID NO:1), KRKKKGKGLGKKRDPRLRKYK (SEQ ID NO:2), or KRKKKGKGLGKKRDPKLRKYK (SEQ ID NO:3); X is an active agent, and n is an integer of at least 1.

In some embodiments, the vector comprises a nucleic acid sequence which encodes at least one (HB-linker)$_n$-$X_n$ or at least one $X_n$-(HB-linker)$_n$ fusion protein, or at least one (HB-linker)$_n$-$X_m$-(HB-linker)o fusion protein, wherein HB is a heparin binding peptide selected from KRKKKGKGLGKKRDPCLRKYK (SEQ ID NO:1), KRKKKGKGLGKKRDPRLRKYK (SEQ ID NO:2), or KRKKKGKGLGKKRDPKLRKYK (SEQ ID NO:3); X is an active agent, wherein m is an integer of at least 1, and n+o is an integer of at least 1.

Kits

In another embodiment, this invention provides kits for the practice of the methods of this invention. The kits preferably include one or more containers containing a HB peptide and means to attach the HB peptide to an active agent (X). In some embodiments, a kit comprises (i) at least one HB peptide selected from the group consisting of: KRKKKGKGLGKKRDPCLRKYK (SEQ ID NO:1), KRKKKGKGLGKKRDPRLRKYK (SEQ ID NO:2), or KRKKKGKGLGKKRDPKLRKYK (SEQ ID NO:3); and a chemical linker to conjugate the HB peptide to a small molecule.

In some embodiments, a kit can comprise a vector comprising a nucleic acid encoding at least one heparin binding peptide (HB) selected from KRKKKGKGLGKKRDPCLRKYK (SEQ ID NO:1), KRKKKGKGLGKKRDPRLRKYK (SEQ ID NO:2), or KRKKKGKGLGKKRDPKLRKYK (SEQ ID NO:3) as disclosed herein, and suitable reagents (e.g., restriction enzymes and ligation enzymes etc.) for subcloning a nucleic acid sequence encoding at least one an active agent into the vector. In some embodiments, the vector in the kit also comprises nucleic acid sequences encoding linker peptides, which may be 3' or 5' (or both) of the nucleic acid sequence encoding the HB peptides, depending on where the active agent is to be cloned.

An another embodiment, a kit may comprise a HB-X conjugate, where X is a therapeutic protein or peptide for treatment of a disease or condition, e.g., a cartilage-related disease or disorder, a neurological disorder, a eye disorder or inflammation.

A kit may optionally contain additional therapeutics to be co-administered with the HB-X conjugate. The kit may comprise instructions for administration of a HB-X conjugate to a subject with a cartilage-related disease or disorder, a neurological disorder, a eye disorder or inflammation.

The kits may also optionally include appropriate systems (e.g. opaque containers) or stabilizers (e.g. antioxidants) to prevent degradation of the HB-X conjugate by light or other adverse conditions.

In another aspect of the invention provides kits including one or more containers containing a HB-X conjugate as disclosed herein and a pharmaceutically acceptable excipient. The kit may optionally contain additional therapeutics to be co-administered with the HB-X conjugate. The kit may comprise instructions for administration of a subject with a cartilage-related disease or disorder, a neurological disorder, a eye disorder or inflammation.

The kits may optionally include instructional materials containing directions (i.e., protocols) providing for the use of HB-X conjugates for the treatment of a disease in a mammal, e.g., for the treatment of a cartilage-related disease or disorder, a neurological disorder, a eye disorder or inflammation.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

In some embodiments, the present invention may be defined in any of the following numbered paragraphs:

1. A composition comprising at least one HBn-Xn, wherein HB is a heparin binding peptide selected from KRKKKGKGLGKKRDPCLRKYK (SEQ ID NO:1), KRKKKGKGLGKKRDPRLRKYK (SEQ ID NO:2), or KRKKKGKGLGKKRDPKLRKYK (SEQ ID NO:3); X is an active agent, and n is an integer of at least 1.
2. The composition of paragraph 1, further comprising a linker, wherein the composition is represented by (HB-linker)n-Xn.
3. The composition of paragraph 2, wherein the linker is a peptide comprising the sequence GGG.
4. The composition of paragraph 3, having the HB-linker portion of the composition is selected from KRKKKGKGLGKKRDPRL-RKYKGGGKRKKKGKGLGKKRDPRLRKYK (SEQ ID NO:4), or KRKKKGKGLGKKRDPRL-RKYKGGGKRKKKGKGLGKKRDPRL-RKYKGGGKRKKKGKGLG KKRDPRLRKYK (SEQ ID NO:5).
5. The composition of any one of the preceding paragraphs, wherein X is a protein selected from Neurotrophic factors; Neurothrophins; nerve growth factor (NGF); brain-derived neurotrophic factor (BDNF); neurotrophin-3 (NT-3); neurotrophin-4 (NT-4); Ciliary neurotrophic factor (CNTF); mesencephalic astrocyte-derived neurotrophic factor (MANF); conserved dopamine neurotrophic factor (CDNF); Glial cell-line derived neurotrophic factor family ligands; glial cell line-derived neurotrophic factor (GDNF); neurturin (NRTN); artemin (ARTN); or persephin (PSPN); Neuropoietic cytokines; interleukin-6; interleukin-11; interleukin 27; leukaemia inhibitory factor; ciliary neurotrophic factor; cardiotrophin 1; neuropoietin; cardiotrophin-like cytokine; Fibroblast Growth Factor 2; Anti-inflammatory cytokines; interleukin-4; interleukin-10; Neuroprotection agents; Neuregulin-1; Vascular endothelial growth factor (VEGF); Cerebrolysin® (FPF 1070), Etanercept (Enbrel®, soluble recombinant TNF receptor 2 fused to the Fc component of human immunoglobulin G1); Growth differentiation factor 11 (GDF11); Stromal cell-derived factor 1 (SDF-1); Myostatin (growth differentiation factor 8 (GDF8)); Parathyroid hormone (PTH); Parathyroid hormone related peptide (PTHrP); Interleukin 1 receptor antagonist (IL-1RA); Fibroblast growth factor 18 (FGF-18); High-mobility group protein 2 (HMG-2, also known as High mobility group box 2 (HMGB2)); Glucocorticoid receptor; a therapeutic antibody or portion thereof, such as Remicade® (infliximab, anti-TNF-α, Janssen Biotech, Horsham, Pa.), Humira® (adalimumab, anti TNF, Abbot Labs., N. Chicago, Ill.), or an anti-nerve growth factor antibody; Fibroblast growth factor 9 (FGF 9); Hepatocyte growth factor; TGFβ-superfamily proteins such as TGFβ, TGFβ3, BMP2, or BMP7; or other therapeutic proteins; or functional portions, variants, analogs, or derivatives of any of the foregoing; or small molecule active agents.
6. The composition of any one of the preceding paragraphs, wherein HBn-Xn or (HB-linker)n-Xn is a fusion protein.
7. The composition of paragraph 1-6, wherein X or linker is fused to the N-terminus of HB.
8. The composition of paragraph 1-6, wherein X or linker is fused to the C-terminus of HB.
9. The composition of paragraph 1-6, wherein n=2, and X is fused to both the N-terminus and the C terminus of HB, optionally including at least one linker peptide.
10. A method of treating cartilage-related clinical conditions (e.g., damage or disease) comprising administering to a subject an effective amount of a recombinant fusion protein comprising HB-Xn or (HB-linker)n-Xn, wherein X is a therapeutic protein selected from Parathyroid hormone (PTH); Parathyroid hormone related peptide (PTHrP); Interleukin 1 receptor antagonist (IL-1RA); Fibroblast growth factor 18 (FGF-18), an anti-nerve growth factor antibody; Fibroblast growth factor 9 (FGF 9); Hepatocyte growth factor; TGFβ-superfamily proteins such as TGFβ, TGFβ3, BMP2, or BMP7; or portions, analogs, derivatives or functional fragments thereof
11. A method of treating a cartilage-related condition (e.g., damage or disease) comprising administering to a subject an effective amount of a recombinant fusion protein comprising HB-Xn or (HB-linker)n-Xn, where X is a Glucocorticoid receptor; and further administering concurrently or separately a Corticosteroid.
12. The method of paragraph 10 or 11, wherein the cartilage-related condition is a articular cartilage defect including rupture or detachment, a meniscal defect including a partial or complete tear, Osteoarthritis, Traumatic cartilage rupture or detachment, Ankylosing spondylitis, Capsulitis, Psoriatic arthritis, Rheumatoid arthritis, Systemic lupus erythematosus, Juvenile idiopathic arthritis, or X-linked hypophosphatemic rickets.
13. A method of treating a neurological condition (e.g., a disorder or disease) comprising administering to a subject an effective amount of a recombinant fusion protein comprising HB-Xn or (HB-linker)n-Xn, wherein X is a therapeutic protein selected from nerve growth factor (NGF), brain-derived neurotrophic factor (BDNF), neurotrophin-3 (NT 3), neurotrophin 4 (NT-4), Ciliary neurotrophic factor (CNTF), mesencephalic astrocyte-derived neurotrophic factor (MANF), conserved dopamine neurotrophic factor (CDNF), glial cell line-derived neurotrophic factor (GDNF), neurturin (NRTN), artemin (ARTN), persephin (PSPN), interleukin 6, interleukin 11, interleukin 27, leukaemia inhibitory factor, ciliary neurotrophic factor, cardiotrophin 1, neuropoietin, cardiotrophin-like cytokine, FPF 1070, Fibroblast Growth Factor 2, Neuregulin 1, Vascular endothelial growth factor (VEGF), or a functional portion, analog, or derivative thereof
14. The method of paragraph 13, wherein the neurological condition is Alzheimer's disease, Parkinson's disease, Amyotrophic lateral sclerosis, Multiple sclerosis, Brain injury, Spinal cord injury, Peripheral nerve degeneration, Stroke, Huntington's disease, Pick's disease, Diabetic neuropathy, Frontotemporal dementia, Dementia with Lewy bodies, Corticobasal degeneration, Progressive supranuclear palsy, Prion disorders, Progressive supranuclear palsy, Multiple system atrophy, Hereditary spastic paraparesis, Spinocerebellar atrophies, Friedreich's ataxia, Amyloidoses, or Charcot Marie Tooth syndrome.
15. A method of treating an eye disease such as Corneal ulcer/Corneal abrasion, Thygeson's superficial punctate keratopathy, Corneal neovascularization, Fuchs' dystrophy, Keratoconjunctivitis sicca, Chorioretinal inflammation, Chorioretinal scars, Choroidal degeneration, Hereditary choroidal dystrophy, Retinal detachment, Retinoschisis, Hypertensive retinopathy, Retinopathy of prematurity, Age-related macular degeneration, Retinal degeneration, Macular degeneration, Epiretinal membrane, Peripheral retinal degeneration, Hereditary retinal dystrophy, Retinitis pigmentosa, Xerophthalmia, or Retinal haemorrhage, comprising administering the composition of any of paragraphs 1-9.

16. A method of treating inflammation comprising administering to a subject an effective amount of a recombinant fusion protein comprising HB Xn, or (HB-linker)n-Xn, where X is a therapeutic protein or a portion thereof, selected from TNF receptor 2, interleukin 4, or interleukin-10.

17. The composition of any one of paragraphs 1 to 4, wherein X is a small molecule.

18. The composition of paragraph 6 or 32, wherein the fusion protein is selected from the following:

19. KRKKKGKGLGKKRDPRLRKYKGGGKRKKKGKGLGKKRDPRLRKYKGPETLCGAELV DALQFVCGDRGFYFNKPTGYGSSSRRAPQTGIVDECCFRSCDLRRLEMYC APLKPAKSARSV RAQRHTDMPKTQKEVHLKNASRGSA (SEQ ID NO:10); KRKKKGKGLGKKRDPRLRKYKGGGKRKKKGKGLGKKRDPRLRKYKGGGKRKKKGKGL GKKRDPRLRKYKGPETLCGAELVDALQFVCGDRGFYFNKPTGYGSSSRRAPQTGIVDECCF RSCDLRRLEMYCAPLKPAKSARSVRAQRHTDMPKTQKEVHLK NASRGSA (SEQ ID NO:11); MKRKKKGKGLGKKRDPRLRKYKGPETLCGAELVDALQFVCGDRGFYFNKPTGYGSSSRR APQTGIVDECCFRSCDLRRLEMYCAPLKPAKSARSVRAQRHTDMPKTQKEVHLKNASRGSA (SEQ ID NO:12); MKRKKKGKGLGKKRDPKLRKYKGPETLCGAELVDALQFVCGDRGFYFNKPTGYGSSSRR APQTGIVDECCFRSCDLRRLEMYCAPLKPAKSARSVRAQRHTDMPKTQ KEVHLKNASRGSA (SEQ ID NO:13); MKRKKKGKGLGKKRDPRLRKYKGPETLCGAELVDALQFVCGDRGFYFNKPTGYGSSSRR APQTGIVDECCFRSCDLRRLEMYCAPLKPAKSA (SEQ ID NO:14); MKRKKKGKGLGKKRDPKLRKYKGPETLCGAELVDALQFVCGDRGFYFNKPTGYGSSSRRA PQTGIVDECCFRSCDLRRLEMYCAPLKPAKSA (SEQ ID NO:15); KRKKKGKGLGKKRDPRLRKYKGPETLCGAELVDALQFVCGDRGFYFNKPTGYGSSSRRAP QTGIVDECCFRSCDLRRLEMYCAPLKPAKSARSVRAQRHTDMPKTQKEVHLKNASRGSA (SEQ ID NO:16); KRKKKGKGLGKKRDPKLRKYKGPETLCGAELVDALQFVCGDRGFYFNKPTGYGSSSRRAP QTGIVDECCFRSCDLRRLEMYCAPLKPAKSARSVRAQRHTDMPKTQKEVHLKNASRGSA (SEQ ID NO:17); KRKKKGKGLGKKRDPRLRKYKGPETLCGAELVDALQFVCGDRGFYFNKPTGYGSSSRRAP QTGIVDECCFRSCDLRRLEMYCAPLKPAKSA (SEQ ID NO:18); or KRKKKGKGLGKKRDPKLRKYKGPETLCGAELVDALQFVCGDRGFYFNKPTGYGSSSRRAP QTGIVDECCFRSCDLRRLEMYCAPLKPAKSA (SEQ ID NO:19).

20. The composition of paragraph 1-6, wherein HBn=2, and HB is fused to both the N-terminus and the C terminus of X, wherein the fusion of HB to the N or C terminus optionally including at least one linker peptide.

21. The composition of any of paragraphs 1-5, wherein the HBn-Xn comprises (HB-linker)n-Xm-(HB-linker)o, wherein m is an integer of at least 1, and n+o is an integer of at least 1.

22. The composition of paragraph 20, wherein the HBn-Xn comprises two or more different HB peptides selected from KRKKKGKGLGKKRDPCLRKYK (SEQ ID NO:1), KRKKKGKGLGKKRDPRLRKYK (SEQ ID NO:2), or KRKKKGKGLGKKRDPKLRKYK (SEQ ID NO:3).

23. The composition of any of paragraphs 1-9, wherein the composition comprises at least 2 HBn-Xn conjugates.

24. The composition of any of paragraphs 6, 21 or 22, wherein X is selected from any one or a combination of proteins from the group consisting of: SEQ ID NO: 6-9, SEQ ID NO: 30-41, SEQ ID NO: 63 and SEQ ID NO: 73-76, or functional fragments thereof 25. The composition of any of paragraphs 1-9 and 17-23 for delivering an active agent X to a cell or tissue expressing proteoglycans.

26. The composition of paragraph 24, wherein the tissue is cartilage tissue, neuronal tissue, skin or subcutaneous tissue.

27. The composition of any of paragraphs 1-9 and 17-25, wherein the composition comprises a hydrogel.

28. The composition of paragraph 26, wherein the hydrogel is a self-assembly peptide hydrogel.

29. The composition of paragraph 27, wherein the self-assembly peptide hydrogel comprises at least one or a combination of peptides selected from: RADARADARADARADA (SEQ ID NO: 77), KLDLKLDLKLDL (SEQ ID NO: 78) or AcN-KLDLKLDLKLDL-CNH2 (SEQ ID NO: 79).

30. The method of any of paragraphs 10-16, wherein the HB-Xn or (HB-linker)n-Xn is present on or within a hydrogel.

31. The method of paragraph 29, wherein the hydrogel is a self-assembly peptide hydrogel.

32. The method of paragraph 30, wherein the self-assembly peptide hydrogel comprises at least one or a combination of peptides selected from: RADARADARADARADA (SEQ ID NO: 77), KLDLKLDLKLDL (SEQ ID NO: 78) or AcN-KLDLKLDLKLDL-CNH2 (SEQ ID NO: 79).

33. The method of any of paragraphs 10-16, wherein the HB-Xn or (HB-linker)n-Xn is present on or within a biological implant.

34. The method of paragraph 32, wherein the biological implant is an osteochondral or meniscal allograft.

35. A method of treating cartilage-related clinical conditions (e.g., damage or disease) comprising administering to a subject an effective amount of a recombinant fusion protein comprising HB-Xn or (HB-linker)n-Xn, wherein X is a therapeutic protein selected from angiopoietin-like 3 (ANGPTL3), somatostatin (SST); or fragments, portions, analogs, derivatives or functional fragments thereof 36. The method of paragraph 34, wherein an analogue of SST is selected from octreotide, pasireotide or lamreotide.

37. A vector comprising a nucleic acid encoding at least one heparin binding peptide (HB) selected from KRKKKGKGLGKKRDPCLRKYK (SEQ ID NO:1), KRKKKGKGLGKKRDPRLRKYK (SEQ ID NO:2), or KRKKKGKGLGKKRDPKLRKYK (SEQ ID NO:3).

38. The vector of paragraph 36, further comprising at least one nucleic acid sequence encoding at least one active agent (X).

39. The vector of paragraph 36, further comprising at least one nucleic acid sequence encoding at least one linker.

40. The vector of paragraph 37, wherein the nucleic acid sequence encodes at least one HB-Xn or Xn-HBn fusion protein, wherein HB is a heparin binding peptide selected from KRKKKGKGLGKKRDPCLRKYK (SEQ ID NO:1), KRKKKGKGLGKKRDPRLRKYK (SEQ ID NO:2), or KRKKKGKGLGKKRDPKLRKYK (SEQ ID NO:3); X is an active agent, and n is an integer of at least 1.

41. The vector of paragraph 38, wherein the nucleic acid sequence encodes at least one (HB-linker)n-Xn or at least one Xn-(HB-linker)n fusion protein, or at least one (HB-linker)n-Xm-(HB-linker)o fusion protein, wherein HB is a heparin binding peptide selected from KRKKKGKGLGKKRDPCLRKYK (SEQ ID NO:1), KRKKKGKGLGKKRDPRLRKYK (SEQ ID NO:2), or KRKKKGKGLGKKRDPKLRKYK (SEQ ID NO:3); X is an active agent, wherein m is an integer of at least 1, and n+o is an integer of at least 1.

42. The vector of paragraph 36 or 38, wherein the linker comprises GGG.

43. The vector of any of paragraphs 36 to 41, wherein the nucleic acid sequence encoding the X or linker is 5' to the nucleic acid encoding HB.

44. The vector of any of paragraphs 36 to 41, wherein the nucleic acid sequence encoding the X or linker is 3' to the nucleic acid encoding HB.

45. The vector of any of paragraphs 36 to 41, wherein the nucleic acid sequence encoding the HB peptide is 5' and 3' of the nucleic acid encoding X or the linker.

46. The vector of any of paragraphs 36 to 44, wherein the vector is an expression vector.

47. A kit comprising: (i) at least one HB peptide selected from the group consisting of: KRKKKGKGLGKKRDPCLRKYK (SEQ ID NO:1), KRKKKGKGLGKKRDPRLRKYK (SEQ ID NO:2), or KRKKKGKGLGKKRDPKLRKYK (SEQ ID NO:3); and (ii) a chemical linker to conjugate the HB peptide to a small molecule.

48. A kit comprising a vector of paragraph 36 or 38 and regents for inserting a nucleic acid sequence encoding an active agent (X) into said vector.

49. A cell line comprising the vector of any of paragraphs 36 to 45.

Embodiments will now be described further by non-limiting examples.

EXAMPLES

Material and Methods

Cartilage Binding Assay:

Cartilage explants were harvested from stifle joints of 1-2-week-old newborn bovine calves (Research 87 Inc., Boylston Mass.). Articular cartilage was sliced and punched into 1-mm-thick by 3-mm-diameter disks and incubated at 37 C in low-glucose DMEM.

Cartilage disks were incubated with medium alone, PTH, or eHB-PTH. After 24 hours, all cartilage disks were washed ×3 in fresh medium with no added peptide. Cartilage was then returned to incubation and harvested after two days or four days in the absence of peptide.

Protein Extraction from Cartilage Discs and Analysis:

Cartilage disks were individually pulverized while cooled with liquid nitrogen. The powder was resuspended in lysis buffer containing 0.1% Triton X-100, 1 mM PMSF and protease inhibitor cocktail (Sigma) and rotated overnight at 4° C. The resulting extracts were clarified by centrifugation and protein concentration assayed with 660 nm Protein Assay (Pierce).

For Western analysis, portions of extracts containing equal amounts of protein (3 ug total protein/lane) were boiled under reducing conditions and electrophoresed on 4-12% Bis-Tris gels. A rabbit polyclonal anti-PTH antibody was from Abcam (ab40630) for western blotting analysis of the presence of PTH in the cartilage explants. Membranes were probed for PTH with a 1:1000 dilution of antibody ab40630, followed by a secondary goat anti-rabbit antibody at a dilution of 1:5000.

For Assessment of HB-IGF1 Retension in the Spinal Cord:

Retired male breeder rats were obtained from Charles River. A rat was euthanized and tissues were harvested. Spinal cord tissue was taken after dissection and divided into portions of similar. Each portion was weighed and then incubated in 1 mL serum-free DMEM at 37 C in a 24-well plate. Medium was then replaced with serum-free DMEM containing either no additions, 1 ug/ml of IGF-1, or 1 ug/ml HB-IGF-1. IGF-1 was human recombinant IGF-1 (Increlex, Tercica). IGF-1 was fused to HB(C17R) (SEQ ID NO: 21). HB-IGF-1 was expressed as human recombinant HB-C17R-IGF-1, and extracted from inclusion bodies after expression in E. coli. After incubation of the spinal cord with the HB-IGF1 for one day, medium was replaced with serum-free DMEM containing no additions. One set of tissue was collected as the "Day 0" samples and stored frozen at −20 C. Tissue samples were then taken after 24 hours of wash-out ("Day 1").

Protein Extraction from the Spinal Cord and Analysis:

Proteins were extracted from the frozen spinal cord tissues by homogenizing in 1 ml lysis buffer/100 mg tissue. The lysis buffer contained 0.1% Trition X-100 with 1 mM PMSF and protease inhibitor cocktail (Sigma). Total protein concentrations were measured and portions of extracts containing equivalent amounts of total protein were boiled in reducing sample buffer and loaded on 4-12% Bis-Tris gels for Western analysis.

Determination of Expression of Fusion Proteins Comprising C17K and C17R HB Peptides:

Superior Expression of Soluble HB-IGF-1 was detected with enhanced HB peptides (e.g., C17R and C17K) sequences as compared to wildtype (SEQ ID NO: 20) and C17S sequences (SEQ ID NO; 41). The protein expression from following plasmids were assessed: (i) Plasmid 04 HB(C17K)-IGF-1 in pET24a(+), (ii) Plasmid 05 HB(C17R)-IGF-1 in pET24a(+), (iii) plasmid 06 HB(C17S)-IGF-1 in pET24a(+), and (iv). Plasmid 07: HB-IGF-1 in pET24a(+). HB-IGF-1 and mutants (listed above) were transformed into T7 Express E. coli cells and grown in Luria-Bertani (LB) medium in 1 L batches. Protein expression was induced with 1 mM isopropyl β-D-thiogalactoside for 4 h, and cells were then harvested by centrifugation. Proteins were extracted with 10 ml BugBuster Master Mix native extraction reagent (Novagen). 10 ul of each sample was run on a 4-12% Bis-Tris gel in reducing conditions. Expression levels were compared by western blot using IGF-1 antibody ab9572 (AbCam).

Determination of Yield of Production of Fusion Proteins Comprising C17K and C17R HB Peptides:

A superior yield on purification of soluble HB-IGF-1 fusion proteins comprising enhanced HB (C17R) peptide was detected. The following yield of fusion protein from the following plasmids were assessed: (i) Plasmid 05 HB(C17R)-IGF-1 in pET24a(+) or (ii) Plasmid 07: HB-IGF-1 in pET24a (+).

HB-IGF-1 and HB(C17R)-IGF-1 (listed above) were transformed into T7 Express E. coli cells and grown in Luria-Bertani (LB) medium in 1 L batches. Protein expression was induced with 1 mM isopropyl β-D-thiogalactoside for 4 h, and cells were then harvested by centrifugation. Proteins were extracted with BugBuster Master Mix native extraction reagent (Novagen). Purification was performed by loading samples onto a HiLoad 16/60 Superdex 200 size exclusion chromatography column. 2 ml was eluted in each fraction. 10 ul of each fraction was run on a 4-12% Bis-Tris gel in reducing conditions. IGF-1 in each fraction was assayed for by western blot using IGF-1 antibody ab9572 (AbCam). Protein was detected in fractions 3-12 (fractions shown) for the C17R variant (eHB) and in fractions 4-10 for the wild type variant.

To demonstrate that enhanced HB (C17R) allows superior yield of HB-IGF-1 fusion protein from inclusion bodies, plasmids encoding HB-IGF-1 and HB(C17R)-IGF-1 (e.g., Plasmid 05 HB(C17R)-IGF-1 in pET24a(+) or (ii) Plasmid 07: HB-IGF-1 in pET24a(+) as listed above) were transformed into T7 Express *E. coli* cells and grown in Luria-Bertani (LB) medium in 1 L batches. For induced samples, protein expression was induced with 1 mM isopropyl β-D-thiogalactoside for 4 h. Non-induced samples were allowed to grow for 4 h without 1 mM isopropyl β-D-thiogalactoside. Cells were then harvested by centrifugation. Cells were lysed in 8 ml lysis buffer containing 6 M guanidine hydrochloride, 20 mM sodium phosphate, 500 mM NaCl, pH 7.8. Cell lysates were dialyzed into a buffer containing 50 mM Tris, 100 mM NaCl. 5 ul of each sample was run on a 4-12% Bis-Tris gel in reducing conditions. Samples were analyzed for IGF-1 by western blot using IGF-1 antibody ab9572 (AbCam) and by Coomassie stain.

Example 1

HB-IGF-1 Fusion Protein

A HB-IGF-1 construct was made to express a heparin-binding domain fused to the amino-terminus of a mature IGF-1 protein. The HB-IGF-1 fusion protein was produced by recombinant expression in *E. coli*, refolded, and purified by reverse-phase chromatography. Human recombinant IGF-1 is available commercially, for example INCRELEX® (mecasemin [rDNA origin], Ipsen Biopharmaceuticals, Inc., Basking Ridge, N.J.).

Example 2

In Vivo Binding and Pharmacokinetics

Experiments were performed with male Lewis rats (251-275 g, Charles River, Wilmington, Mass.). All animal procedures were approved by the Harvard Medical Area Standing Committee on Animals.

Rats received a single intraarticular injection containing 100 μg of HB-IGF-1, 100 μg IGF-1, or phosphate buffered saline (PBS) in the right patellofemoral joint. Articular cartilage, medial meniscus and patellar tendon samples were harvested at 2, 4, 6, and 8 days after injection. Samples were weighed, pulverized while in liquid nitrogen and extracted with 10 μl of lysis buffer (100 mM NaCl, 50 mM Tris, 0.5% Triton X-100, 5 mM EDTA, 1 mM PMSF, and protease inhibitor cocktail [Roche]) per milligram of tissue. Portions of extracts with equal protein mass were analyzed by Western blotting. Serum IGF-1 levels were measured by ELISA (R&D Systems #DY291) reactive with human but not rodent IGF-1.

Example 3

Cartilage Biosynthesis Assay

Rats were randomly assigned to receive a single intraarticular injection containing 100 μg of HB-IGF-1, 100 μg IGF-1, or PBS in the right patellofemoral joint. Animals were sacrificed 2 or 4 days after injection. Following sacrifice, the meniscus from the right knee joint was harvested and incubated at 37° C. in Dulbecco's Modified Eagle Medium (DMEM) containing 5 μCi/ml $^{35}$S-sulfate for 18 hr. Following incubation, samples were washed four times for 15 min in PBS with sulfate to remove unincorporated radiolabel. Samples were digested overnight with 1 mg/ml Proteinase K at 60° C. and radiolabel incorporation was measured in a liquid scintillation counter.

Example 4

Rat Model of Joint Damage

For surgical procedures, rats were randomly assigned to one of three groups: 50 μl intraarticular injections containing 100 μg of HB-IGF-1, 100 μg IGF-1, or PBS in the right knee joint. Initial injections were administered 1 day prior to medial meniscal tear (MMT). The MMT model was used as previously described. Gerwin et al., 18 Osteoarthr. Cartil. S24 (2010). Briefly, a skin incision was made across the medial aspect of the knee. The medial collateral ligament was exposed by blunt dissection and transected. The medial meniscus was reflected medially and cut to simulate a full tear. Subsequent intraarticular injections were administered 7 and 14 days post MMT. Animals were sacrificed 21 days after surgery.

Histological staging and sectioning was performed. Knee joints were harvested and fixed in 4% paraformaldehyde. Joints were then transferred to 5% formic acid decalcifying solution (ImmunoCal, Decal Chemical Corp, Tallman, N.Y.). Joints were cut in half to form anterior and posterior sections, and embedded in paraffin. 8 μm sections taken approximately 200 μm apart were stained with Toluidine Blue.

The medial tibial plateau was analyzed and imaged microscopically. The central most sections exhibiting the maximum injury extent were selected for blinded scoring. Injuries were scored using a modified Mankin scoring system. Injuries were measured using three different metrics: cartilage matrix loss width, total cartilage degeneration width, and significant degeneration width.

Cartilage matrix loss width measured only the extent of 100% matrix loss while areas of PG or chondrocyte degeneration are ignored. Measurements were taken at the surface (0% depth) and at the tidemark (100%) depth. Total cartilage degeneration width measured the total width of the area of articular cartilage affected by any type of degenerative change. Significant cartilage degeneration width measured the extent of injury that affects more than 50% of the thickness of cartilage. Significant cartilage degeneration width included any form of collagen matrix, PG, or chondrocyte degeneration. All results are expressed as mean±SEM.

Example 5

The inventors demonstrated that modification of amino acid residue 17 in SEQ ID NO: 20 (corresponding to amino acid residue 16 in SEQ ID NO: 1) could increase the yield and retention of the HB-fusion protein in tissue. Using the 17-mer HB peptide of SEQ ID NO: 20, the inventors demonstrate that there is unexpected superior retention of soluble HB-IGF-1 in cartilage explants incubated with fusion proteins comprising enhanced HB (eHB) peptides: C17K (SEQ ID NO:22) and C17R (SEQ ID NO: 21), as compared to HB-IGF1 fusion proteins comprising C17S (MKRKKKGKGLGKKRDPSL-RKYK; SEQ ID NO: 41) or wild-type HB (SEQ ID NO: 20).

Figure 5:
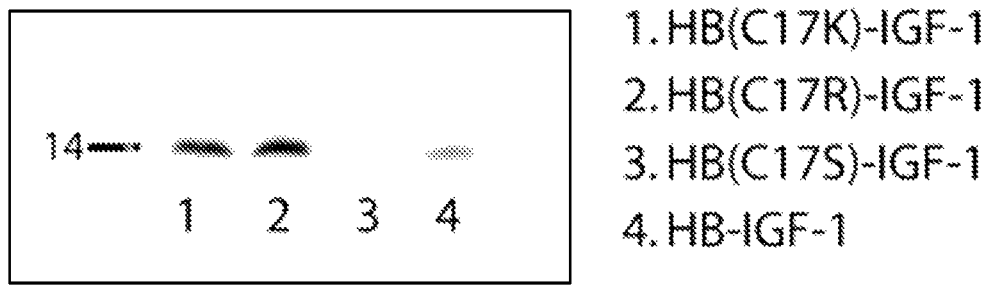
FIG. 5 shows superior expression of soluble HB-IGF-1 comprising enhanced HB (eHB) peptides: C17K (SEQ ID NO:22) and C17R (SEQ ID NO: 21).

Furthermore, there is unexpected superior expression of soluble HB-IGF-1 in cartilage explants incubated with fusion proteins comprising enhanced HB (eHB) peptides: C17K (SEQ ID NO:22) and C17R (SEQ ID NO: 21), as compared to HB-IGF1 fusion proteins comprising C17S (MKRKKKGKGLGKKRDPSLRKYK; SEQ ID NO: 41) or wild-type HB (SEQ ID NO: 20) (FIG. 5).

Figure 6:
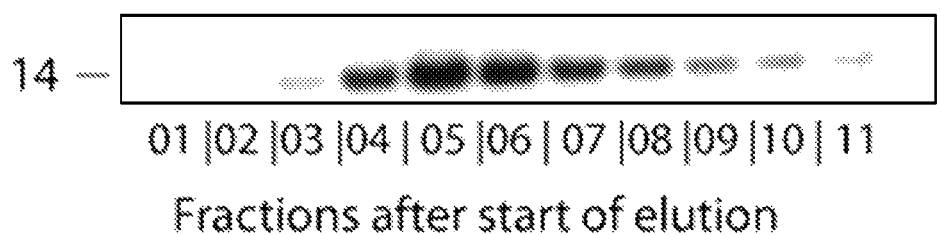
FIG. 6 shows superior yield on purification of soluble HB-IGF-1 with a HB-IGF-1 fusion protein comprising the C17R (SEQ ID NO: 21) HB variants.
Figure 6:
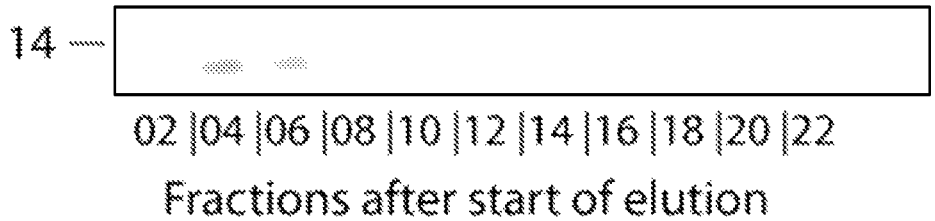

Furthermore, suprizingly, the inventors detected a significantly higher yield upon purification of soluble HB-IGF-1 with cartilage explants incubated with HB-IGF-1 fusion proteins comprising C17R (SEQ ID NO: 21) as compared to cartilage explants incubated with a HB-IGF fusion protein comprising wild-type HB (SEQ ID NO: 20) (FIG. 6).

Figure 7:
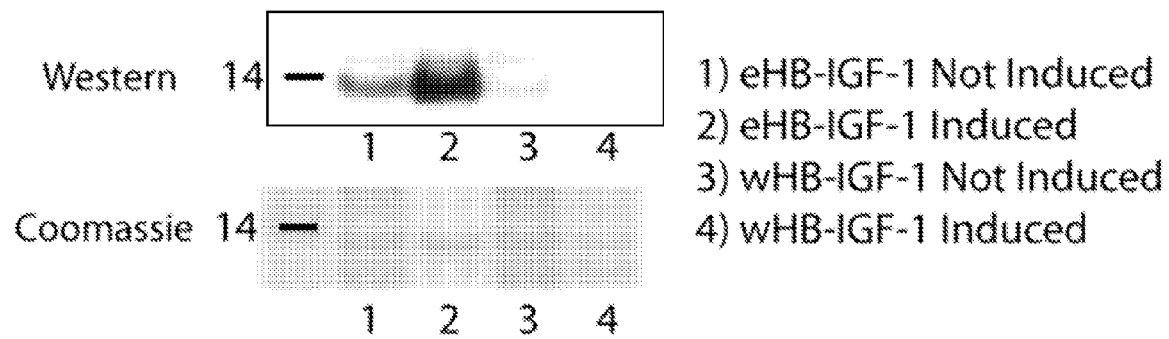

Next, the inventors also demonstrate that a higher yield of purification of soluble HB-IGF can also be obtained from the inclusion bodies (induced and non-induced) obtained from cartilage explants incubated with HB-IGF-1 fusion protein comprising C17R (SEQ ID NO: 21) as compared to cartilage explants incubated with HB-IGF-1 comprising wild-type HB (SEQ ID NO: 20) (FIG. 7).

Accordingly, the inventors demonstrate that modification of negatively charged amino acids in SEQ ID NO: 1 or SEQ ID NO: 20, e.g., a change of the cysteine residue at amino acid 17 in SEQ ID NO: 20, (or a change of the cysteine amino acid residue 16 in SEQ ID NO: 1) to a positively charged reside (e.g., arginine or lysine) can surprisingly result in a significant increase the amount of the HB-fusion protein retained in the tissue, as well as significantly increase the yield of the HB-fusion protein obtained from the tissue from both whole tissue extracts (FIG. 6) and inclusion bodies from the tissue extract (FIG. 7).

Example 6

In Examples 1-4, the inventors demonstrate that that heparin-binding (HB) fusions with IGF-1 allow for extended retention of the fusion protein within cartilage tissue through interaction with highly abundant chondroitin sulfated proteoglycans. However, other tissues also have abundant negatively charged proteoglycans in their extracellular matrix. Accordingly, the inventors assessed whether a HB-IGF-1 fusion protein would extend retention of the protein in neural tissue harvested from the spinal cord.

Figure 8:
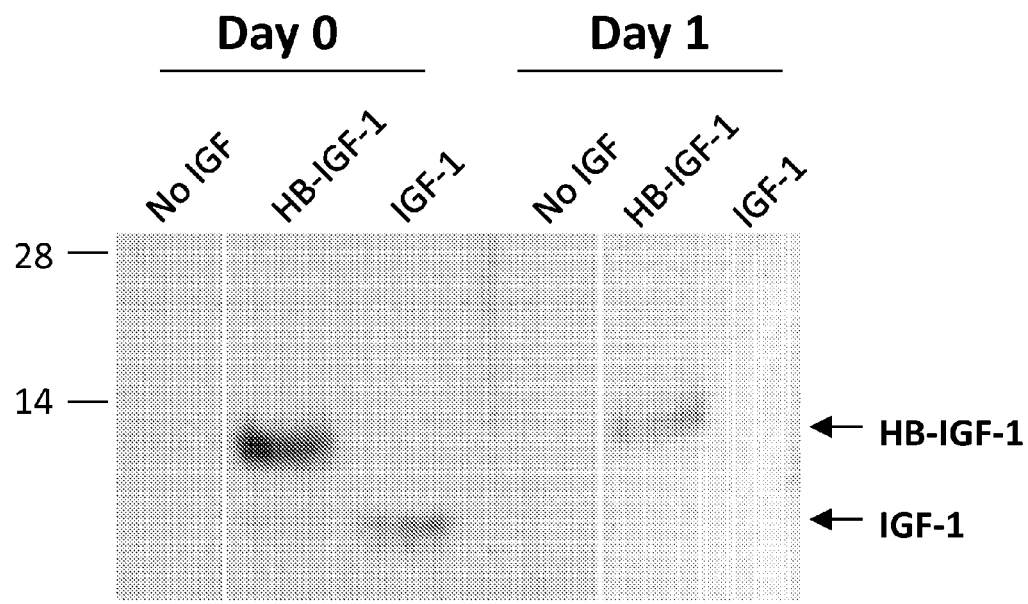

After incubation of the spinal cord explants in the presence of IGF-1 or HB-IGF-1 for one day, both proteins were detected in the tissue extracts by Western analysis for IGF-1 (FIG. 8). After one day of washout, no detectable non-fused IGF-1 was detected to be remaining in the tissue. In contrast, the HB-IGF-1 protein remains detectable in the spinal cord tissue extracts (FIG. 8).

Accordingly, the inventors have demonstrated herein that that HB-IGF-1 is retained in spinal cord tissue ex vivo for at least 24 hours, whereas unmodified (non-fused) IGF-1 is not. Accordingly, HB fused to a protein allows extended retention of the proteins in tissues other than cartilage, including neural tissue and other tissues with abundant chondroitin sulfated proteoglycans on cell surfaces of the tissues.

Example 7

In Examples 1-4, the inventors demonstrate that fusion of the HB domain with IGF-1 allows for targeted and sustained retention of the IGF-1 fusion protein in cartilage. However, as discussed herein, fusion of HB domain are not limited to the IGF-1 protein. Accordingly, HB can be fused to any active agent as a strategy for targeted delivery of multiple therapeutic proteins.

A peptide of the parathyroid hormone (PTH), e.g., amino acids 1-34 (PTH(1-34) is a peptide approved for clinical use in osteoporosis that has potential benefits in cartilage repair. In a rat osteoarthritis model, it has been shown to reduce the extent of osteoarthritis development (Chang et al., 2009).

As demonstrated herein, the inventors assessed the retention of PTH in the cartilage using bovine tissue culture explant using a PTH-HB fusion protein.

The following PTH peptides were generated by synthesis (Peptide 2.0, Chantilly Va.):
1. PTH(1-34)-biotin: SVSEIQLMHNLGKHLNS-MERVEWLRKKLQDVHNFK(-biotinyl)-$NH_2$ (SEQ ID NO: 80)
2. PTH(1-34)-linker-HB-biotin: SVSEIQLM-HNLGKHLNSMERVEWLRKKLQDVHN-FGGGKRKKKGKGLGKKRDPRLRKYKK(biotinyl)-$NH_2$ (SEQ ID NO: 81). Biotin was added to the PTH(1-34) and PTH(1-34)-linker-HB peptide for identification and tracking purposes. Similarly, a PTH(1-34)-linker-HB construct without the biotin can be used for therapeutic purposes. Additionally, the absence of a linker can also be used, as disclosed herein. A rabbit polyclonal anti-PTH antibody was from Abcam (ab40630) for western blotting analysis of the presence of PTH in the cartilage explants.

Figure 9A:
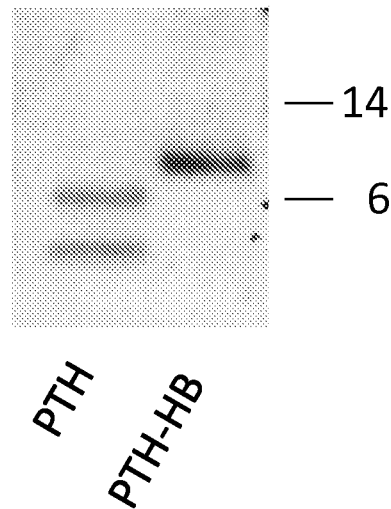
Figure 9B:

Western analysis demonstrated detection of both PTH and PTH-HB peptide (FIG. 9A). After two days of incubation in the absence of PTH peptides, there was only faint detection of PTH remaining in the tissue (FIG. 9B). In contrast, there was strong detection of PTH-eHB peptide remaining in the tissue (FIG. 9B). Furthermore, the PTH-HB peptide remained highly abundant in the tissue after four days of incubation in the absence of PTH peptides (data not shown). Again, there was only faint detection of the PTH peptide (data not shown).

Accordingly, the inventors have demonstrated herein that modification of PTH (1-34) peptide by fusion to the heparin binding sequence "KRKKKGKGLGKKRDPRLRKYK" (SEQ ID NO: 2) allows for extended retention of the PTH peptide in cartilage tissue. Accordingly, a PTH-HB peptide can be retained in the cartilage tissue for preventing cartridge loss after injury or during OA.

REFERENCES

The references cited herein and throughout the specification are incorporated herein in their entireties by references.

Chang, J.-K., Chang, L.-H., Hung, S.-H., Wu, S.-C., Lee, H.-Y., Lin, Y.-S., Chen, C.-H., Fu, Y.-C., Wang, G.-J., and Ho, M.-L. (2009). Parathyroid hormone 1-34 inhibits terminal differentiation of human articular chondrocytes and osteoarthritis progression in rats. Arthritis Rheum. 60, 3049-3060.

The invention claimed is:

1. A composition comprising:
    at least one heparin binding (HB) peptide selected from the group consisting of KRKKKGKGLGKKRDPRL-RKYK (SEQ ID NO:2) and KRKKKGKGLGKKRDP-KLRKYK (SEQ ID NO:3); and
    an active agent (X) linked to the HB peptide, wherein X is selected from the group consisting of a chemical entity to be administered to a subject to treat a condition and a biological product to be administered to a subject to treat a condition.

2. The composition of claim 1, further comprising a linker, wherein the composition is represented by (HB-linker)n-Xn, where n is an integer of at least 1.

3. The composition of claim 2, wherein the linker is a peptide comprising the sequence GGG.

4. The composition of claim 3, wherein the HB-linker portion of the composition is selected from KRKKKGKGLGKKRDPRL-RKYKGGGKRKKKGKGLGKKRDPRLRKYK (SEQ ID NO:4) and KRKKKGKGLGKKRDPRL-RKYKGGGKRKKKGKGLGKKRDPRL-RKYKGGGKRKKKGK GLGKKRDPRLRKYK (SEQ ID NO:5).

5. The composition of claim 2, wherein (HB-linker)n-Xn is a fusion protein.

6. The composition of claim 5, wherein the fusion protein is selected from the group consisting of:

(SEQ ID NO: 10)
KRKKKGKGLGKKRDPRLRKYKGGGKRKKKGKGLGKKRDPRLRKYKGPETL

CGAELVDALQFVCGDRGFYFNKPTGYGSSSRRAPQTGIVDECCFRSCDLR

RLEMYCAPLKPAKSARSVRAQRHTDMPKTQKEVHLKNASRGSA;

(SEQ ID NO: 11)
KRKKKGKGLGKKRDPRLRKYKGGGKRKKKGKGLGKKRDPRLRKYKGGGKR

KKKGKGLGKKRDPRLRKYKGPETLCGAELVDALQFVCGDRGFYFNKPTGY

GSSSRRAPQTGIVDECCFRSCDLRRLEMYCAPLKPAKSARSVRAQRHTDM

PKTQKEVHLKNASRGSA;

(SEQ ID NO: 12)
MKRKKKGKGLGKKRDPRLRKYKGPETLCGAELVDALQFVCGDRGFYFNKP

TGYGSSSRRAPQTGIVDECCFRSCDLRRLEMYCAPLKPAKSARSVRAQRH

TDMPKTQKEVHLKNASRGSA;

(SEQ ID NO: 13)
MKRKKKGKGLGKKRDPKLRKYKGPETLCGAELVDALQFVCGDRGFYFNKP

TGYGSSSRRAPQTGIVDECCFRSCDLRRLEMYCAPLKPAKSARSVRAQRH

TDMPKTQKEVHLKNASRGSA;

(SEQ ID NO: 14)
MKRKKKGKGLGKKRDPRLRKYKGPETLCGAELVDALQFVCGDRGFYFNKP

TGYGSSSRRAPQTGIVDECCFRSCDLRRLEMYCAPLKPAKSA;

(SEQ ID NO: 15)
MKRKKKGKGLGKKRDPKLRKYKGPETLCGAELVDALQFVCGDRGFYFNKP

TGYGSSSRRAPQTGIVDECCFRSCDLRRLEMYCAPLKPAKSA;

(SEQ ID NO: 16)
KRKKKGKGLGKKRDPRLRKYKGPETLCGAELVDALQFVCGDRGFYFNKPT

GYGSSSRRAPQTGIVDECCFRSCDLRRLEMYCAPLKPAKSARSVRAQRHT

DMPKTQKEVHLKNASRGSA;

(SEQ ID NO: 17)
KRKKKGKGLGKKRDPKLRKYKGPETLCGAELVDALQFVCGDRGFYFNKPT

GYGSSSRRAPQTGIVDECCFRSCDLRRLEMYCAPLKPAKSARSVRAQRHT

DMPKTQKEVHLKNASRGSA;

(SEQ ID NO: 18)
KRKKKGKGLGKKRDPRLRKYKGPETLCGAELVDALQFVCGDRGFYFNKPT

GYGSSSRRAPQTGIVDECCFRSCDLRRLEMYCAPLKPAKSA;
or (SEQ ID NO: 19)
KRKKKGKGLGKKRDPKLRKYKGPETLCGAELVDALQFVCGDRGFYFNKPT

GYGSSSRRAPQTGIVDECCFRSCDLRRLEMYCAPLKPAKSA.

7. The composition of claim 5, wherein X is selected from any one or a combination of proteins from the group consisting of: SEQ ID NO: 6-9, SEQ ID NO: 30-41, SEQ ID NO: 63, and SEQ ID NO: 73-76.

8. The composition of claim 2, wherein X or linker is fused to the N-terminus of HB.

9. The composition of claim 2, wherein X or linker is fused to the C-terminus of HB.

10. The composition of claim 1, wherein X is a protein or a portion of a protein selected from the group consisting of nerve growth factor (NGF); brain-derived neurotrophic factor (BDNF); neurotrophin-3 (NT-3); neurotrophin-4 (NT-4); Ciliary neurotrophic factor (CNTF); mesencephalic astrocyte-derived neurotrophic factor (MANF); conserved dopamine neurotrophic factor (CDNF); glial cell line-derived neurotrophic factor (GDNF); neurturin (NRTN); artemin (ARTN); or persephin (PSPN); interleukin-6; interleukin-11; interleukin-27; leukaemia inhibitory factor; cardiotrophin 1; neuropoietin; cardiotrophin-like cytokine; Fibroblast Growth Factor 2; interleukin-4; interleukin-10; Neuregulin-1; Vascular endothelial growth factor (VEGF); Cerebrolysin® (FPF-1070); Etanercept (Enbrel®, soluble recombinant TNF receptor 2 fused to the Fc component of human immunoglobulin G1); Growth differentiation factor 11 (GDF11); Stromal cell-derived factor-1 (SDF-1); Myostatin (growth differentiation factor 8 (GDF8)); Parathyroid hormone (PTH); Parathyroid hormone related peptide (PTHrP); Interleukin 1 receptor antagonist (IL-IRA); Fibroblast growth factor 18 (FGF-18); High-mobility group protein 2 (HMG-2, also known as High mobility group box 2 (HMGB2)); Glucocorticoid receptor; Remicade® (infliximab, anti-TNF-α, Janssen Biotech, Horsham, Pa.); Humira® (adalimumab, anti-TNF, Abbot Labs., N. Chicago, Ill.); Fibroblast growth factor 9 (FGF-9); Hepatocyte growth factor; TGFβ; TGFPβ3; BMP2; BMP7; somatostatin octreotide; pasireotide; lanreotide; and kartogenin.

11. The composition of claim 1, wherein X is IL-1RA or an IL-1RA chimera.

12. The composition of claim 1, further comprising at least two X, wherein X is fused to both the N-terminus and the C terminus of HB, optionally including at least one linker peptide.

13. The composition of claim 1, wherein X is a small molecule.

14. The composition of claim 1, comprising at least two HB peptides, the two HB peptides fused respectively to the N-terminus and the C terminus of X, wherein the fusion of HB to the N or C terminus optionally includes at least one linker peptide.

15. The composition of claim 1, wherein the composition is represented by (HB-linker)n-Xm-(HB-linker)o, wherein m is an integer of at least 1, and n+o is an integer of at least 1.

16. The composition of claim 15, further comprising two or more different HB peptides selected from the group consisting of krkkkgkglgkkrdpclrkyk (SEQ ID NO:1), krkkkgkglgkkrdprlrkyk (SEQ ID NO:2), and krkkkgkglgkkrdpklrkyk (SEQ ID NO:3).

17. The composition of claim 1, wherein the composition comprises at least 2 HBn-Xn conjugates.

18. The composition of claim 1, for delivering an active agent X to a cell or tissue expressing proteoglycans.

19. The composition of claim 18, wherein the tissue is cartilage tissue, neuronal tissue, skin or subcutaneous tissue.

20. The composition of claim 1, wherein the composition comprises a hydrogel.

21. The composition of claim 20, wherein the hydrogel is a self-assembly peptide hydrogel.

22. The composition of claim 21, wherein the self-assembly peptide hydrogel comprises at least one or a combination of peptides selected from the group consisting of: RADARADARADARADA (SEQ ID NO: 77), KLDLKLDLKLDL (SEQ ID NO: 78) and AcN-KLDLKLDLKLDL-CNH2 (SEQ ID NO: 79).

23. The composition of claim 1, wherein X is IGF-1.

24. The composition of claim 1, wherein X comprises a steroidal anti-inflammatory agent.

25. The composition of claim 24, wherein the steroidal anti-inflammatory agent is selected from the group consisting of 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, fluclorinide, flumethasone, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, and triamcinolone hexacetonide.

* * * * *

SEQUENCE LISTING

<160> NUMBER OF SEQ ID NOS: 82

<210> SEQ ID NO 1

```
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Arg Lys Lys Lys Gly Lys Gly Leu Gly Lys Lys Arg Asp Pro Cys
1               5                   10                  15

Leu Arg Lys Tyr Lys
            20

<210> SEQ ID NO 2
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Arg Lys Lys Lys Gly Lys Gly Leu Gly Lys Lys Arg Asp Pro Arg
1               5                   10                  15

Leu Arg Lys Tyr Lys
            20

<210> SEQ ID NO 3
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Arg Lys Lys Lys Gly Lys Gly Leu Gly Lys Lys Arg Asp Pro Lys
1               5                   10                  15

Leu Arg Lys Tyr Lys
            20

<210> SEQ ID NO 4
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Lys Arg Lys Lys Lys Gly Lys Gly Leu Gly Lys Lys Arg Asp Pro Arg
1               5                   10                  15

Leu Arg Lys Tyr Lys Gly Gly Gly Lys Arg Lys Lys Lys Gly Lys Gly
            20                  25                  30

Leu Gly Lys Lys Arg Asp Pro Arg Leu Arg Lys Tyr Lys
        35                  40                  45

<210> SEQ ID NO 5
<211> LENGTH: 69
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5
```

```
Lys Arg Lys Lys Lys Gly Lys Gly Leu Gly Lys Lys Arg Asp Pro Arg
1               5                   10                  15

Leu Arg Lys Tyr Lys Gly Gly Lys Arg Lys Lys Lys Gly Lys Gly
                20                  25                  30

Leu Gly Lys Lys Arg Asp Pro Arg Leu Arg Lys Tyr Lys Gly Gly
            35                  40                  45

Lys Arg Lys Lys Lys Gly Lys Gly Leu Gly Lys Lys Arg Asp Pro Arg
    50                  55                  60

Leu Arg Lys Tyr Lys
65
```

<210> SEQ ID NO 6
<211> LENGTH: 70
<212> TYPE: PRT
<213> ORGANISM: Rattus sp.

<400> SEQUENCE: 6

```
Gly Pro Glu Thr Leu Cys Gly Ala Glu Leu Val Asp Ala Leu Gln Phe
1               5                   10                  15

Val Cys Gly Pro Arg Gly Phe Tyr Phe Asn Lys Pro Thr Gly Tyr Gly
                20                  25                  30

Ser Ser Ile Arg Arg Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
    50                  55                  60

Lys Pro Thr Lys Ser Ala
65                  70
```

<210> SEQ ID NO 7
<211> LENGTH: 98
<212> TYPE: PRT
<213> ORGANISM: Homo sapiens

<400> SEQUENCE: 7

```
Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
    50                  55                  60

Lys Pro Ala Lys Ser Ala Arg Ser Val Arg Ala Gln Arg His Thr Asp
65                  70                  75                  80

Met Pro Lys Thr Gln Lys Glu Val His Leu Lys Asn Ala Ser Arg Gly
                85                  90                  95

Ser Ala
```

<210> SEQ ID NO 8
<211> LENGTH: 70
<212> TYPE: PRT
<213> ORGANISM: Homo sapiens

<400> SEQUENCE: 8

```
Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
```

```
                    20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
        50                  55                  60

Lys Pro Ala Lys Ser Ala
65                  70

<210> SEQ ID NO 9
<211> LENGTH: 72
<212> TYPE: PRT
<213> ORGANISM: Homo sapiens

<400> SEQUENCE: 9

Met Glu Gly Pro Glu Thr Leu Cys Gly Ala Glu Leu Val Asp Ala Leu
1               5                   10                  15

Gln Phe Val Cys Gly Asp Arg Gly Phe Tyr Phe Asn Lys Pro Thr Gly
                20                  25                  30

Tyr Gly Ser Ser Ser Arg Arg Ala Pro Gln Thr Gly Ile Val Asp Glu
            35                  40                  45

Cys Cys Phe Arg Ser Cys Asp Leu Arg Arg Leu Glu Met Tyr Cys Ala
        50                  55                  60

Pro Leu Lys Pro Ala Lys Ser Ala
65                  70

<210> SEQ ID NO 10
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Lys Arg Lys Lys Lys Gly Lys Gly Leu Gly Lys Lys Arg Asp Pro Arg
1               5                   10                  15

Leu Arg Lys Tyr Lys Gly Gly Gly Lys Arg Lys Lys Gly Lys Gly
                20                  25                  30

Leu Gly Lys Lys Arg Asp Pro Arg Leu Arg Lys Tyr Lys Gly Pro Glu
        35                  40                  45

Thr Leu Cys Gly Ala Glu Leu Val Asp Ala Leu Gln Phe Val Cys Gly
    50                  55                  60

Asp Arg Gly Phe Tyr Phe Asn Lys Pro Thr Gly Tyr Gly Ser Ser Ser
65                  70                  75                  80

Arg Arg Ala Pro Gln Thr Gly Ile Val Asp Glu Cys Cys Phe Arg Ser
                85                  90                  95

Cys Asp Leu Arg Arg Leu Glu Met Tyr Cys Ala Pro Leu Lys Pro Ala
            100                 105                 110

Lys Ser Ala Arg Ser Val Arg Ala Gln Arg His Thr Asp Met Pro Lys
        115                 120                 125

Thr Gln Lys Glu Val His Leu Lys Asn Ala Ser Arg Gly Ser Ala
    130                 135                 140

<210> SEQ ID NO 11
<211> LENGTH: 167
<212> TYPE: PRT
<213> ORGANISM: Artificial Sequence
<220> FEATURE:
<223> OTHER INFORMATION: Description of Artificial Sequence: Synthetic
```

-continued polypeptide

<400> SEQUENCE: 11

Lys Arg Lys Lys Lys Gly Lys Gly Leu Gly Lys Lys Arg Asp Pro Arg
1               5                   10                  15

Leu Arg Lys Tyr Lys Gly Gly Lys Arg Lys Lys Gly Lys Gly
            20                  25                  30

Leu Gly Lys Lys Arg Asp Pro Arg Leu Arg Lys Tyr Lys Gly Gly Gly
        35                  40                  45

Lys Arg Lys Lys Gly Lys Gly Leu Gly Lys Lys Arg Asp Pro Arg
    50                  55                  60

Leu Arg Lys Tyr Lys Gly Pro Glu Thr Leu Cys Gly Ala Glu Leu Val
65                  70                  75                  80

Asp Ala Leu Gln Phe Val Cys Gly Asp Arg Gly Phe Tyr Phe Asn Lys
                85                  90                  95

Pro Thr Gly Tyr Gly Ser Ser Ser Arg Arg Ala Pro Gln Thr Gly Ile
            100                 105                 110

Val Asp Glu Cys Cys Phe Arg Ser Cys Asp Leu Arg Arg Leu Glu Met
        115                 120                 125

Tyr Cys Ala Pro Leu Lys Pro Ala Lys Ser Ala Arg Ser Val Arg Ala
130                 135                 140

Gln Arg His Thr Asp Met Pro Lys Thr Gln Lys Glu Val His Leu Lys
145                 150                 155                 160

Asn Ala Ser Arg Gly Ser Ala
                165

<210> SEQ ID NO 12
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Lys Arg Lys Lys Lys Gly Lys Gly Leu Gly Lys Lys Arg Asp Pro
1               5                   10                  15

Arg Leu Arg Lys Tyr Lys Gly Pro Glu Thr Leu Cys Gly Ala Glu Leu
            20                  25                  30

Val Asp Ala Leu Gln Phe Val Cys Gly Asp Arg Gly Phe Tyr Phe Asn
        35                  40                  45

Lys Pro Thr Gly Tyr Gly Ser Ser Ser Arg Arg Ala Pro Gln Thr Gly
    50                  55                  60

Ile Val Asp Glu Cys Cys Phe Arg Ser Cys Asp Leu Arg Arg Leu Glu
65                  70                  75                  80

Met Tyr Cys Ala Pro Leu Lys Pro Ala Lys Ser Ala Arg Ser Val Arg
                85                  90                  95

Ala Gln Arg His Thr Asp Met Pro Lys Thr Gln Lys Glu Val His Leu
            100                 105                 110

Lys Asn Ala Ser Arg Gly Ser Ala
        115                 120

<210> SEQ ID NO 13
<211> LENGTH: 120
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 13

Met Lys Arg Lys Lys Lys Gly Lys Gly Leu Gly Lys Lys Arg Asp Pro
1               5                   10                  15

Lys Leu Arg Lys Tyr Lys Gly Pro Glu Thr Leu Cys Gly Ala Glu Leu
            20                  25                  30

Val Asp Ala Leu Gln Phe Val Cys Gly Asp Arg Gly Phe Tyr Phe Asn
        35                  40                  45

Lys Pro Thr Gly Tyr Gly Ser Ser Ser Arg Arg Ala Pro Gln Thr Gly
    50                  55                  60

Ile Val Asp Glu Cys Cys Phe Arg Ser Cys Asp Leu Arg Arg Leu Glu
65                  70                  75                  80

Met Tyr Cys Ala Pro Leu Lys Pro Ala Lys Ser Ala Arg Ser Val Arg
                85                  90                  95

Ala Gln Arg His Thr Asp Met Pro Lys Thr Gln Lys Glu Val His Leu
            100                 105                 110

Lys Asn Ala Ser Arg Gly Ser Ala
            115                 120

<210> SEQ ID NO 14
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Lys Arg Lys Lys Lys Gly Lys Gly Leu Gly Lys Lys Arg Asp Pro
1               5                   10                  15

Arg Leu Arg Lys Tyr Lys Gly Pro Glu Thr Leu Cys Gly Ala Glu Leu
            20                  25                  30

Val Asp Ala Leu Gln Phe Val Cys Gly Asp Arg Gly Phe Tyr Phe Asn
        35                  40                  45

Lys Pro Thr Gly Tyr Gly Ser Ser Ser Arg Arg Ala Pro Gln Thr Gly
    50                  55                  60

Ile Val Asp Glu Cys Cys Phe Arg Ser Cys Asp Leu Arg Arg Leu Glu
65                  70                  75                  80

Met Tyr Cys Ala Pro Leu Lys Pro Ala Lys Ser Ala
                85                  90

<210> SEQ ID NO 15
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Lys Arg Lys Lys Lys Gly Lys Gly Leu Gly Lys Lys Arg Asp Pro
1               5                   10                  15

Lys Leu Arg Lys Tyr Lys Gly Pro Glu Thr Leu Cys Gly Ala Glu Leu
            20                  25                  30

Val Asp Ala Leu Gln Phe Val Cys Gly Asp Arg Gly Phe Tyr Phe Asn
        35                  40                  45

Lys Pro Thr Gly Tyr Gly Ser Ser Ser Arg Arg Ala Pro Gln Thr Gly
    50                  55                  60

```
Ile Val Asp Glu Cys Cys Phe Arg Ser Cys Asp Leu Arg Arg Leu Glu
 65                  70                  75                  80

Met Tyr Cys Ala Pro Leu Lys Pro Ala Lys Ser Ala
                 85                  90

<210> SEQ ID NO 16
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Lys Arg Lys Lys Gly Lys Gly Leu Gly Lys Lys Arg Asp Pro Arg
 1               5                  10                  15

Leu Arg Lys Tyr Lys Gly Pro Glu Thr Leu Cys Gly Ala Glu Leu Val
                 20                  25                  30

Asp Ala Leu Gln Phe Val Cys Gly Asp Arg Gly Phe Tyr Phe Asn Lys
             35                  40                  45

Pro Thr Gly Tyr Gly Ser Ser Ser Arg Arg Ala Pro Gln Thr Gly Ile
         50                  55                  60

Val Asp Glu Cys Cys Phe Arg Ser Cys Asp Leu Arg Arg Leu Glu Met
 65                  70                  75                  80

Tyr Cys Ala Pro Leu Lys Pro Ala Lys Ser Ala Arg Ser Val Arg Ala
                 85                  90                  95

Gln Arg His Thr Asp Met Pro Lys Thr Gln Lys Glu Val His Leu Lys
                100                 105                 110

Asn Ala Ser Arg Gly Ser Ala
            115

<210> SEQ ID NO 17
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Lys Arg Lys Lys Gly Lys Gly Leu Gly Lys Lys Arg Asp Pro Lys
 1               5                  10                  15

Leu Arg Lys Tyr Lys Gly Pro Glu Thr Leu Cys Gly Ala Glu Leu Val
                 20                  25                  30

Asp Ala Leu Gln Phe Val Cys Gly Asp Arg Gly Phe Tyr Phe Asn Lys
             35                  40                  45

Pro Thr Gly Tyr Gly Ser Ser Ser Arg Arg Ala Pro Gln Thr Gly Ile
         50                  55                  60

Val Asp Glu Cys Cys Phe Arg Ser Cys Asp Leu Arg Arg Leu Glu Met
 65                  70                  75                  80

Tyr Cys Ala Pro Leu Lys Pro Ala Lys Ser Ala Arg Ser Val Arg Ala
                 85                  90                  95

Gln Arg His Thr Asp Met Pro Lys Thr Gln Lys Glu Val His Leu Lys
                100                 105                 110

Asn Ala Ser Arg Gly Ser Ala
            115

<210> SEQ ID NO 18
```

```
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Lys Arg Lys Lys Lys Gly Lys Gly Leu Gly Lys Lys Arg Asp Pro Arg
1               5                   10                  15

Leu Arg Lys Tyr Lys Gly Pro Glu Thr Leu Cys Gly Ala Glu Leu Val
                20                  25                  30

Asp Ala Leu Gln Phe Val Cys Gly Asp Arg Gly Phe Tyr Phe Asn Lys
            35                  40                  45

Pro Thr Gly Tyr Gly Ser Ser Ser Arg Arg Ala Pro Gln Thr Gly Ile
    50                  55                  60

Val Asp Glu Cys Cys Phe Arg Ser Cys Asp Leu Arg Arg Leu Glu Met
65                  70                  75                  80

Tyr Cys Ala Pro Leu Lys Pro Ala Lys Ser Ala
                85                  90

<210> SEQ ID NO 19
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Lys Arg Lys Lys Lys Gly Lys Gly Leu Gly Lys Lys Arg Asp Pro Lys
1               5                   10                  15

Leu Arg Lys Tyr Lys Gly Pro Glu Thr Leu Cys Gly Ala Glu Leu Val
                20                  25                  30

Asp Ala Leu Gln Phe Val Cys Gly Asp Arg Gly Phe Tyr Phe Asn Lys
            35                  40                  45

Pro Thr Gly Tyr Gly Ser Ser Ser Arg Arg Ala Pro Gln Thr Gly Ile
    50                  55                  60

Val Asp Glu Cys Cys Phe Arg Ser Cys Asp Leu Arg Arg Leu Glu Met
65                  70                  75                  80

Tyr Cys Ala Pro Leu Lys Pro Ala Lys Ser Ala
                85                  90

<210> SEQ ID NO 20
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Met Lys Arg Lys Lys Lys Gly Lys Gly Leu Gly Lys Lys Arg Asp Pro
1               5                   10                  15

Cys Leu Arg Lys Tyr Lys
                20

<210> SEQ ID NO 21
<211> LENGTH: 22
<212> TYPE: PRT
<213> ORGANISM: Artificial Sequence
<220> FEATURE:
```

<223> OTHER INFORMATION: Description of Artificial Sequence: Synthetic
    peptide

<400> SEQUENCE: 21

Met Lys Arg Lys Lys Lys Gly Lys Gly Leu Gly Lys Lys Arg Asp Pro
1               5                   10                  15

Arg Leu Arg Lys Tyr Lys
            20

<210> SEQ ID NO 22
<211> LENGTH: 22
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 22

Met Lys Arg Lys Lys Lys Gly Lys Gly Leu Gly Lys Lys Arg Asp Pro
1               5                   10                  15

Lys Leu Arg Lys Tyr Lys
            20

<210> SEQ ID NO 23
<211> LENGTH: 45
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 23

Lys Arg Lys Lys Lys Gly Lys Gly Leu Gly Lys Lys Arg Asp Pro Lys
1               5                   10                  15

Leu Arg Lys Tyr Lys Gly Gly Gly Lys Arg Lys Lys Gly Lys Gly
            20                  25                  30

Leu Gly Lys Lys Arg Asp Pro Lys Leu Arg Lys Tyr Lys
            35                  40                  45

<210> SEQ ID NO 24
<211> LENGTH: 69
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 24

Lys Arg Lys Lys Lys Gly Lys Gly Leu Gly Lys Lys Arg Asp Pro Lys
1               5                   10                  15

Leu Arg Lys Tyr Lys Gly Gly Gly Lys Arg Lys Lys Gly Lys Gly
            20                  25                  30

Leu Gly Lys Lys Arg Asp Pro Lys Leu Arg Lys Tyr Lys Gly Gly Gly
            35                  40                  45

Lys Arg Lys Lys Lys Gly Lys Gly Leu Gly Lys Lys Arg Asp Pro Lys
    50                  55                  60

Leu Arg Lys Tyr Lys
65

<210> SEQ ID NO 25
<211> LENGTH: 115
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 25

Lys Arg Lys Lys Lys Gly Lys Gly Leu Gly Lys Lys Arg Asp Pro Arg
1               5                   10                  15

Leu Arg Lys Tyr Lys Gly Gly Gly Lys Arg Lys Lys Lys Gly Lys Gly
                20                  25                  30

Leu Gly Lys Lys Arg Asp Pro Arg Leu Arg Lys Tyr Lys Gly Pro Glu
            35                  40                  45

Thr Leu Cys Gly Ala Glu Leu Val Asp Ala Leu Gln Phe Val Cys Gly
        50                  55                  60

Asp Arg Gly Phe Tyr Phe Asn Lys Pro Thr Gly Tyr Gly Ser Ser Ser
65                  70                  75                  80

Arg Arg Ala Pro Gln Thr Gly Ile Val Asp Glu Cys Cys Phe Arg Ser
                85                  90                  95

Cys Asp Leu Arg Arg Leu Glu Met Tyr Cys Ala Pro Leu Lys Pro Ala
            100                 105                 110

Lys Ser Ala
        115

<210> SEQ ID NO 26
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Lys Arg Lys Lys Lys Gly Lys Gly Leu Gly Lys Lys Arg Asp Pro Arg
1               5                   10                  15

Leu Arg Lys Tyr Lys Gly Gly Gly Lys Arg Lys Lys Lys Gly Lys Gly
                20                  25                  30

Leu Gly Lys Lys Arg Asp Pro Arg Leu Arg Lys Tyr Lys Gly Gly Gly
            35                  40                  45

Lys Arg Lys Lys Lys Gly Lys Gly Leu Gly Lys Lys Arg Asp Pro Arg
        50                  55                  60

Leu Arg Lys Tyr Lys Gly Pro Glu Thr Leu Cys Gly Ala Glu Leu Val
65                  70                  75                  80

Asp Ala Leu Gln Phe Val Cys Gly Asp Arg Gly Phe Tyr Phe Asn Lys
                85                  90                  95

Pro Thr Gly Tyr Gly Ser Ser Ser Arg Arg Ala Pro Gln Thr Gly Ile
            100                 105                 110

Val Asp Glu Cys Cys Phe Arg Ser Cys Asp Leu Arg Arg Leu Glu Met
        115                 120                 125

Tyr Cys Ala Pro Leu Lys Pro Ala Lys Ser Ala
            130                 135

<210> SEQ ID NO 27
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27
```

Lys Arg Lys Lys Lys Gly Lys Gly Leu Gly Lys Lys Arg Asp Pro Lys
1               5                   10                  15

Leu Arg Lys Tyr Lys Gly Gly Lys Arg Lys Lys Gly Lys Gly
            20                  25                  30

Leu Gly Lys Lys Arg Asp Pro Lys Leu Arg Lys Tyr Lys Gly Pro Glu
            35                  40                  45

Thr Leu Cys Gly Ala Glu Leu Val Asp Ala Leu Gln Phe Val Cys Gly
            50                  55                  60

Asp Arg Gly Phe Tyr Phe Asn Lys Pro Thr Gly Tyr Gly Ser Ser Ser
65                  70                  75                  80

Arg Arg Ala Pro Gln Thr Gly Ile Val Asp Glu Cys Cys Phe Arg Ser
            85                  90                  95

Cys Asp Leu Arg Arg Leu Glu Met Tyr Cys Ala Pro Leu Lys Pro Ala
            100                 105                 110

Lys Ser Ala Arg Ser Val Arg Ala Gln Arg His Thr Asp Met Pro Lys
            115                 120                 125

Thr Gln Lys Glu Val His Leu Lys Asn Ala Ser Arg Gly Ser Ala
            130                 135                 140

<210> SEQ ID NO 28
<211> LENGTH: 167
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Lys Arg Lys Lys Lys Gly Lys Gly Leu Gly Lys Lys Arg Asp Pro Lys
1               5                   10                  15

Leu Arg Lys Tyr Lys Gly Gly Lys Arg Lys Lys Gly Lys Gly
            20                  25                  30

Leu Gly Lys Lys Arg Asp Pro Lys Leu Arg Lys Tyr Lys Gly Gly Gly
            35                  40                  45

Lys Arg Lys Lys Gly Lys Gly Leu Gly Lys Lys Arg Asp Pro Lys
50                  55                  60

Leu Arg Lys Tyr Lys Gly Pro Glu Thr Leu Cys Gly Ala Glu Leu Val
65                  70                  75                  80

Asp Ala Leu Gln Phe Val Cys Gly Asp Arg Gly Phe Tyr Phe Asn Lys
            85                  90                  95

Pro Thr Gly Tyr Gly Ser Ser Ser Arg Arg Ala Pro Gln Thr Gly Ile
            100                 105                 110

Val Asp Glu Cys Cys Phe Arg Ser Cys Asp Leu Arg Arg Leu Glu Met
            115                 120                 125

Tyr Cys Ala Pro Leu Lys Pro Ala Lys Ser Ala Arg Ser Val Arg Ala
            130                 135                 140

Gln Arg His Thr Asp Met Pro Lys Thr Gln Lys Glu Val His Leu Lys
145                 150                 155                 160

Asn Ala Ser Arg Gly Ser Ala
            165

<210> SEQ ID NO 29
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Lys Arg Lys Lys Lys Gly Lys Gly Leu Gly Lys Lys Arg Asp Pro Lys
1               5                   10                  15

Leu Arg Lys Tyr Lys Gly Gly Lys Arg Lys Lys Gly Lys Gly
            20                  25                  30

Leu Gly Lys Lys Arg Asp Pro Lys Leu Arg Lys Tyr Lys Gly Pro Glu
        35                  40                  45

Thr Leu Cys Gly Ala Glu Leu Val Asp Ala Leu Gln Phe Val Cys Gly
        50                  55                  60

Asp Arg Gly Phe Tyr Phe Asn Lys Pro Thr Gly Tyr Gly Ser Ser Ser
65                  70                  75                  80

Arg Arg Ala Pro Gln Thr Gly Ile Val Asp Glu Cys Cys Phe Arg Ser
            85                  90                  95

Cys Asp Leu Arg Arg Leu Glu Met Tyr Cys Ala Pro Leu Lys Pro Ala
            100                 105                 110

Lys Ser Ala
        115

<210> SEQ ID NO 30
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Lys Arg Lys Lys Lys Gly Lys Gly Leu Gly Lys Lys Arg Asp Pro Lys
1               5                   10                  15

Leu Arg Lys Tyr Lys Gly Gly Lys Arg Lys Lys Gly Lys Gly
            20                  25                  30

Leu Gly Lys Lys Arg Asp Pro Lys Leu Arg Lys Tyr Lys Gly Gly Gly
        35                  40                  45

Lys Arg Lys Lys Gly Lys Gly Leu Gly Lys Lys Arg Asp Pro Lys
50                  55                  60

Leu Arg Lys Tyr Lys Gly Pro Glu Thr Leu Cys Gly Ala Glu Leu Val
65                  70                  75                  80

Asp Ala Leu Gln Phe Val Cys Gly Asp Arg Gly Phe Tyr Phe Asn Lys
            85                  90                  95

Pro Thr Gly Tyr Gly Ser Ser Ser Arg Arg Ala Pro Gln Thr Gly Ile
            100                 105                 110

Val Asp Glu Cys Cys Phe Arg Ser Cys Asp Leu Arg Arg Leu Glu Met
        115                 120                 125

Tyr Cys Ala Pro Leu Lys Pro Ala Lys Ser Ala
            130                 135

<210> SEQ ID NO 31
<211> LENGTH: 180
<212> TYPE: PRT
<213> ORGANISM: Homo sapiens

<400> SEQUENCE: 31

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
            20                  25                  30

Arg Thr Ser Gly Lys His Ile Gln Val Leu Gly Arg Ile Ser Ala
        35                  40                  45

Arg Gly Glu Asp Gly Asp Lys Tyr Ala Gln Leu Leu Val Glu Thr Asp
    50                  55                  60

Thr Phe Gly Ser Gln Val Arg Ile Lys Gly Lys Glu Thr Glu Phe Tyr
65              70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
                100                 105                 110

Ala Leu Met Ser Ala Lys Tyr Ser Gly Trp Tyr Val Gly Phe Thr Lys
            115                 120                 125

Lys Gly Arg Pro Arg Lys Gly Pro Lys Thr Arg Glu Asn Gln Gln Asp
        130                 135                 140

Val His Phe Met Lys Arg Tyr Pro Lys Gly Gln Pro Glu Leu Gln Lys
145                 150                 155                 160

Pro Phe Lys Tyr Thr Thr Val Thr Lys Arg Ser Arg Arg Ile Arg Pro
                165                 170                 175

Thr His Pro Ala
            180

<210> SEQ ID NO 32
<211> LENGTH: 84
<212> TYPE: PRT
<213> ORGANISM: Homo sapiens

<400> SEQUENCE: 32

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
        50                  55                  60

Lys Ser Leu Gly Glu Ala Asp Lys Ala Asp Val Asn Val Leu Thr Lys
65                  70                  75                  80

Ala Lys Ser Gln

<210> SEQ ID NO 33
<211> LENGTH: 34
<212> TYPE: PRT
<213> ORGANISM: Homo sapiens

<400> SEQUENCE: 33

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe

<210> SEQ ID NO 34
<211> LENGTH: 31
<212> TYPE: PRT
<213> ORGANISM: Homo sapiens

<400> SEQUENCE: 34

```
Ser Val Ser Glu Ile Gln Leu Met His Asn Leu Gly Lys His Leu Asn
1               5                   10                  15
Ser Met Glu Arg Val Glu Trp Leu Arg Lys Lys Leu Gln Asp Val
            20                  25                  30
```

<210> SEQ ID NO 35
<211> LENGTH: 37
<212> TYPE: PRT
<213> ORGANISM: Homo sapiens

<400> SEQUENCE: 35

```
Ser Val Ser Glu Ile Gln Leu Met His Asn Leu Gly Lys His Leu Asn
1               5                   10                  15
Ser Met Glu Arg Val Glu Trp Leu Arg Lys Lys Leu Gln Asp Val His
            20                  25                  30
Asn Phe Val Ala Leu
        35
```

<210> SEQ ID NO 36
<211> LENGTH: 44
<212> TYPE: PRT
<213> ORGANISM: Homo sapiens

<400> SEQUENCE: 36

```
Ser Val Ser Glu Ile Gln Leu Met His Asn Leu Gly Lys His Leu Asn
1               5                   10                  15
Ser Met Glu Arg Val Glu Trp Leu Arg Lys Lys Leu Gln Asp Val His
            20                  25                  30
Asn Phe Val Ala Leu Gly Ala Pro Leu Ala Pro Arg
        35                  40
```

<210> SEQ ID NO 37
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

```
Ser Val Ser Glu Ile Gln Leu Met His Asn Leu Gly Lys His Leu Asn
1               5                   10                  15
Ser Met Glu Arg Val Glu Trp Leu Arg Lys Lys Leu Gln Asp Val His
            20                  25                  30
Asn Phe Gly Gly Gly Lys Arg Lys Lys Lys Gly Lys Gly Leu Gly Lys
        35                  40                  45
Lys Arg Asp Pro Arg Leu Arg Lys Tyr Lys
    50                  55
```

<210> SEQ ID NO 38
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

```
Ala Val Ser Glu His Gln Leu Leu His Asp Lys Gly Lys Ser Ile Gln
1               5                   10                  15
Asp Leu Arg Arg Arg Phe Phe Leu His His Leu Ile Ala Glu Ile His
            20                  25                  30
```

```
Thr Ala Glu Ile Arg Ala Thr Ser Glu Val Ser Pro Asn Ser Lys Pro
        35                  40                  45

Ser Pro Asn Thr Lys Asn His Pro Val Arg Phe Gly Ser Asp Asp Glu
    50                  55                  60

Gly Arg Tyr Leu Thr Gln Glu Thr Asn Lys Val Glu Thr Tyr Lys Glu
65                  70                  75                  80

Gln Pro Leu Lys Thr Pro
                85

<210> SEQ ID NO 39
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (29)..(29)
<223> OTHER INFORMATION: Aib

<400> SEQUENCE: 39

Ala Val Ser Glu His Gln Leu Leu His Asp Lys Gly Lys Ser Ile Gln
1               5                   10                  15

Asp Leu Arg Arg Arg Glu Leu Leu Glu Lys Leu Leu Xaa Lys Leu His
                20                  25                  30

Thr Ala

<210> SEQ ID NO 40
<211> LENGTH: 152
<212> TYPE: PRT
<213> ORGANISM: Homo sapiens

<400> SEQUENCE: 40

Arg Pro Ser Gly Arg Lys Ser Ser Lys Met Gln Ala Phe Arg Ile Trp
1               5                   10                  15

Asp Val Asn Gln Lys Thr Phe Tyr Leu Arg Asn Asn Gln Leu Val Ala
                20                  25                  30

Gly Tyr Leu Gln Gly Pro Asn Val Asn Leu Glu Glu Lys Ile Asp Val
            35                  40                  45

Val Pro Ile Glu Pro His Ala Leu Phe Leu Gly Ile His Gly Gly Lys
        50                  55                  60

Met Cys Leu Ser Cys Val Lys Ser Gly Asp Glu Thr Arg Leu Gln Leu
65                  70                  75                  80

Glu Ala Val Asn Ile Thr Asp Leu Ser Glu Asn Arg Lys Gln Asp Lys
                85                  90                  95

Arg Phe Ala Phe Ile Arg Ser Asp Ser Gly Pro Thr Thr Ser Phe Glu
            100                 105                 110

Ser Ala Ala Cys Pro Gly Trp Phe Leu Cys Thr Ala Met Glu Ala Asp
        115                 120                 125

Gln Pro Val Ser Leu Thr Asn Met Pro Asp Glu Gly Val Met Val Thr
    130                 135                 140

Lys Phe Tyr Phe Gln Glu Asp Glu
145                 150

<210> SEQ ID NO 41
<211> LENGTH: 22
<212> TYPE: PRT
<213> ORGANISM: Homo sapiens
```

<400> SEQUENCE: 41

Met Lys Arg Lys Lys Lys Gly Lys Gly Leu Gly Lys Lys Arg Asp Pro
1               5                   10                  15

Ser Leu Arg Lys Tyr Lys
            20

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Gly Gly Gly Ser
1               5

<210> SEQ ID NO 43
<211> LENGTH: 31
<212> TYPE: PRT
<213> ORGANISM: Homo sapiens

<400> SEQUENCE: 43

Ser Cys Ser Val Ala Asp Trp Gln Met Pro Pro Tyr Val Val Leu
1               5                   10                  15

Asp Leu Pro Gln Glu Thr Leu Glu Glu Glu Thr Pro Gly Ala Asn
            20                  25                  30

<210> SEQ ID NO 44
<211> LENGTH: 31
<212> TYPE: PRT
<213> ORGANISM: Homo sapiens

<400> SEQUENCE: 44

Ser Cys Cys Val Ala Asp Trp Gln Met Pro Pro Tyr Val Val Leu
1               5                   10                  15

Asp Leu Pro Gln Glu Thr Leu Glu Glu Glu Thr Pro Gly Ala Asn
            20                  25                  30

<210> SEQ ID NO 45
<211> LENGTH: 26
<212> TYPE: PRT
<213> ORGANISM: Homo sapiens

<400> SEQUENCE: 45

Asp Trp Gln Met Pro Pro Pro Tyr Val Val Leu Asp Leu Pro Gln Glu
1               5                   10                  15

Thr Leu Glu Glu Glu Thr Pro Gly Ala Asn
            20                  25

<210> SEQ ID NO 46
<211> LENGTH: 31
<212> TYPE: PRT
<213> ORGANISM: Homo sapiens

<400> SEQUENCE: 46

Ser Cys Cys Val Ala Asp Trp Gln Met Pro Pro Tyr Val Val Leu
1               5                   10                  15

Asp Leu Pro Gln Glu Thr Leu Glu Glu Glu Thr Pro Gly Ala Asn
            20                  25                  30

<210> SEQ ID NO 47
<211> LENGTH: 27
<212> TYPE: PRT
<213> ORGANISM: Homo sapiens

<400> SEQUENCE: 47

Tyr Leu Ala Met Thr Pro Leu Ile Pro Gln Ser Lys Asp Glu Asn Ser
1               5                   10                  15

Asp Asp Tyr Thr Thr Phe Asp Asp Val Gly Ser
            20                  25

<210> SEQ ID NO 48
<211> LENGTH: 15
<212> TYPE: PRT
<213> ORGANISM: Homo sapiens

<400> SEQUENCE: 48

Glu Leu Asp Val Cys Val Glu Glu Ala Glu Gly Glu Ala Pro Trp
1               5                   10                  15

<210> SEQ ID NO 49
<211> LENGTH: 18
<212> TYPE: PRT
<213> ORGANISM: Homo sapiens

<400> SEQUENCE: 49

Glu Leu Gln Leu Glu Glu Ser Cys Ala Glu Ala Gln Asp Gly Glu Leu
1               5                   10                  15

Asp Gly

<210> SEQ ID NO 50
<211> LENGTH: 13
<212> TYPE: PRT
<213> ORGANISM: Homo sapiens

<400> SEQUENCE: 50

Glu Gly Glu Val Ser Ala Asp Glu Glu Gly Phe Glu Asn
1               5                   10

<210> SEQ ID NO 51
<211> LENGTH: 19
<212> TYPE: PRT
<213> ORGANISM: Homo sapiens

<400> SEQUENCE: 51

Lys Pro Thr His Val Asn Val Ser Val Val Met Ala Glu Val Asp Gly
1               5                   10                  15

Thr Cys Tyr

<210> SEQ ID NO 52
<211> LENGTH: 19
<212> TYPE: PRT
<213> ORGANISM: Homo sapiens

<400> SEQUENCE: 52

Lys Pro Thr His Val Asn Val Ser Val Val Met Ala Glu Val Asp Gly
1               5                   10                  15

Thr Cys Tyr

<210> SEQ ID NO 53
<211> LENGTH: 9
<212> TYPE: PRT

```
<213> ORGANISM: Homo sapiens

<400> SEQUENCE: 53

Tyr Val Thr Asp His Gly Pro Met Lys
1               5

<210> SEQ ID NO 54
<211> LENGTH: 18
<212> TYPE: PRT
<213> ORGANISM: Homo sapiens

<400> SEQUENCE: 54

Pro Thr Leu Tyr Asn Val Ser Leu Val Met Ser Asp Thr Ala Gly Thr
1               5                   10                  15

Cys Tyr

<210> SEQ ID NO 55
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Ser, Ala or Gly

<400> SEQUENCE: 55

Ser Xaa Ser Val Ala Asp Trp Gln Met Pro Pro Tyr Val Val Leu
1               5                   10                  15

Asp Leu Pro Gln Glu Thr Leu Glu Glu Glu Thr Pro Gly Ala Asn
                20                  25                  30

<210> SEQ ID NO 56
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(3)
<223> OTHER INFORMATION: Ser, Ala or Gly

<400> SEQUENCE: 56

Ser Xaa Xaa Val Ala Asp Trp Gln Met Pro Pro Tyr Val Val Leu
1               5                   10                  15

Asp Leu Pro Gln Glu Thr Leu Glu Glu Glu Thr Pro Gly Ala Asn
                20                  25                  30

<210> SEQ ID NO 57
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(3)
<223> OTHER INFORMATION: Ser, Ala or Gly

<400> SEQUENCE: 57

Ser Xaa Xaa Val Ala Asp Trp Gln Met Pro Pro Tyr Val Val Leu
1               5                   10                  15
```

-continued

Asp Leu Pro Gln Glu Thr Leu Glu Glu Glu Thr Pro Gly Ala Asn
            20                  25                  30

<210> SEQ ID NO 58
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ser, Ala or Gly

<400> SEQUENCE: 58

Glu Leu Asp Val Xaa Val Glu Glu Ala Glu Gly Glu Ala Pro Trp
1               5                   10                  15

<210> SEQ ID NO 59
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Ser, Ala or Gly

<400> SEQUENCE: 59

Glu Leu Gln Leu Glu Glu Ser Xaa Ala Glu Ala Gln Asp Gly Glu Leu
1               5                   10                  15

Asp Gly

<210> SEQ ID NO 60
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Ser, Ala or Gly

<400> SEQUENCE: 60

Lys Pro Thr His Val Asn Val Ser Val Val Met Ala Glu Val Asp Gly
1               5                   10                  15

Thr Xaa Tyr

<210> SEQ ID NO 61
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Ser, Ala or Gly

<400> SEQUENCE: 61

Lys Pro Thr His Val Asn Val Ser Val Val Met Ala Glu Val Asp Gly
1               5                   10                  15

Thr Xaa Tyr

<210> SEQ ID NO 62
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Ser, Ala or Gly

<400> SEQUENCE: 62

Pro Thr Leu Tyr Asn Val Ser Leu Val Met Ser Asp Thr Ala Gly Thr
1               5                   10                  15

Xaa Tyr

<210> SEQ ID NO 63
<211> LENGTH: 67
<212> TYPE: PRT
<213> ORGANISM: Homo sapiens

<400> SEQUENCE: 63

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
                20                  25                  30

Arg Arg Ala Pro Gln Thr Gly Ile Val Asp Glu Cys Cys Phe Arg Ser
            35                  40                  45

Cys Asp Leu Arg Arg Leu Glu Met Tyr Cys Ala Pro Leu Lys Pro Ala
50                  55                  60

Lys Ser Ala
65

<210> SEQ ID NO 64
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Lys Arg Lys Lys Lys Gly Lys Gly Leu Gly Lys Lys Arg Asp Pro Arg
1               5                   10                  15

Leu Arg Lys Tyr Lys Thr Leu Cys Gly Ala Glu Leu Val Asp Ala Leu
                20                  25                  30

Gln Phe Val Cys Gly Asp Arg Gly Phe Tyr Phe Asn Lys Pro Thr Gly
            35                  40                  45

Tyr Gly Ser Ser Ser Arg Arg Ala Pro Gln Thr Gly Ile Val Asp Glu
        50                  55                  60

Cys Cys Phe Arg Ser Cys Asp Leu Arg Arg Leu Glu Met Tyr Cys Ala
65                  70                  75                  80

Pro Leu Lys Pro Ala Lys Ser Ala Arg Ser Val Arg Ala Gln Arg His
                85                  90                  95

Thr Asp Met Pro Lys Thr Gln Lys Glu Val His Leu Tyr Asn Ala Ser
            100                 105                 110

Arg Gly Ser Ala

<210> SEQ ID NO 65
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Lys Arg Lys Lys Lys Gly Lys Gly Leu Gly Lys Lys Arg Asp Pro Lys
1               5                   10                  15

Leu Arg Lys Tyr Lys Thr Leu Cys Gly Ala Glu Leu Val Asp Ala Leu
                20                  25                  30

Gln Phe Val Cys Gly Asp Arg Gly Phe Tyr Phe Asn Lys Pro Thr Gly
            35                  40                  45

Tyr Gly Ser Ser Ser Arg Arg Ala Pro Gln Thr Gly Ile Val Asp Glu
    50                  55                  60

Cys Cys Phe Arg Ser Cys Asp Leu Arg Arg Leu Glu Met Tyr Cys Ala
65                  70                  75                  80

Pro Leu Lys Pro Ala Lys Ser Ala Arg Ser Val Arg Ala Gln Arg His
                85                  90                  95

Thr Asp Met Pro Lys Thr Gln Lys Glu Val His Leu Lys Asn Ala Ser
                100                 105                 110

Arg Gly Ser Ala
    115

<210> SEQ ID NO 66
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Lys Arg Lys Lys Lys Gly Lys Gly Leu Gly Lys Lys Arg Asp Pro Arg
1               5                   10                  15

Leu Arg Lys Tyr Lys Thr Leu Cys Gly Ala Glu Leu Val Asp Ala Leu
                20                  25                  30

Gln Phe Val Cys Gly Asp Arg Gly Phe Tyr Phe Asn Lys Pro Thr Gly
            35                  40                  45

Tyr Gly Ser Ser Ser Arg Arg Ala Pro Gln Thr Gly Ile Val Asp Glu
    50                  55                  60

Cys Cys Phe Arg Ser Cys Asp Leu Arg Arg Leu Glu Met Tyr Cys Ala
65                  70                  75                  80

Pro Leu Lys Pro Ala Lys Ser Ala
                85

<210> SEQ ID NO 67
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Lys Arg Lys Lys Lys Gly Lys Gly Leu Gly Lys Lys Arg Asp Pro Lys
1               5                   10                  15

-continued

```
Leu Arg Lys Tyr Lys Thr Leu Cys Gly Ala Glu Leu Val Asp Ala Leu
            20                  25                  30

Gln Phe Val Cys Gly Asp Arg Gly Phe Tyr Phe Asn Lys Pro Thr Gly
        35                  40                  45

Tyr Gly Ser Ser Ser Arg Arg Ala Pro Gln Thr Gly Ile Val Asp Glu
 50                  55                  60

Cys Cys Phe Arg Ser Cys Asp Leu Arg Arg Leu Glu Met Tyr Cys Ala
 65                  70                  75                  80

Pro Leu Lys Pro Ala Lys Ser Ala
                85

<210> SEQ ID NO 68
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Lys Arg Lys Lys Lys Gly Lys Gly Leu Gly Lys Lys Arg Asp Pro Arg
1               5                   10                  15

Leu Arg Lys Tyr Lys Gly Gly Gly Thr Leu Cys Gly Ala Glu Leu Val
            20                  25                  30

Asp Ala Leu Gln Phe Val Cys Gly Asp Arg Gly Phe Tyr Phe Asn Lys
        35                  40                  45

Pro Thr Gly Tyr Gly Ser Ser Ser Arg Arg Ala Pro Gln Thr Gly Ile
 50                  55                  60

Val Asp Glu Cys Cys Phe Arg Ser Cys Asp Leu Arg Arg Leu Glu Met
 65                  70                  75                  80

Tyr Cys Ala Pro Leu Lys Pro Ala Lys Ser Ala Arg Ser Val Arg Ala
                85                  90                  95

Gln Arg His Thr Asp Met Pro Lys Thr Gln Lys Glu Val His Leu Lys
                100                 105                 110

Asn Ala Ser Arg Gly Ser Ala
        115

<210> SEQ ID NO 69
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Lys Arg Lys Lys Lys Gly Lys Gly Leu Gly Lys Lys Arg Asp Pro Lys
1               5                   10                  15

Leu Arg Lys Tyr Lys Gly Gly Gly Thr Leu Cys Gly Ala Glu Leu Val
            20                  25                  30

Asp Ala Leu Gln Phe Val Cys Gly Asp Arg Gly Phe Tyr Phe Asn Lys
        35                  40                  45

Pro Thr Gly Tyr Gly Ser Ser Ser Arg Arg Ala Pro Gln Thr Gly Ile
 50                  55                  60

Val Asp Glu Cys Cys Phe Arg Ser Cys Asp Leu Arg Arg Leu Glu Met
 65                  70                  75                  80

Tyr Cys Ala Pro Leu Lys Pro Ala Lys Ser Ala Arg Ser Val Arg Ala
                85                  90                  95
```

-continued

Gln Arg His Thr Asp Met Pro Lys Thr Gln Lys Glu Val His Leu Lys
            100                 105                 110

Asn Ala Ser Arg Gly Ser Ala
        115

<210> SEQ ID NO 70
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Lys Arg Lys Lys Lys Gly Lys Gly Leu Gly Lys Lys Arg Asp Pro Arg
1               5                   10                  15

Leu Arg Lys Tyr Lys Gly Gly Gly Thr Leu Cys Gly Ala Glu Leu Val
            20                  25                  30

Asp Ala Leu Gln Phe Val Cys Gly Asp Arg Gly Phe Tyr Phe Asn Lys
        35                  40                  45

Pro Thr Gly Tyr Gly Ser Ser Ser Arg Arg Ala Pro Gln Thr Gly Ile
    50                  55                  60

Val Asp Glu Cys Cys Phe Arg Ser Cys Asp Leu Arg Arg Leu Glu Met
65                  70                  75                  80

Tyr Cys Ala Pro Leu Lys Pro Ala Lys Ser Ala
                85                  90

<210> SEQ ID NO 71
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Lys Arg Lys Lys Lys Gly Lys Gly Leu Gly Lys Lys Arg Asp Pro Lys
1               5                   10                  15

Leu Arg Lys Tyr Lys Gly Gly Gly Thr Leu Cys Gly Ala Glu Leu Val
            20                  25                  30

Asp Ala Leu Gln Phe Val Cys Gly Asp Arg Gly Phe Tyr Phe Asn Lys
        35                  40                  45

Pro Thr Gly Tyr Gly Ser Ser Ser Arg Arg Ala Pro Gln Thr Gly Ile
    50                  55                  60

Val Asp Glu Cys Cys Phe Arg Ser Cys Asp Leu Arg Arg Leu Glu Met
65                  70                  75                  80

Tyr Cys Ala Pro Leu Lys Pro Ala Lys Ser Ala
                85                  90

<210> SEQ ID NO 72
<211> LENGTH: 116
<212> TYPE: PRT
<213> ORGANISM: Homo sapiens

<400> SEQUENCE: 72

Met Leu Ser Cys Arg Leu Gln Cys Ala Leu Ala Ala Leu Ser Ile Val
1               5                   10                  15

Leu Ala Leu Gly Cys Val Thr Gly Ala Pro Ser Asp Pro Arg Leu Arg
            20                  25                  30

```
Gln Phe Leu Gln Lys Ser Leu Ala Ala Ala Gly Lys Gln Glu Leu
            35                  40                  45

Ala Lys Tyr Phe Leu Ala Glu Leu Leu Ser Glu Pro Asn Gln Thr Glu
 50                      55                  60

Asn Asp Ala Leu Glu Pro Glu Asp Leu Ser Gln Ala Ala Glu Gln Asp
 65                  70                  75                  80

Glu Met Arg Leu Glu Leu Gln Arg Ser Ala Asn Ser Asn Pro Ala Met
                 85                  90                  95

Ala Pro Arg Glu Arg Lys Ala Gly Cys Lys Asn Phe Phe Trp Lys Thr
            100                 105                 110

Phe Thr Ser Cys
        115

<210> SEQ ID NO 73
<211> LENGTH: 460
<212> TYPE: PRT
<213> ORGANISM: Homo sapiens

<400> SEQUENCE: 73

Met Phe Thr Ile Lys Leu Leu Phe Ile Val Pro Leu Val Ile Ser
 1               5                  10                  15

Ser Arg Ile Asp Gln Asp Asn Ser Ser Phe Asp Ser Leu Ser Pro Glu
            20                  25                  30

Pro Lys Ser Arg Phe Ala Met Leu Asp Asp Val Lys Ile Leu Ala Asn
            35                  40                  45

Gly Leu Leu Gln Leu Gly His Gly Leu Lys Asp Phe Val His Lys Thr
 50                  55                  60

Lys Gly Gln Ile Asn Asp Ile Phe Gln Lys Leu Asn Ile Phe Asp Gln
 65                  70                  75                  80

Ser Phe Tyr Asp Leu Ser Leu Gln Thr Ser Glu Ile Lys Glu Glu Glu
                 85                  90                  95

Lys Glu Leu Arg Arg Thr Thr Tyr Lys Leu Gln Val Lys Asn Glu Glu
            100                 105                 110

Val Lys Asn Met Ser Leu Glu Leu Asn Ser Lys Leu Glu Ser Leu Leu
            115                 120                 125

Glu Glu Lys Ile Leu Leu Gln Gln Lys Val Lys Tyr Leu Glu Glu Gln
            130                 135                 140

Leu Thr Asn Leu Ile Gln Asn Gln Pro Glu Thr Pro Glu His Pro Glu
145                 150                 155                 160

Val Thr Ser Leu Lys Thr Phe Val Glu Lys Gln Asp Asn Ser Ile Lys
                 165                 170                 175

Asp Leu Leu Gln Thr Val Glu Asp Gln Tyr Lys Gln Leu Asn Gln Gln
            180                 185                 190

His Ser Gln Ile Lys Glu Ile Glu Asn Gln Leu Arg Arg Thr Ser Ile
            195                 200                 205

Gln Glu Pro Thr Glu Ile Ser Leu Ser Ser Lys Pro Arg Ala Pro Arg
            210                 215                 220

Thr Thr Pro Phe Leu Gln Leu Asn Glu Ile Arg Asn Val Lys His Asp
225                 230                 235                 240

Gly Ile Pro Ala Glu Cys Thr Thr Ile Tyr Asn Arg Gly Glu His Thr
                 245                 250                 255

Ser Gly Met Tyr Ala Ile Arg Pro Ser Asn Ser Gln Val Phe His Val
            260                 265                 270

Tyr Cys Asp Val Ile Ser Gly Ser Pro Trp Thr Leu Ile Gln His Arg
            275                 280                 285
```

Ile Asp Gly Ser Gln Asn Phe Asn Glu Thr Trp Glu Asn Tyr Lys Tyr
290                 295                 300

Gly Phe Gly Arg Leu Asp Gly Glu Phe Trp Leu Gly Leu Glu Lys Ile
305                 310                 315                 320

Tyr Ser Ile Val Lys Gln Ser Asn Tyr Val Leu Arg Ile Glu Leu Glu
                325                 330                 335

Asp Trp Lys Asp Asn Lys His Tyr Ile Glu Tyr Ser Phe Tyr Leu Gly
            340                 345                 350

Asn His Glu Thr Asn Tyr Thr Leu His Leu Val Ala Ile Thr Gly Asn
        355                 360                 365

Val Pro Asn Ala Ile Pro Glu Asn Lys Asp Leu Val Phe Ser Thr Trp
370                 375                 380

Asp His Lys Ala Lys Gly His Phe Asn Cys Pro Glu Gly Tyr Ser Gly
385                 390                 395                 400

Gly Trp Trp Trp His Asp Glu Cys Gly Glu Asn Asn Leu Asn Gly Lys
                405                 410                 415

Tyr Asn Lys Pro Arg Ala Lys Ser Lys Pro Glu Arg Arg Gly Leu
                420                 425                 430

Ser Trp Lys Ser Gln Asn Gly Arg Leu Tyr Ser Ile Lys Ser Thr Lys
        435                 440                 445

Met Leu Ile His Pro Thr Asp Ser Glu Ser Phe Glu
450                 455                 460

<210> SEQ ID NO 74
<211> LENGTH: 215
<212> TYPE: PRT
<213> ORGANISM: Homo sapiens

<400> SEQUENCE: 74

Gly Ile Pro Ala Glu Cys Thr Thr Ile Tyr Asn Arg Gly Glu His Thr
1               5                   10                  15

Ser Gly Met Tyr Ala Ile Arg Pro Ser Asn Ser Gln Val Phe His Val
                20                  25                  30

Tyr Cys Asp Val Ile Ser Gly Ser Pro Trp Thr Leu Ile Gln His Arg
            35                  40                  45

Ile Asp Gly Ser Gln Asn Phe Asn Glu Thr Trp Glu Asn Tyr Lys Tyr
50                  55                  60

Gly Phe Gly Arg Leu Asp Gly Glu Phe Trp Leu Gly Leu Glu Lys Ile
65                  70                  75                  80

Tyr Ser Ile Val Lys Gln Ser Asn Tyr Val Leu Arg Ile Glu Leu Glu
                85                  90                  95

Asp Trp Lys Asp Asn Lys His Tyr Ile Glu Tyr Ser Phe Tyr Leu Gly
            100                 105                 110

Asn His Glu Thr Asn Tyr Thr Leu His Leu Val Ala Ile Thr Gly Asn
        115                 120                 125

Val Pro Asn Ala Ile Pro Glu Asn Lys Asp Leu Val Phe Ser Thr Trp
130                 135                 140

Asp His Lys Ala Lys Gly His Phe Asn Cys Pro Glu Gly Tyr Ser Gly
145                 150                 155                 160

Gly Trp Trp Trp His Asp Glu Cys Gly Glu Asn Asn Leu Asn Gly Lys
                165                 170                 175

Tyr Asn Lys Pro Arg Ala Lys Ser Lys Pro Glu Arg Arg Gly Leu
                180                 185                 190

Ser Trp Lys Ser Gln Asn Gly Arg Leu Tyr Ser Ile Lys Ser Thr Lys

```
                195                 200                 205

Met Leu Ile His Pro Thr Asp
    210                 215

<210> SEQ ID NO 75
<211> LENGTH: 231
<212> TYPE: PRT
<213> ORGANISM: Homo sapiens

<400> SEQUENCE: 75

Thr Thr Pro Phe Leu Gln Leu Asn Glu Ile Arg Asn Val Lys His Asp
1               5                   10                  15

Gly Ile Pro Ala Glu Cys Thr Thr Ile Tyr Asn Arg Gly Glu His Thr
            20                  25                  30

Ser Gly Met Tyr Ala Ile Arg Pro Ser Asn Ser Gln Val Phe His Val
        35                  40                  45

Tyr Cys Asp Val Ile Ser Gly Ser Pro Trp Thr Leu Ile Gln His Arg
50                  55                  60

Ile Asp Gly Ser Gln Asn Phe Asn Glu Thr Trp Glu Asn Tyr Lys Tyr
65                  70                  75                  80

Gly Phe Gly Arg Leu Asp Gly Glu Phe Trp Leu Gly Leu Glu Lys Ile
                85                  90                  95

Tyr Ser Ile Val Lys Gln Ser Asn Tyr Val Leu Arg Ile Glu Leu Glu
            100                 105                 110

Asp Trp Lys Asp Asn Lys His Tyr Ile Glu Tyr Ser Phe Tyr Leu Gly
        115                 120                 125

Asn His Glu Thr Asn Tyr Thr Leu His Leu Val Ala Ile Thr Gly Asn
    130                 135                 140

Val Pro Asn Ala Ile Pro Glu Asn Lys Asp Leu Val Phe Ser Thr Trp
145                 150                 155                 160

Asp His Lys Ala Lys Gly His Phe Asn Cys Pro Glu Gly Tyr Ser Gly
                165                 170                 175

Gly Trp Trp Trp His Asp Glu Cys Gly Glu Asn Asn Leu Asn Gly Lys
            180                 185                 190

Tyr Asn Lys Pro Arg Ala Lys Ser Lys Pro Glu Arg Arg Arg Gly Leu
        195                 200                 205

Ser Trp Lys Ser Gln Asn Gly Arg Leu Tyr Ser Ile Lys Ser Thr Lys
    210                 215                 220

Met Leu Ile His Pro Thr Asp
225                 230

<210> SEQ ID NO 76
<211> LENGTH: 248
<212> TYPE: PRT
<213> ORGANISM: Homo sapiens

<400> SEQUENCE: 76

Ile Gln Glu Pro Thr Glu Ile Ser Leu Ser Ser Lys Pro Arg Ala Pro
1               5                   10                  15

Arg Thr Thr Pro Phe Leu Gln Leu Asn Glu Ile Arg Asn Val Lys His
            20                  25                  30

Asp Gly Ile Pro Ala Glu Cys Thr Thr Ile Tyr Asn Arg Gly Glu His
        35                  40                  45

Thr Ser Gly Met Tyr Ala Ile Arg Pro Ser Asn Ser Gln Val Phe His
    50                  55                  60

Val Tyr Cys Asp Val Ile Ser Gly Ser Pro Trp Thr Leu Ile Gln His
```

```
            65                  70                  75                  80
Arg Ile Asp Gly Ser Gln Asn Phe Asn Glu Thr Trp Glu Asn Tyr Lys
                85                  90                  95

Tyr Gly Phe Gly Arg Leu Asp Gly Glu Phe Trp Gly Leu Glu Lys
            100                 105                 110

Ile Tyr Ser Ile Val Lys Gln Ser Asn Tyr Val Leu Arg Ile Glu Leu
            115                 120                 125

Glu Asp Trp Lys Asp Asn Lys His Tyr Ile Gly Tyr Ser Phe Tyr Leu
130                 135                 140

Gly Asn His Glu Thr Asn Tyr Thr Leu His Leu Val Ala Ile Thr Gly
145                 150                 155                 160

Asn Val Pro Asn Ala Ile Pro Glu Asn Lys Asp Leu Val Phe Ser Thr
                165                 170                 175

Trp Asp His Lys Ala Lys Gly His Phe Asn Cys Pro Glu Gly Tyr Ser
            180                 185                 190

Gly Gly Trp Trp Trp His Asp Glu Cys Gly Glu Asn Leu Asn Gly
            195                 200                 205

Lys Tyr Asn Lys Pro Arg Ala Lys Ser Lys Pro Glu Arg Arg Gly
210                 215                 220

Leu Ser Trp Lys Ser Gln Asn Gly Arg Leu Tyr Ser Ile Lys Ser Thr
225                 230                 235                 240

Lys Met Leu Ile His Pro Thr Asp
                245

<210> SEQ ID NO 77
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Arg Ala Asp Ala Arg Ala Asp Ala Arg Ala Asp Ala Arg Ala Asp Ala
1               5                   10                  15

<210> SEQ ID NO 78
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Lys Leu Asp Leu Lys Leu Asp Leu Lys Leu Asp Leu
1               5                   10

<210> SEQ ID NO 79
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term AcN
<220> FEATURE:
<223> OTHER INFORMATION: C-term CNH2

<400> SEQUENCE: 79

Lys Leu Asp Leu Lys Leu Asp Leu Lys Leu Asp Leu
```

```
<210> SEQ ID NO 80
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (35)..(35)
<223> OTHER INFORMATION: Lys-biotin

<400> SEQUENCE: 80

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Lys
        35

<210> SEQ ID NO 81
<211> LENGTH: 59
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (59)..(59)
<223> OTHER INFORMATION: Lys-biotin

<400> SEQUENCE: 81

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Gly Gly Gly Lys Arg Lys Lys Gly Lys Gly Leu Gly Lys
        35                  40                  45

Lys Arg Asp Pro Arg Leu Arg Lys Tyr Lys Lys
        50                  55

<210> SEQ ID NO 82
<211> LENGTH: 209
<212> TYPE: PRT
<213> ORGANISM: Homo sapiens

<400> SEQUENCE: 82

Met Gly Lys Gly Asp Pro Asn Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ser Ser Val Asn Phe Ala Glu Phe Ser Lys Lys Cys Ser Glu Arg
        35                  40                  45

Trp Lys Thr Met Ser Ala Lys Glu Lys Ser Lys Phe Glu Asp Met Ala
    50                  55                  60

Lys Ser Asp Lys Ala Arg Tyr Asp Arg Glu Met Lys Asn Tyr Val Pro
65                  70                  75                  80

Pro Lys Gly Asp Lys Lys Gly Lys Lys Asp Pro Asn Ala Pro Lys
                85                  90                  95
```

-continued

```
Arg Pro Pro Ser Ala Phe Phe Leu Phe Cys Ser Glu His Arg Pro Lys
            100             105                 110

Ile Lys Ser Glu His Pro Gly Leu Ser Ile Gly Asp Thr Ala Lys Lys
        115             120                 125

Leu Gly Glu Met Trp Ser Glu Gln Ser Ala Lys Asp Lys Gln Pro Tyr
    130             135                 140

Glu Gln Lys Ala Ala Lys Leu Lys Glu Lys Tyr Glu Lys Asp Ile Ala
145             150                 155                 160

Ala Tyr Arg Ala Lys Gly Lys Ser Glu Ala Gly Lys Lys Gly Pro Gly
                165             170                 175

Arg Pro Thr Gly Ser Lys Lys Lys Asn Glu Pro Glu Asp Glu Glu Glu
            180             185                 190

Glu Glu Glu Glu Glu Asp Glu Asp Glu Glu Glu Glu Asp Glu Asp Glu
        195                 200                 205

Glu
```